(12) United States Patent
Kuriger et al.

(10) Patent No.: US 11,371,515 B2
(45) Date of Patent: Jun. 28, 2022

(54) REGENERATIVE BLOWER

(71) Applicant: Fisher & Paykel Healthcare Limited, Auckland (NZ)

(72) Inventors: Donald Roy Kuriger, Auckland (NZ); Johannes Nicolaas Bothma, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 114 days.

(21) Appl. No.: 16/761,222

(22) PCT Filed: Feb. 11, 2018

(86) PCT No.: PCT/IB2018/058600
§ 371 (c)(1),
(2) Date: May 1, 2020

(87) PCT Pub. No.: WO2019/087134
PCT Pub. Date: May 9, 2019

(65) Prior Publication Data
US 2020/0309137 A1     Oct. 1, 2020

Related U.S. Application Data

(60) Provisional application No. 62/581,449, filed on Nov. 3, 2017.

(51) Int. Cl.
*F04D 23/00* (2006.01)
*A61M 16/00* (2006.01)
(Continued)

(52) U.S. Cl.
CPC ....... *F04D 23/008* (2013.01); *A61M 16/0066* (2013.01); *F04D 25/0606* (2013.01);
(Continued)

(58) Field of Classification Search
CPC .............. F04D 23/008; F04D 25/0606; F04D 29/4213; F04D 29/4246; F05D 2250/53
See application file for complete search history.

(56) References Cited

U.S. PATENT DOCUMENTS 3,761,203 A     9/1973   Neidhardt et al.
3,915,589 A  *  10/1975  Vander Linden ..... F04D 23/008
                                                                415/55.4
(Continued)

FOREIGN PATENT DOCUMENTS

EP     0636791      2/1995
GB     2 126 652    3/1984
(Continued)

OTHER PUBLICATIONS

Australian Examination Report for Application No. 2018361976 dated Oct. 16, 2020, 5 pages.
(Continued)

*Primary Examiner* — Ninh H. Nguyen
(74) *Attorney, Agent, or Firm* — Knobbe Martens Olson and Bear, LLP

(57) ABSTRACT

In accordance with one aspect the present invention may comprise a regenerative blower comprising: a housing, a first port and second port in the housing, an airflow channel extending between the first and second ports for airflow between the ports, an impeller rotatable in an impeller channel to promote airflow in the airflow channel from the first port to the second port, a motor to drive the impeller, and an interrupter between the first and second ports to limit airflow from the second port to the first port.

13 Claims, 60 Drawing Sheets

(51) Int. Cl.
   *F04D 25/06*     (2006.01)
   *F04D 29/42*     (2006.01)
   *F04D 29/18*     (2006.01)
   *F04D 29/66*     (2006.01)

(52) U.S. Cl.
   CPC ..... *F04D 29/4213* (2013.01); *F04D 29/4246* (2013.01); *A61M 2205/42* (2013.01); *F04D 29/188* (2013.01); *F04D 29/666* (2013.01); *F05B 2240/20* (2013.01); *F05B 2250/501* (2013.01); *F05D 2250/53* (2013.01)

(56) References Cited

U.S. PATENT DOCUMENTS

| | | | |
|---|---|---|---|
| 4,306,833 A * | 12/1981 | Sixsmith | F04D 29/161 415/55.4 |
| 4,932,833 A | 6/1990 | Wieja et al. | |
| 5,163,810 A | 11/1992 | Smith | |
| 5,600,886 A * | 2/1997 | Asabuki | F04D 29/281 29/889.3 |
| 7,806,649 B2 * | 10/2010 | Ishikawa | F04D 23/008 415/55.1 |
| 8,123,506 B2 | 2/2012 | Schwartz et al. | |
| 9,297,276 B2 | 3/2016 | Herrmann et al. | |
| 9,453,511 B2 | 7/2016 | Quail | |
| 2005/0207883 A1 | 9/2005 | Shufeldt | |
| 2009/0155102 A1 * | 6/2009 | Park | F04D 23/008 417/423.1 |
| 2012/0073950 A1 | 3/2012 | Kamen et al. | |
| 2014/0170000 A1 | 6/2014 | Paffrath | |

FOREIGN PATENT DOCUMENTS

| | | |
|---|---|---|
| JP | 2008/175084 | 7/2008 |
| WO | WO 2016/110371 | 7/2016 |

OTHER PUBLICATIONS

International Search Report for International Application No. PCT/IB2018/058600 dated Dec. 17, 2018.

* cited by examiner

*Pressure v Flow*
*for RG1 open/blocked and RG2 open/blocked at 10,000 rpm*

*Power v Flow*
*for RG1 and RG2*

*Pressure v Flow*
*for RG1 open/blocked and RG2 open/blocked at 10,000 rpm*

*Power v Flow*
*for RG2 and RG2.1*

*Pressure v Flow relationship of RG3*

*Power v Flow relationship of RG3*

*Noise test RG3.1*
*comparing full to offset & web impeller blades*

*Noise test RG3*
*comparing full to offset & web impeller blades*

*Noise test RG3.2  
comparing full to offset & web impeller blades*

*Noise test RG3.3  
comparing full to offset & web impeller blades*

*RG3.4 v RG3*
*Pressure - Flow curves*

*RG3.4 v RG3*
*Power - Flow curves*

REGENERATIVE BLOWER

INCORPORATION BY REFERENCE TO ANY PRIORITY APPLICATIONS

This application is a national phase of PCT Application No. PCT/IB2018/058600, filed Feb. 11, 2018, which claims priority to U.S. Provisional Application No. 62/581,449, filed Nov. 3, 2017. Any and all applications for which a foreign or domestic priority claim is identified in the Application Data Sheet as filed with the present application are hereby incorporated by reference under 37 CFR 1.57.

FIELD OF THE INVENTION

The present description relates to regenerative blowers and various configurations. Such regenerative blowers can be used in respiratory apparatus, and other end-use applications.

BACKGROUND

A regenerative blower comprises a housing with an airflow channel for flow of air from an inlet to an outlet. An impeller driven by a motor rotate is in a channel that is pneumatically connected to the airflow channel. The impeller rotates to provide a flow of air within the airflow channel from the inlet to the outlet. The airflow channel has an interrupter positioned between the inlet and outlet to prevent airflow going directly from the outlet to the inlet.

SUMMARY OF INVENTION

It is an object of the present invention to provide an improved regenerative blower.

In accordance with one aspect the present invention may comprise a regenerative blower comprising: a housing, a first port and second port in the housing, an airflow channel extending between the first and second ports for airflow between the ports, an impeller rotatable in an impeller channel to promote airflow in the airflow channel from the first port to the second port, a motor to drive the impeller, and an interrupter between the first and second ports to limit airflow from the second port to the first port.

Optionally the first port is an inlet port and the second port is an outlet port and the impeller rotates in a direction to promote airflow in the airflow channel from the inlet port to the outlet port.

Optionally the airflow channel comprises an arcuate channel connecting the first and second ports, the first port is in fluid communication with a first end of the arcuate channel, the second port is in fluid communication with a second end of the arcuate channel, and the interrupter comprises a wall formed between the first and second ends of the arcuate channel.

Optionally the wall has a leading face facing towards the second end of the arcuate channel.

Optionally the leading face is curved.

Optionally the impeller blades are adapted to rotate in use and transit the interrupter by first transiting a leading edge of the leading face.

Optionally the wall includes a trailing face facing towards the first end of the arcuate channel.

Optionally the trailing face is curved.

Optionally the impeller blades are adapted to rotate in use and transit the interrupter by transiting the leading edge, transiting a central portion of the wall, and then transiting a trailing edge the trailing face.

Optionally the leading edge is configured such that a portion of each blade passes a portion of the leading edge at an angle during transit of that blade past the interrupter.

Optionally the trailing edge is configured such that a portion of each blade passes a portion of the trailing edge at an angle during transit of that blade past the interrupter.

Optionally the leading edge is configured such that more than one of the blades is in transit past the leading edge at any point in time during rotation of the impeller.

Optionally the trailing edge is configured such that more than one of the blades is in transit past the trailing edge at any point in time during rotation of the impeller.

Optionally the leading edge is orientated at an angle relative to blades of the impeller as they pass.

Optionally the leading edge is curved to thereby present at an angle relative to blades of the impeller as they pass.

Optionally the trailing edge is orientated at an angle relative to blades of the impeller as they pass.

Optionally the trailing edge is curved to thereby present at an angle relative to blades of the impeller as they pass.

Optionally the leading edge is curved.

Optionally the trailing edge is curved.

Optionally the interrupter extends past the first port and/or extends past the second port.

Optionally the wall has a first side face proximate the first end of the arcuate channel, the impeller blades adapted in use to rotate away from and pass the first side face, wherein the first side face comprises a recess.

Optionally the wall has a second side face proximate the second end of the arcuate channel, the impeller blades adapted in use to rotate towards and pass the second side face, wherein the second side face comprises a recess.

Optionally the first side face forms part of the first port, and the second side face forms part of the second port.

Optionally the wall comprises a transverse face located between the first and second ends of the arcuate channel, the impeller blades adapted in use to rotate past the transverse face, wherein the transverse face comprises a recess.

Optionally the recess on the first side face and/or the recess on the second side face extends along the face.

Optionally the recess is a "V" shape in cross-section.

Optionally the recess on the first side face and/or the recess on the second side face comprises: a) curves inwards from a back edge to a front edge along the centre axis, and b) curves inwards from top and bottom edges towards a centre axis between the top and bottom edges.

Optionally the recess on the transverse face extends laterally along the face.

Optionally there are two recess extending laterally across the transverse face.

Optionally the two recess are substantially parallel.

Optionally each recess spans a length of the transverse face from the first side face to the second side face.

Optionally the recess is a "V" shape in cross-section.

Optionally each recess starts with a maximum width and depth at a one edge of the transverse face decreasing to a minimum width and depth towards the centre of the transverse face and then expanding out to a maximum width and depth at the opposite edge of the transverse face.

Optionally each recess starts with a maximum width of approximately 50% of the total width of the transverse face at each end of the transverse face, and has a minimum width towards the centre of the transverse face.

In accordance with another aspect the present invention may comprise a regenerative blower comprising: a housing, a first port and second port in the housing, an airflow channel extending between the first and second ports for airflow, an impeller rotatable in an impeller channel to promote airflow in the airflow channel from the first port to the second port, a motor to drive the impeller and an interrupter between the first and second ports to limit airflow from the second port to the first port, wherein the first port comprises a conduit that extends from the airflow channel, and the second port comprises a conduit that extends from the airflow channel, and the first port forms a spiral with the airflow channel.

Optionally the second port forms a spiral with the airflow channel.

Optionally the first port extends from the airflow channel as a helix with a partial turn, a variable pitch and a variable radius.

Optionally the first port extends from the airflow channel as a helix with a partial turn and a substantially constant pitch and radius.

Optionally the second port extends from the airflow channel as a helix with a partial turn and a variable pitch and a variable radius.

Optionally the second port extends from the airflow channel as a helix with a partial turn and a substantially constant pitch and radius.

Optionally the variable pitch varies from approximately 10 to 30 mm approximately adjacent to the airflow channel, to approximately 90 to 110 mm at a distal end.

Optionally the variable radius varies from approximately 25 to 30 mm approximately adjacent to the airflow channel, to approximately 10 to 20 mm at the distal end.

Optionally the partial turn spans 72° to 114° of a complete revolution, or 20-40% of the complete revolution.

Optionally the variable pitch varies from approximately 2-20 mm approximately adjacent to the airflow channel, to approximately 80-120 mm at a distal end.

Optionally the variable radius varies from approximately 20-35 mm approximately adjacent to the airflow channel, to approximately 20-70 mm at a distal end.

Optionally the partial turn spans 36°-144° of a complete revolution, or 10-40% of the complete revolution.

Optionally the motor comprises a rotor and the housing comprises an aperture with a diameter that is shaped to enable, during manufacture, an assembly of the rotor coupled to the impeller by a shaft to be placed in the housing through the aperture.

Optionally the housing comprises a top housing and a bottom housing with a bottom plate, and the aperture is in the bottom plate of the bottom housing.

Optionally the aperture provides a third port.

Optionally the bottom housing comprises an impeller housing and a bottom housing cap.

Optionally the bottom housing cap includes at least one bottom housing cap aperture.

Optionally the aperture is an outlet from the impeller channel and/or the airflow channel under relatively low flow conditions, and an inlet under relatively high flow conditions.

Optionally the housing comprises a top housing and a bottom housing, the impeller is disposed in the top housing, the motor is disposed at least partially in the bottom housing and the top housing is open to the bottom housing such that there is no plate or other barrier of the housing separating the impeller and the motor.

Optionally the airflow channel comprises an upper channel and a lower channel.

Optionally the impeller channel separates the upper channel and the lower channel.

Optionally lateral ends of the impeller rotate adjacent an interior lateral face of the housing.

Optionally the clearance between the lateral ends of the impeller and the interior lateral face of the housing is about 0.5 mm to 1 mm.

In accordance with another aspect the present invention may comprise an impeller for a regenerative blower comprising: a hub, a first set of blades supported from and arranged around the hub, and a second set of blade supported from and arranged around the hub.

Optionally the first set of blades of blades are arranged axially above the second set of blades, and the first set of blades is rotationally offset from the second set of blades.

Optionally the first and second set of blades are arranged annularly around the hub.

Optionally the regenerative blower further comprises a web between the first and second sets of blades.

Optionally the first set of blades is arranged annularly around the hub and the second set of blades is arranged concentrically within the first set of blades around the hub.

Optionally the regenerative blower further comprises a third set of blades, wherein the third set of blades are arranged annularly around the hub, the first set of blades are arranged axially above the third set of blades, and the first set of blades is rotationally offset from the third set of blades.

Optionally the regenerative blower further comprises a web between the first and third sets of blades.

Optionally the second set or third set of blades are offset from the first set of blades by:

$$\theta = \frac{360}{2N} \pm X \text{ degrees, or}$$

$$\theta = \frac{\pi}{N} \pm X \text{ radians}$$

Where $\theta$ is the angle that the second or third set of blades are offset relative to the first set of blades, N is the number of first impeller blades and X is an offset angle.

In accordance with another aspect the present invention may comprise a regenerative blower comprising: a housing, a first port and second port in the housing, an airflow channel extending between the first and second ports for airflow an impeller according to any preceding statement in an impeller channel to promote airflow in the channel from the first port to the second port, a motor to drive the impeller and an interrupter between the first and second ports to limit airflow from the second port to the first port.

In accordance with another aspect the present invention may comprise a regenerative blower comprising: a housing, a first port and second port in the housing providing an inlet and outlet, an airflow channel extending between the first and second ports, an impeller rotatable in an impeller channel to promote airflow in the airflow channel from the first port to the second port, a motor to drive the impeller and an interrupter between the first and second ports to limit airflow from the second port to the first port, wherein the housing comprises an aperture that provides a third port.

Optionally the housing comprises a top housing and a bottom housing and the aperture comprises one or more openings in the top housing.

Optionally the housing comprises a top housing and a bottom housing and the aperture comprises one or more openings in the bottom housing.

Optionally the aperture is an additional inlet port or an outlet port.

Optionally the airflow channel comprises an outer airflow channel extending between the first and second ports, and an inner airflow channel.

Optionally the inner airflow channel is formed from an arcuate wall between the inner airflow channel and outer airflow channel, wherein the wall has an airflow opening allow airflow between the inner airflow channel and outer airflow channel. Optionally the impeller channel comprises an outer impeller channel and an inner impeller channel, wherein the inner airflow channel is the inner impeller channel.

Optionally, the regenerative blower comprises a common channel that includes the airflow channel and the impeller channel.

Optionally, the impeller comprises an axial axis about which the impeller is rotatable, and wherein the first set of blades are axially displaced with respect to the second set of blades, and the first set of blades is rotationally offset around the axial axis from the second set of blades.

Optionally, the web is an annular impeller support plate.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The invention consists in the foregoing and also envisages constructions of which the following gives examples only.

BRIEF DESCRIPTION OF THE DRAWINGS

Embodiments will now be described, of which.

DETAILED DESCRIPTION

1. Gas Flow Apparatus Using Regenerative Blower

The regenerative blower described herein in various embodiments can be used in any suitable gas flow apparatus application. The regenerative blower described can be particularly useful for respiration apparatus, but is not restricted to use solely in that application. Other applications where a regenerative blower as described could be used could be envisaged by those skilled in the art. Also, the regenerative blower could be reconfigured to act as a vacuum and be used in any suitable gas flow apparatus where a vacuum is required. For example, the regenerative blower described herein can be configured as a suction generating device. Such a suction generating device could be used as part of a suction system, or a system configured to provide suction. The regenerative blower will be arranged to generate suction or a partial vacuum at the inlet, and connected tubing. This allows the blower to be used as a gas evacuation or gas removal device.

Figure 106:
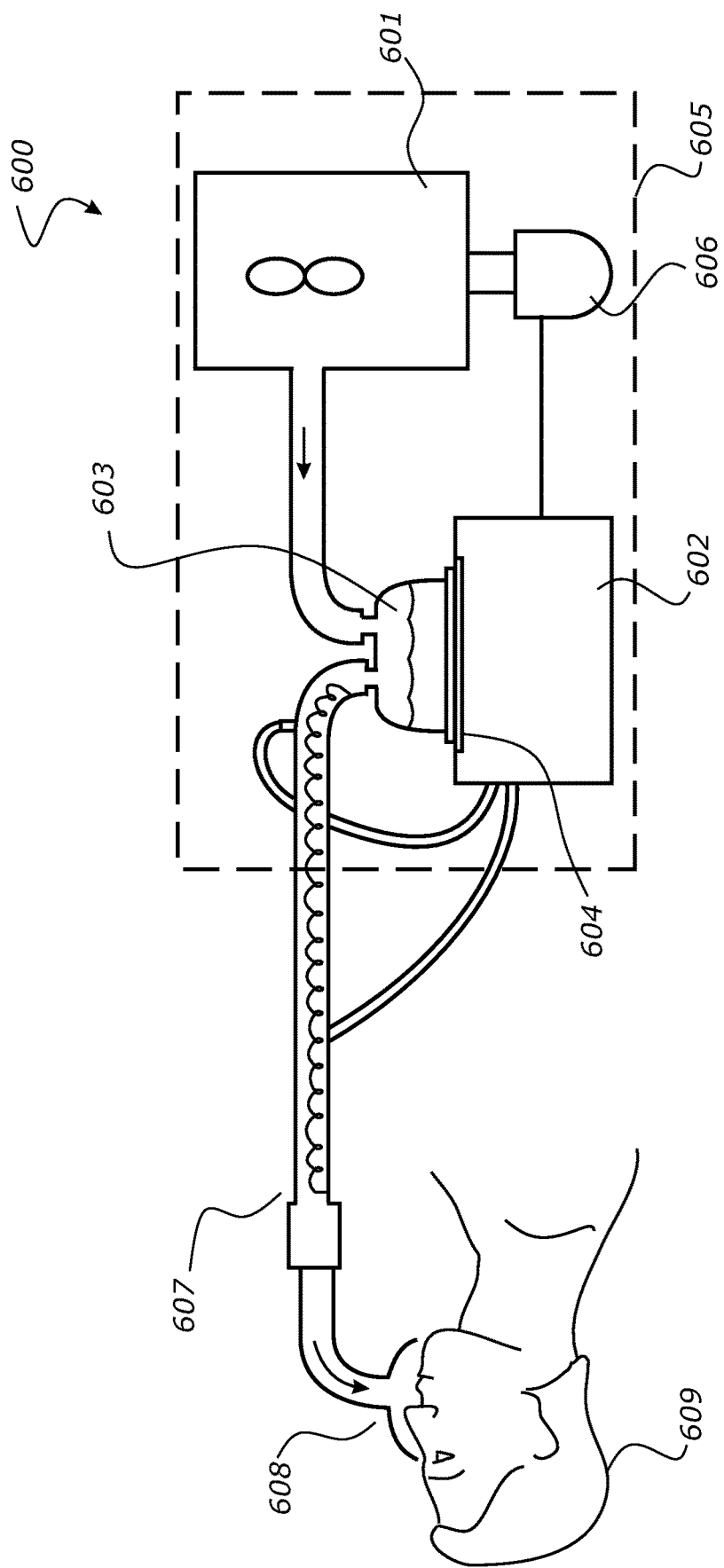
FIG. 106 is a diagram of a respiratory apparatus, such as a continuous positive airway pressure (CPAP), high flow therapy, non-invasive ventilation or other respiratory apparatus that utilises a regenerative blower such as described herein.

By way of nonlimiting example, the regenerative blower described herein could be used in the application shown in FIG. 106. FIG. 106 shows a respiratory apparatus 600, such as a continuous positive airway pressure (CPAP) apparatus, a nasal high flow apparatus, a non-invasive ventilation (NIV) apparatus, a ventilator or other respiratory apparatus. The respiratory apparatus 600 comprises a blower 601 (also can be termed "flow generator") for generating a gases flow and/or pressure. The blower 601 can optionally be coupled to a humidifier 602 and tub for water 603 for humidifying gases from the blower. The humidifier 602 can have a heater plate 604 and appropriate control circuitry to heat water in the tub. The humidifier 602 and blower 601 can be separate components, or integrated into a housing 605, such as shown in dotted lines. One or more controllers 606 can control operation of the respiratory apparatus 600. A gases supply from the blower 601 is passed to the humidifier 602, and the humidified gases supply passed down a breathing conduit 607 to a patient interface 608 and patient 609.

The blower 601 is a regenerative blower, such as one of the embodiments described herein. The blower herein can be used in any suitable respiratory apparatus, also including a lung cycling machine. The regenerative blower described herein could be used in respiratory apparatus where traditionally a centrifugal blower would be used.

2. Regenerative Blower for Use in a Gas Flow Apparatus

Various embodiments of a regenerative blower will be described, each for use in a gas flow apparatus, such as one of those described above.

2.1 Overview of Embodiments

Figure 1:
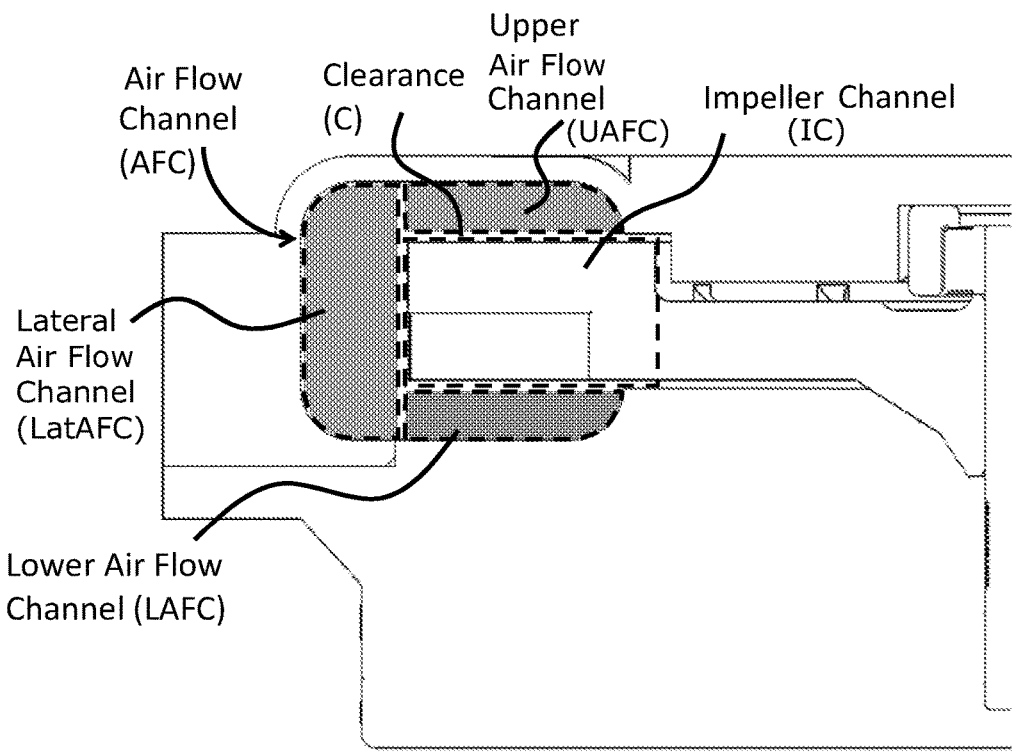
FIG. 1 shows in diagrammatic form a regenerative blower with a channel comprising upper, lower and lateral airflow channels, and an impeller channel.

Referring to FIG. 1, which shows a cross section of a regenerative blower (also termed a "side-channel blower") in diagrammatic form, general features of the regenerative blower embodiments described in here will be indicated.

The regenerative blower (hereinafter: "blower") has a housing, which can be formed from multiple sub-housings, such as a top housing and bottom housing. The housing provides a region for a motor which drives an impeller (with impeller blades) via a shaft. In some configurations, the impeller can be overmolded onto a shaft. Alternatively, the impeller can be independently molded and connected to a shaft. Alternatively, in another configuration, the impeller can be made from a metal, a composite (e.g. carbon fibre), or another material suitable for a lightweight impeller. There are one or more ports providing one or more inlets and outlets to the housing to enable ingress and egress of air, the airflow being driven by the impeller. A port comprises an aperture and preferably a collar. Whether a port is an inlet or outlet depends on the direction of rotation of the impeller and the direction of flow of air. A port can swap between being an inlet and outlet or vice versa, depending on the rotation direction of the impeller.

The regenerative blower has a channel formed in the housing. The channel can take various different forms in the different embodiments, and can be formed in various manners by the configuration and interconnection of the sub-housings. The channel comprises various channel regions, and each of the channel regions takes a suitable shape/configuration. The channel comprises an impeller region ("impeller channel"), which the impeller blades reside and rotate within to generate a flow of air from the inlet to the outlet. The impeller channel (IC) is annular to receive the blades of the impeller, which are arranged in a generally annular fashion. An air recirculation path allows the recirculating air to encounter the impeller multiple times on its way from the inlet to the outlet. The air continuously cycles through the air recirculation path enabling a successive pressure increase at each pass, producing the regenerative characteristic of the blower.

The channel also comprises an airflow region ("airflow channel (AFC)") in fluid communication with the impeller channel (IC). The inlet and outlet ports are in fluid communication with the airflow channel (AFC). Rotation of the impeller blades provides for a flow of air in the airflow channel (AFC) from the inlet port to the outlet port. (Rotation of the impeller blades also provides a flow of air in the impeller channel (IC)). The airflow channel (AFC) can take many different configurations, depending on the requirements of the embodiment. For example, the airflow channel (AFC) can be arcuate. An interrupter sits within the channel to prevent, minimise or at least reduce (more generally "limit") airflow between the outlet port to the inlet port (that is, between the ports). Further, the airflow channel (AFC) can comprise one or more of a combination of multiple different airflow channels or regions, including an upper airflow channel (UAFC), a lateral airflow channel (LatAFC) and a lower airflow channel (LAC). In at least one configuration, the upper airflow channel (UAFC) can be on an opposing side of the impeller to the lower airflow channel (LAFC). There can also be in an inner airflow channel, which will be described later. It should be appreciated that reference to upper, lateral and lower channels does not indicate any absolute or particular orientation or restrict the scope of the embodiments described to such orientations. Rather, it is just a terminology used in relation to the drawings as they are presented to provide relative orientations, not absolute orientations. For example, in use, the airflow channels (AFC) could be orientated such that the upper airflow channel (UAFC) is underneath, the lower airflow channel (LAFC) is on top, or even at any other orientation.

The various airflow channel regions that make up the airflow channel (AFC) can be formed by the configuration and interconnection of the sub-housings and other aspects of design. Various combinations of the airflow channel (AFC) regions can provide desired characteristics of the blower.

Conventional regenerative blowers are large and relatively noisy, and therefore can be unsuitable for use in respiratory devices. Surprisingly, the regenerative blowers as described herein can be sufficiently quiet for use in respiratory devices. Without wishing to be bound by theory, it is considered that the lose noise produced at least in part by the regenerative blowers described herein is a result of the impeller design and/or the housing design. Additionally, the regenerative blowers as described herein are of a reduced size relative to prior art regenerative blowers, and feature a lightweight impeller, which allows the blower to be suitably used in applications requiring rapid direction change of flow. Typically regenerative blowers are used for high pressure, low flow applications. As only pressures of 0-30 cmH2O are needed in some respiratory applications, it is possible to have various leaks (caused by a relatively large gap/clearance between the impeller blades and the interrupter, and the central opening for example), and the motor/impeller combination is still capable of providing the desired pressure and flow range. The gaps that are described herein would be unacceptable for regenerative blowers that require very high pressure and low flow.

Various embodiments will now be described, each of which provide various configurations of the airflow and impeller channels.

2.2 First Embodiment of a Regenerative Blower

FIGS. 2 to 18 show a regenerative blower according to a first embodiment.

2.2.1 Overview

An overview of the regenerative blower 100 will be described with reference to FIGS. 2 to 5B. The regenerative blower comprises a housing 101. The housing includes a top housing 102 and bottom housing 103. The top housing 102 and the bottom housing 103 are coupled together to form an interior region for a motor and a channel 104. The channel 104 comprises an airflow channel 132 and an impeller channel 145 (also termed "airflow and impeller regions"). It should be appreciated that reference to a top housing and bottom housing does not indicate any particular orientation or restrict the scope of the embodiments described to such orientations. Rather it is just a terminology used in relation to the drawings as they are presented. In use, the blower could be orientated such that the top housing 102 is underneath, the bottom housing 103 is on top, or even at any other orientation.

A motor assembly 110 comprising a stator 111, a shaft 112 and a rotor 113 is located in the interior region of the bottom housing 103. The motor assembly 110 could be any suitable motor assembly, such as a brushless DC motor or switched reluctance motor, as two non-limiting examples. Details of motors, their assembly and operation will be known to those skilled in the art and will not be described further here. An impeller 115 is coupled to the shaft 112 and driven by the motor assembly 110 in use.

Figure 5A:
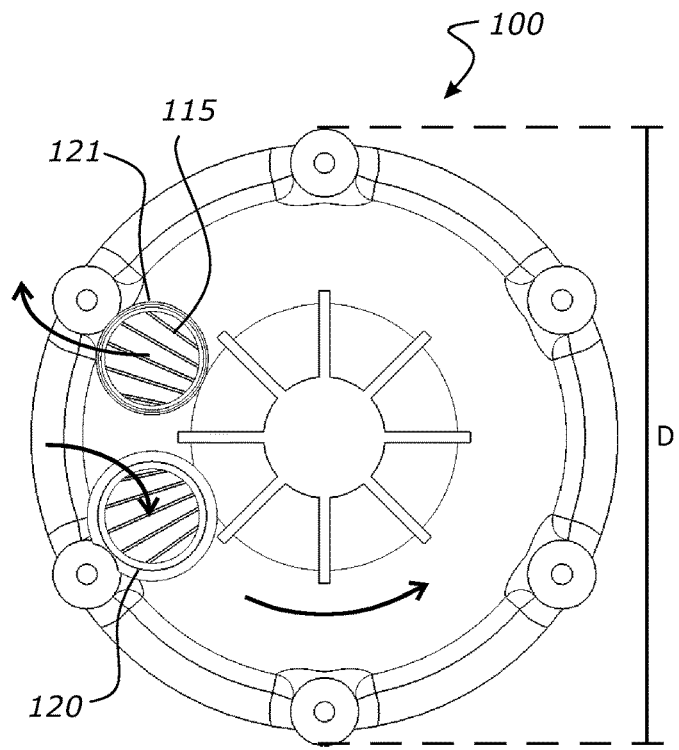
FIGS. 5A and 5B show top views of the regenerative blower.
Figure 5B:
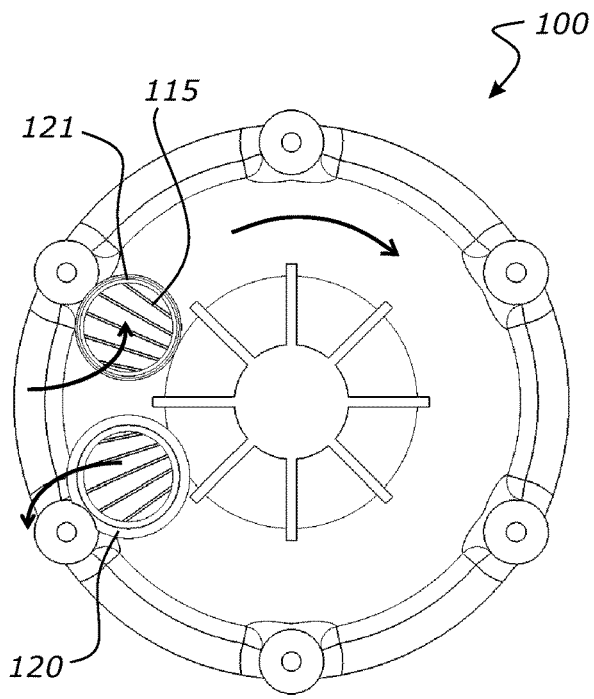
Figure 6:
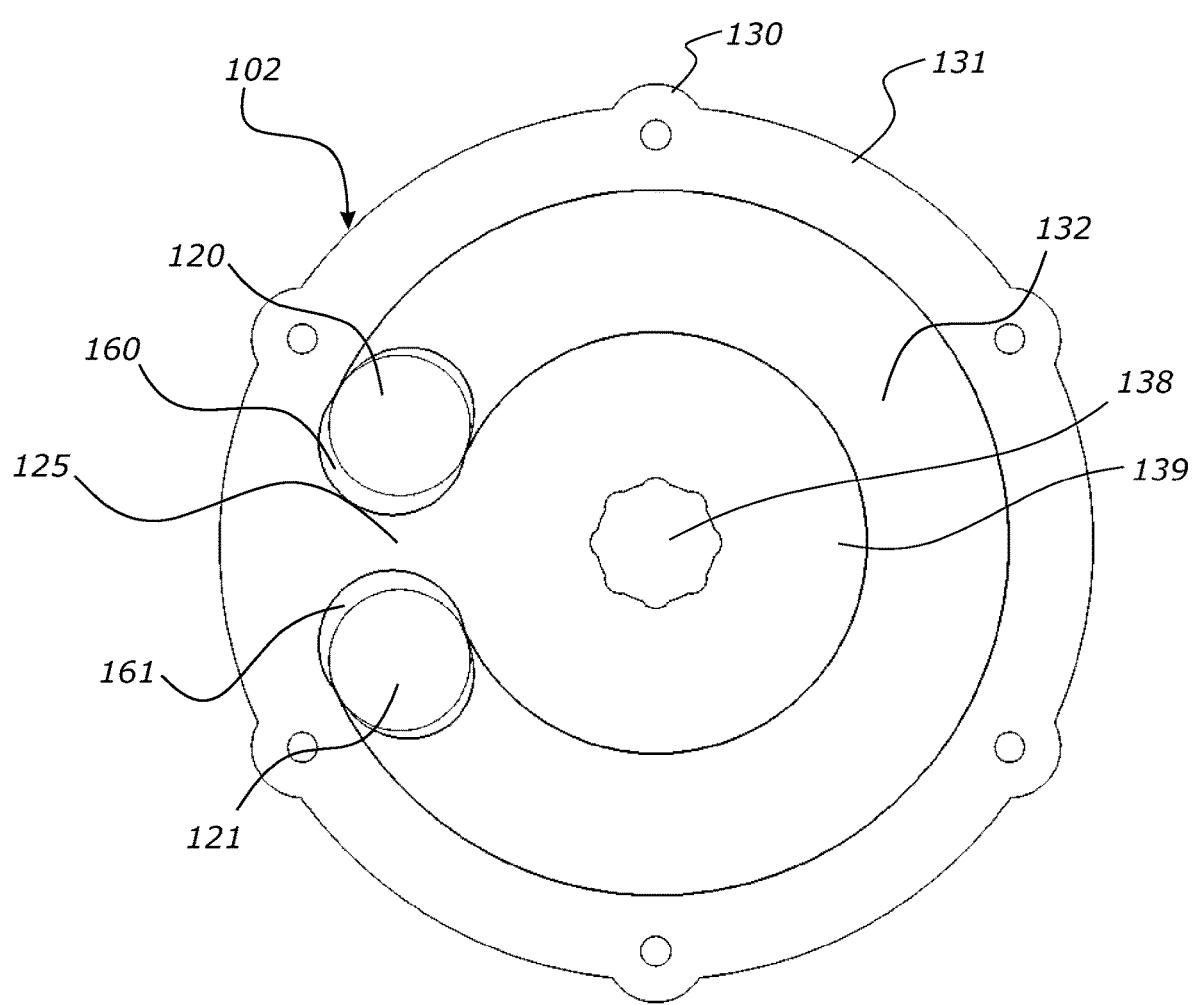
FIG. 6 shows an underside view of a top housing of the regenerative blower.

The impeller 115 is located in the housing 101 and has impeller blades 175 that reside and rotate in the impeller region of the channel 104. An air recirculation path allows the recirculating air to encounter the impeller 115 multiple times on its way from the inlet port to the outlet port. The air continuously cycles through the air recirculation path enabling a successive pressure increase at each pass, producing the regenerative characteristic of the blower. The top housing 102 has a first port 120 and a second port 121, which provide for airflow into and out of the airflow region ("airflow channel") of the channel 104 (and into an out of the impeller channel 145 also). Rotation of the impeller 115 in the impeller channel 145 provides for airflow in the airflow channel between the first 120 and second ports 121 and also provides for airflow in the impeller channel 145. When the impeller 115 rotates anti-clockwise (as shown in FIG. 5A) the first port 120 is an inlet port (more generally "inlet") and the second port 121 is an outlet port (more generally "outlet"), and the air flows into and from the first port 120 to and out of the second port 121. When the impeller 115 rotates clockwise (as shown in FIG. 5B), the second port 121 is an inlet port (more generally "inlet"), and the first port 120 is an outlet port (more generally "outlet") and the air flows into and from the second port to and out of the first port. Without loss of generality, the remainder of the embodiment will be described with the first port as an inlet port and the second port as an outlet port (unless otherwise stated), but it will be appreciated that the alternative configuration is possible, depending on the operation of the blower.

An interrupter 125 (also termed "stripper") separates the outlet port 121 from the inlet port 120 within the housing 101. The interrupter 125 limits (that is, prevents, minimises or at least reduces) airflow from leaking from the outlet (high pressure) to the inlet port (low pressure) during use by providing a physical barrier to the air flow.

The blower according to the first embodiment will now be described in more detail.

2.2.2 Housing

The housing 101 will be described in further detail with reference to FIGS. 6 to 10. The housing comprises a top and bottom housing.

Referring to FIGS. 2, 3A, 4A and 6, the top housing 102 is a generally circular body, with a plurality of lugs (e.g. 130) formed in a perimeter portion 131 to allow for coupling to of the top housing 102 with the bottom housing 103. Alternatively clips, glue, welding or other coupling means could be used. The top housing 102 comprises a top portion 132 of the channel 104 (the other, bottom portion, being in the bottom housing as will be described below). The top portion 132 of the channel 104 provides, or may be in the form of the airflow channel 132. The top portion 132 of the channel 104 may provide, or may be in the form of an arcuate channel 132. As such, the airflow channel 132 may be an arcuate channel 132. The arcuate channel may extend around the generally circular top housing 102 concentrically within a perimeter portion 131 between the first 120 and second port 121. The airflow channel 132 is an upper airflow channel (with respect to those described with reference to FIG. 1), as it is provided above or vertically displaced with respect to the impeller/impeller channel. The arcuate air flow channel 132 is bounded on the inner side by concentric hub or boss 139, with a central aperture 138 that provides a bearing support for bearings connected to the shaft. The (upper) airflow channel 132 is punctuated by the interrupter 125 between the inlet port 120 and the outlet port 121. As such, the airflow channel 132 is not a complete annular channel. Instead, the airflow channel 132 has first and second ends. The airflow channel 132 is therefore arcuate. The airflow channel 132 connects the first and second ports (inlet port/outlet port) at first and second ends of the airflow channel 132. The first port 120 and the second port 121 are in fluid communication with the respective first and second ends of the arcuate channel 132. The interrupter 125 could in some configurations extend past the first and second ports. The interrupter will be described in detail later. The airflow channel 132 has a semi-circular cross-section, and is formed into the top plate or cover of the top housing 102, as is visible in FIG. 3B, for example.

Figure 2:
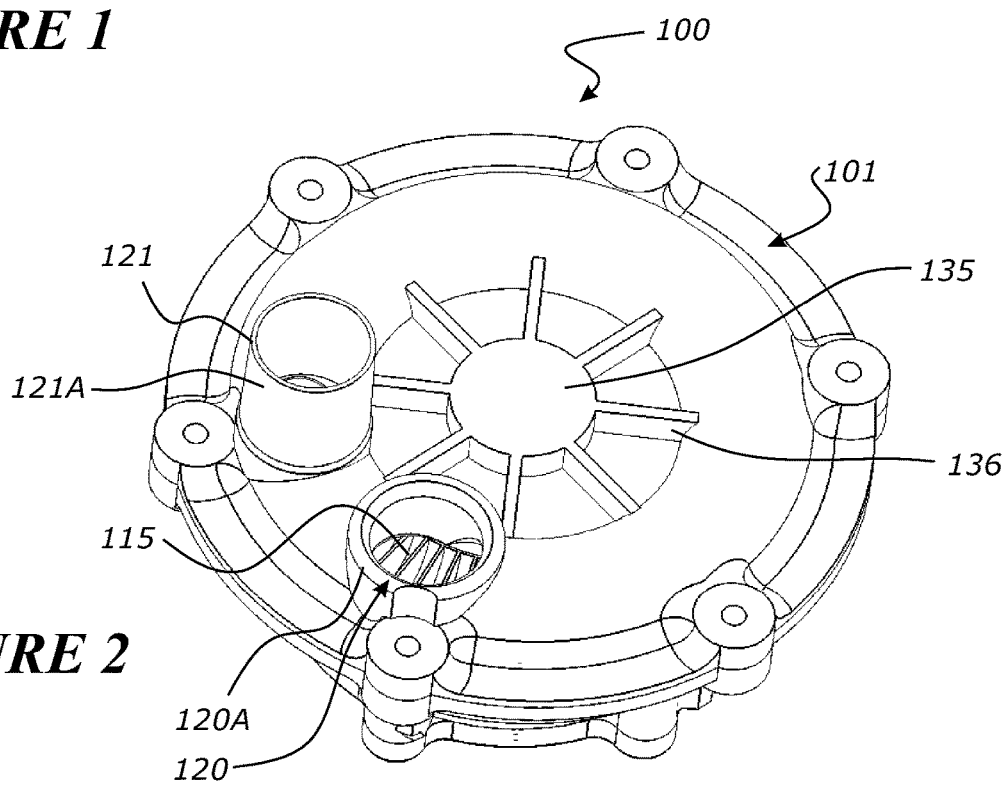
FIG. 2 shows a perspective view of the regenerative blower according to a first embodiment.
Figure 3A:
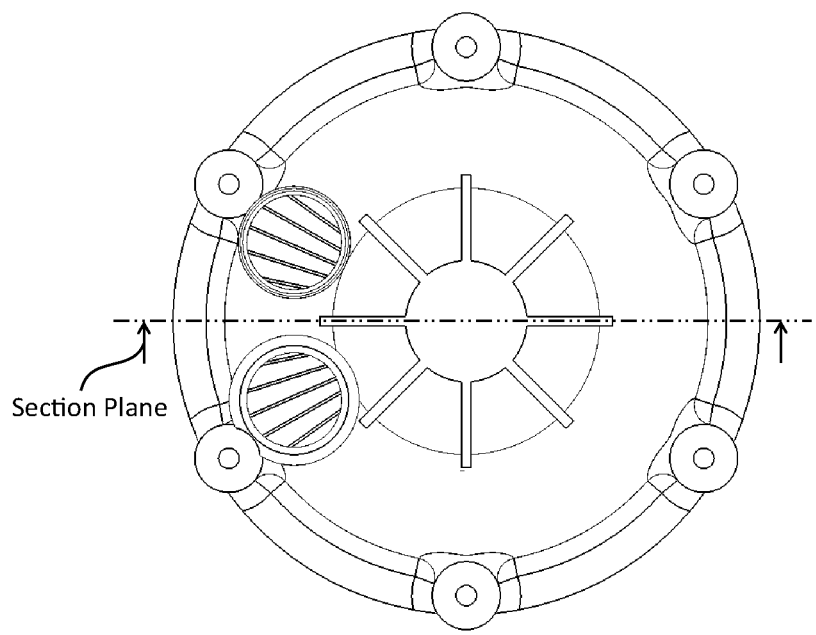
FIGS. 3A and 3B show a top view and cross sectional view of the regenerative blower according to the first embodiment.
Figure 3B:
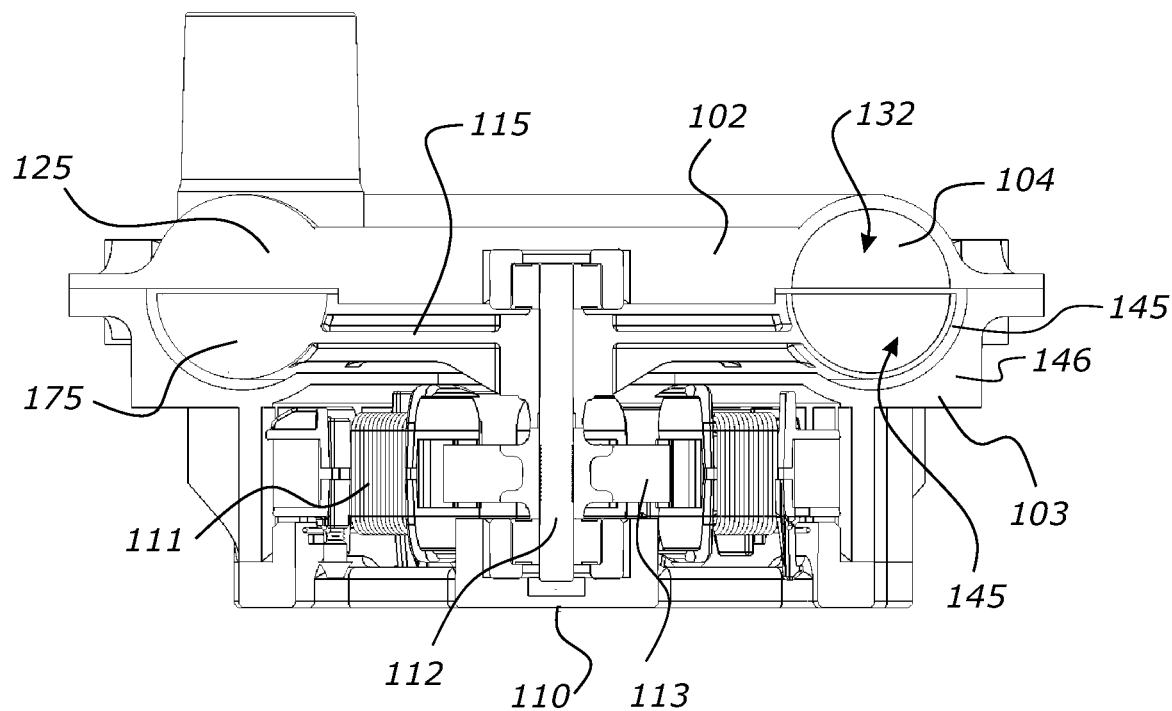
Figure 4A:
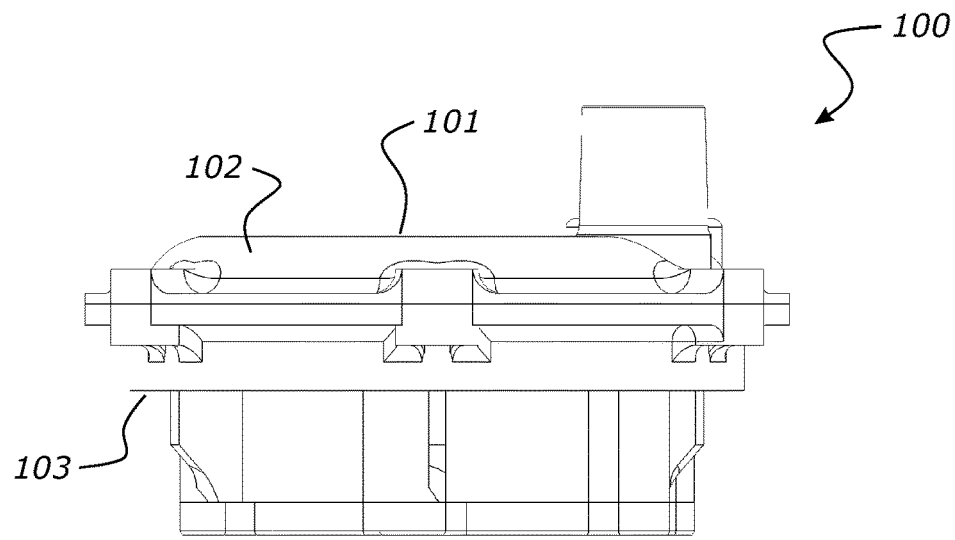
FIGS. 4A and 4B show elevation views of the regenerative blower according to the first embodiment.
Figure 4B:
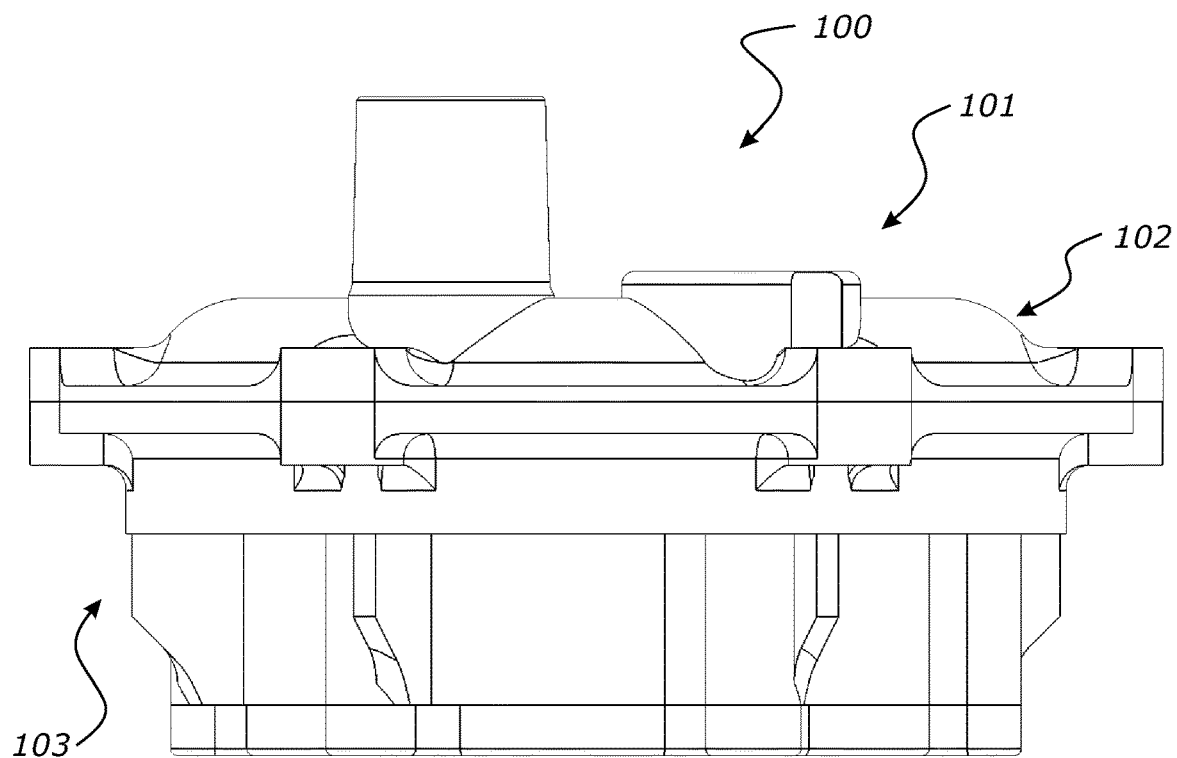

Referring to FIG. 2, for example, an inlet collar 120A extends from the top housing and forms the inlet port 120; and an outlet collar 121A extends from the top housing and forms the outlet port 121. As shown, the inlet and outlet ports 120, 121 are generally parallel with respect to each other, and generally perpendicular to the plane of rotation of the impeller 115, although this is not essential. Other orientations of the inlet/outlet port are possible. The diameter of the inlet port 120 is preferably approximately equal to that of the outlet port 121, although this is not essential. The inlet port 120 and the outlet port 121 are circular, although this is not essential. Alternatively, the inlet port 120 and/or the outlet port 121 can be square, oval, oblong, rectangular or another polygon.

The top housing 102 has a central hub 135 with spokes 136 extending therefrom to the airflow channel 132 to provide structural support. The central hub 135 has a recess on its underside to accommodate the upper bearing arrangement of the motor.

Referring to FIGS. 7, 7A, 8 and 9, the housing 101 comprises a bottom housing cap (casing) 141 (see FIG. 9) configured to be connected to the bottom housing 103. The bottom housing 140 is a generally circular body, with a plurality of lugs 142 formed in a perimeter portion 143 to allow for coupling of the bottom housing 103 with the top housing 102. The bottom housing 140 defines a bottom portion of the channel 104. The bottom portion of the channel 104 provides the impeller channel 145 and is formed in the bottom housing 103 as a (bottom portion) annular channel extending around the generally circular bottom housing 103 concentrically within the perimeter region 143 between the first 120 and second port 121. The impeller channel 145 has a semi-circular cross-section, and is formed into an annular boss 146 (see FIG. 3B) extending from the bottom of the bottom housing 103. The impeller channel 145 is arranged to receive the impeller blades 175 and the impeller blades 175 rotate therein.

Figure 7A:
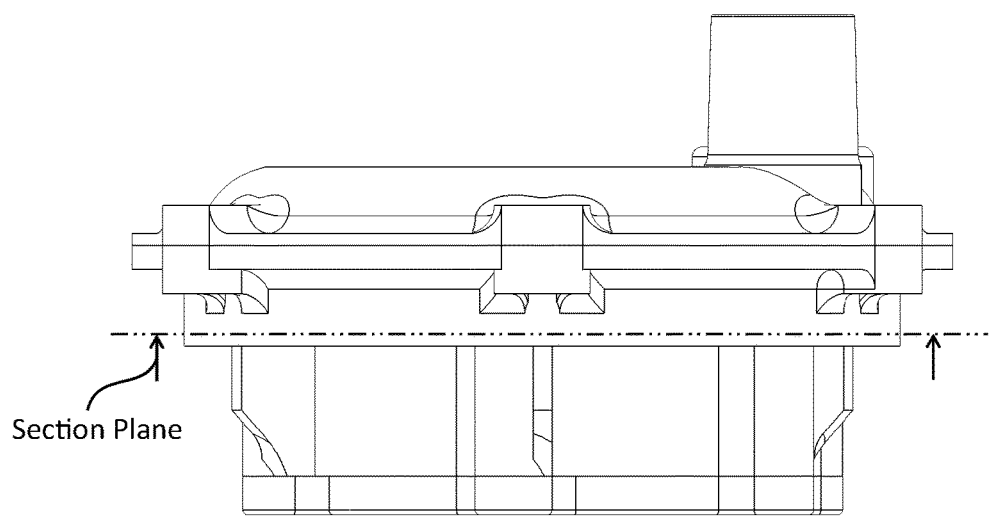
FIGS. 7 and 7A show a side view and cross-sectional perspective bottom view of the regenerative blower.
Figure 8:
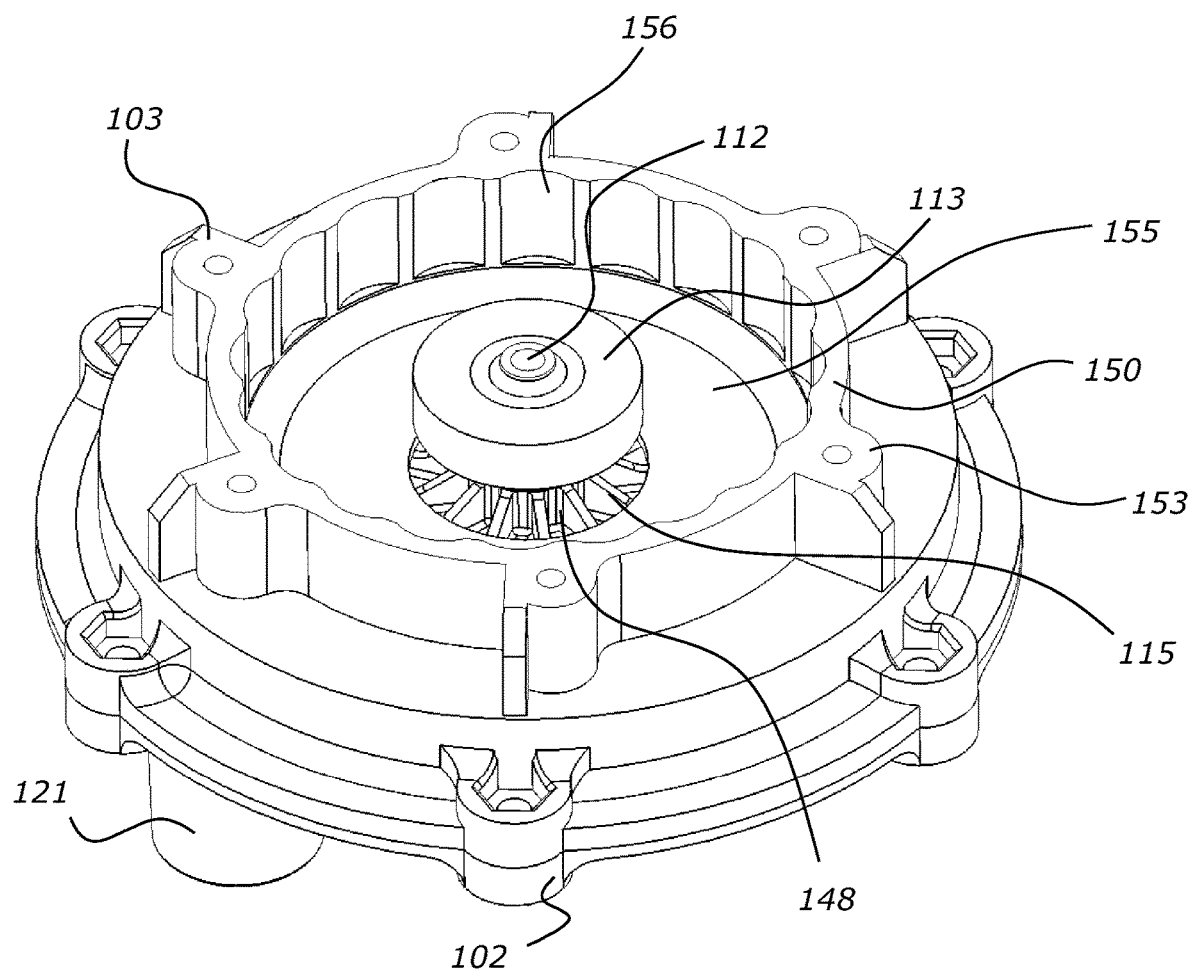
FIG. 8 shows another cross-sectional perspective bottom view of the regenerative blower.

Referring to FIGS. 7A, 8, the bottom housing 103 also comprises a central plate 147 in the inner region with a central aperture 148 (also termed "bottom housing aperture"). The bottom housing aperture 148 is similar in size, or slightly larger in diameter compared to the rotor 113 of the motor assembly. The size is determined by the dimension of the rotor/magnet 113. As one non-limiting example, the bottom housing aperture 148 could be between 15 mm and 25 mm in diameter, for example 21 mm in diameter. The bottom housing aperture 148 can be 15, 16, 17, 18, 19, 20, 21, 22, 23, 24 or 25 mm in diameter. The bottom housing aperture 148 is large enough such that the rotor 113 can fit/pass through it to assist with assembly of the blower 100 during manufacture. This is beneficial in the manufacturing process of the motor. For example, the bottom housing aperture 148 sized in this manner can reduce the cost and/or number of steps involved in manufacturing the blower 100. The assembly process will be described in further detail under the motor description. The bottom housing aperture 148 can also provide an additional airflow path into the blower 100. In addition to the manufacturing benefits, the bottom housing aperture 148 allows improved motor cooling as a result of the additional and/or alternate air flow paths. It can also allow for increased flow rates through the motor as the aperture can act as an additional inlet port for the blower 100.

As the behaviour of the bottom housing aperture 148 is variable, (acting as an inlet when running at high flow, and an outlet when running at high pressure) it can be beneficial to use a one-way valve to control the behaviour of the bottom housing aperture. A plurality of apertures in a bottom housing cap 141 feed the bottom housing aperture 148. The one-way valve would be placed over/blocking the bottom housing cap plurality of apertures, which would in turn act as a one way valve on the bottom housing aperture 148. Examples of a one way valves that can be used include mechanical valves, or fixed-geometry passive valves such as a Tesla Valve. Incorporating the one-way valve improves the performance of the blower in both low flow (high pressure) conditions, as leak through the port is no longer able to occur, and high flow (low pressure) conditions, as the port is able to be used as an inlet to draw in additional air. Similar one-way valve arrangements can also be added to the bottom housing apertures of the other embodiments described herein to improve performance as described.

Figure 7:
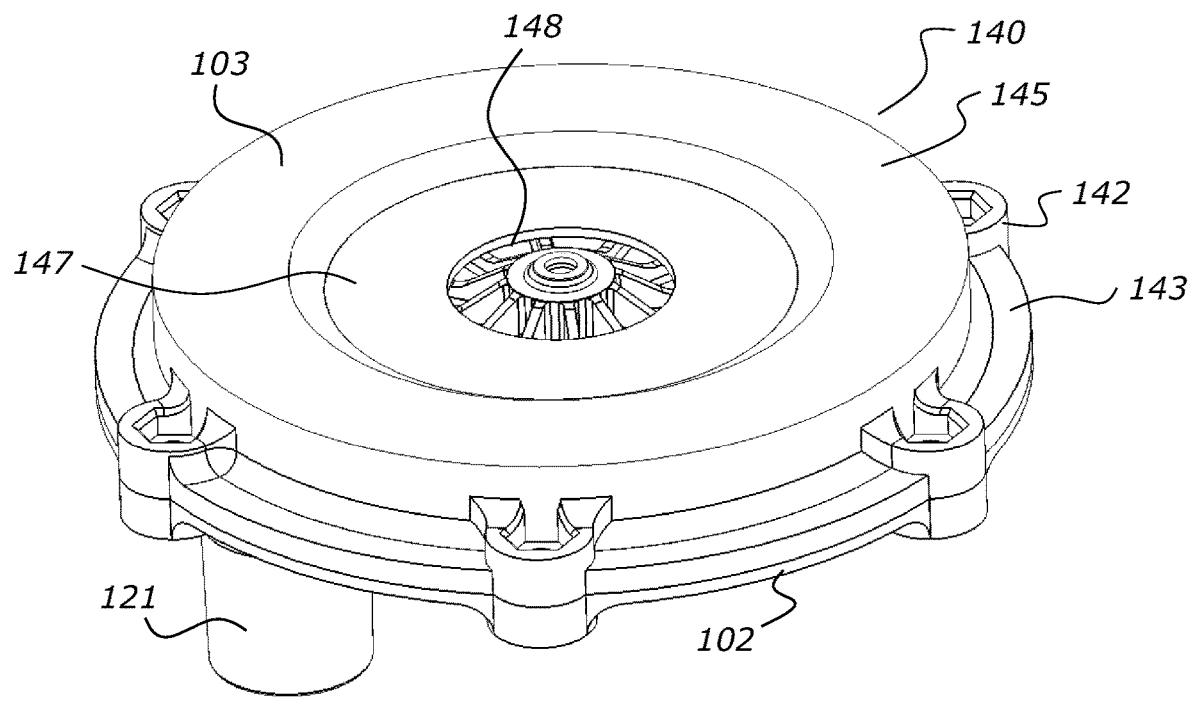
Figure 10:
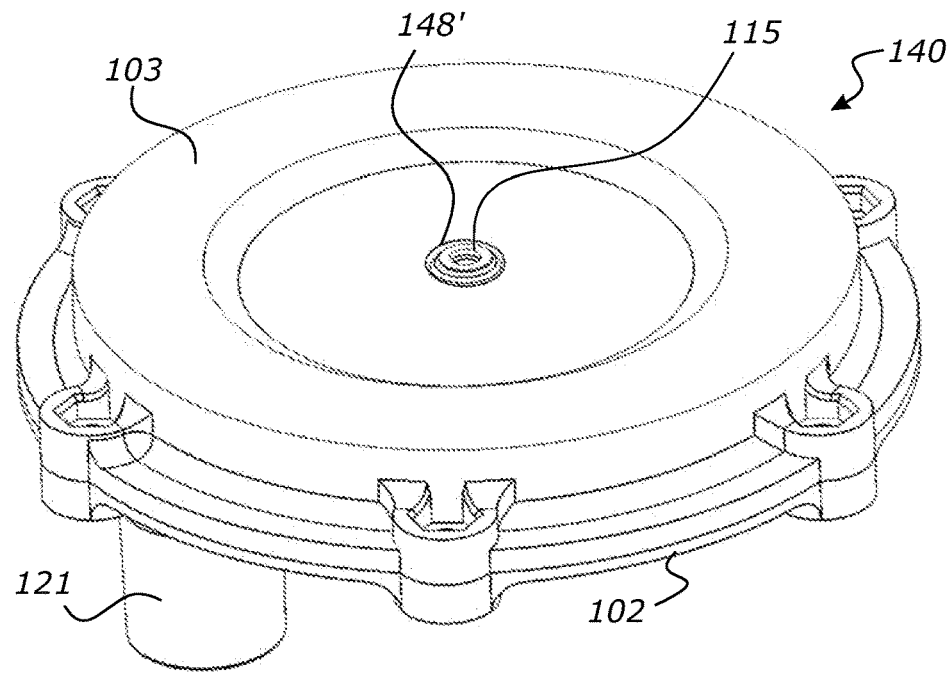
FIG. 10 shows a cross-sectional perspective bottom view of an embodiment of the regenerative blower with a central aperture of a reduced size compared to the regenerative blower of FIG. 7.

FIG. 10 shows an alternative variation the bottom housing 103, in which the bottom housing aperture 148' is smaller than that of the variation of FIGS. 7 and 8. The smaller bottom housing aperture 148' reduces the flow of air that leaks from the aperture 148' when the blower 100 is operated. This can improve the pressure and flow performance of the blower 100 as the amount of air leaking from the bottom housing aperture 148' is minimised.

Figure 9:
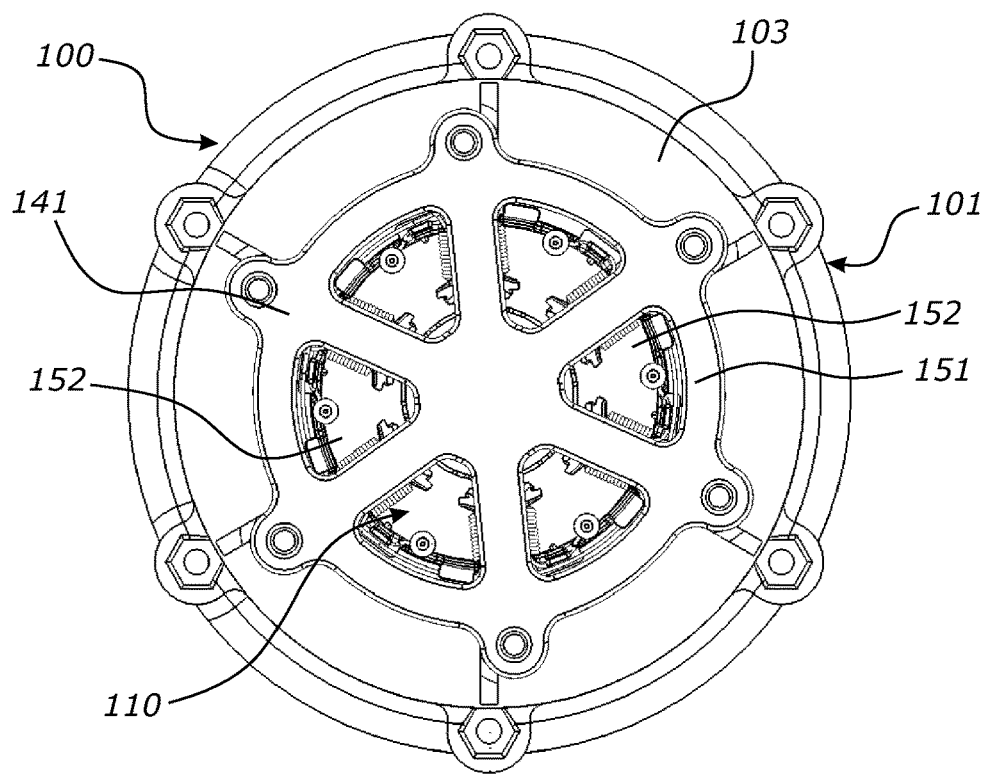
FIG. 9 shows a bottom view of the regenerative blower detailing the lower housing and housing cap.

Referring to FIGS. 8, 9, the bottom housing 103 comprises an annular wall 150. The housing 101 further comprises the bottom housing cap 141. The bottom housing cap 141 includes a plurality of bottom housing cap apertures 152. The annular wall 150 comprises a plurality of lugs 153 extending therefrom for removably coupling the bottom housing cap 141 to the bottom housing 103, via screws, bolts or other fasteners. Alternatively, other coupling means could be used instead of lugs/screw arrangements, for example welding, gluing or use of adhesive bonding techniques. The annular wall 150, when coupled to the bottom housing cap 141, forms an interior region 155 (internal cavity) for housing the motor assembly 110. The bottom housing cap 141 can be removed from the bottom housing 103 to allow access to the internal cavity 155 and/or components such as the motor assembly, which is contained within the internal cavity 155. The bottom housing cap apertures 152 also allow airflow to and from the blower 100 via the bottom housing aperture 148. In combination with the bottom housing aperture 148, the bottom housing cap apertures 152 provides an additional airflow path (port) into the blower 100. In addition, the bottom housing cap apertures 152 allow for improved motor cooling as a result of the additional and/or alternate air flow paths. It can also allow for increased flow rates through the motor as the apertures 152 can act as an additional inlet (via the bottom housing aperture 148) for the blower 100.

The top housing 102, bottom housing 103 and the bottom housing cap 141 are assembled together to form the regenerative blower housing 101. The top housing 102 and bottom housing 103 are retained together with screws, bolts or other suitable fasteners that are located in the corresponding lugs of the top housing 102 and bottom housing 103 that come together in a line. The bottom housing 103 and the bottom housing cap 141 are retained together with screws, bolts or other suitable fasteners. Alternatively, the top housing 102, bottom housing 103 and/or bottom housing cap 141 can be held together by clips, bayonets, press/friction fit, a snap fit arrangement, friction welded connection, ultrasonic welded connection, or any other suitable joining method.

When the top housing 102 and bottom housing 103 are brought together in this manner, the airflow channel 132 and the impeller channel 145 come together to form the channel 104. The impeller channel 145 is arranged to accommodate the impeller 115, and the airflow channel 132 is arranged to allow recirculation, stagnation or regeneration of air displaced by the impeller 115 in use.

2.2.3 Interrupter

During operation, the impeller blades 175 rotate in impeller channel 145 to provide a flow of air through the channel 104 from the inlet port 120 to the outlet port 121. The interrupter 125 is provided between the inlet port 120 and the outlet port 121 to limit airflow in the reverse direction from the outlet port 121 through to the inlet port 120.

Figure 11:
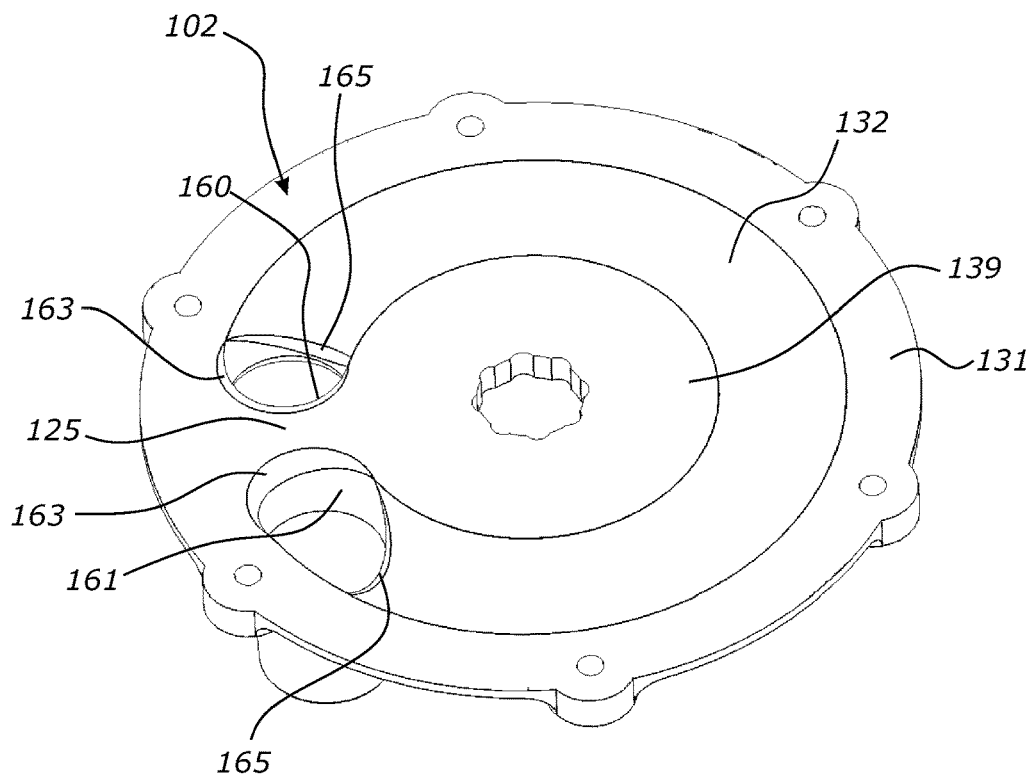
FIGS. 11 to 13 show a bottom perspective view and a bottom view of the top housing of the regenerative blower.
Figure 12:
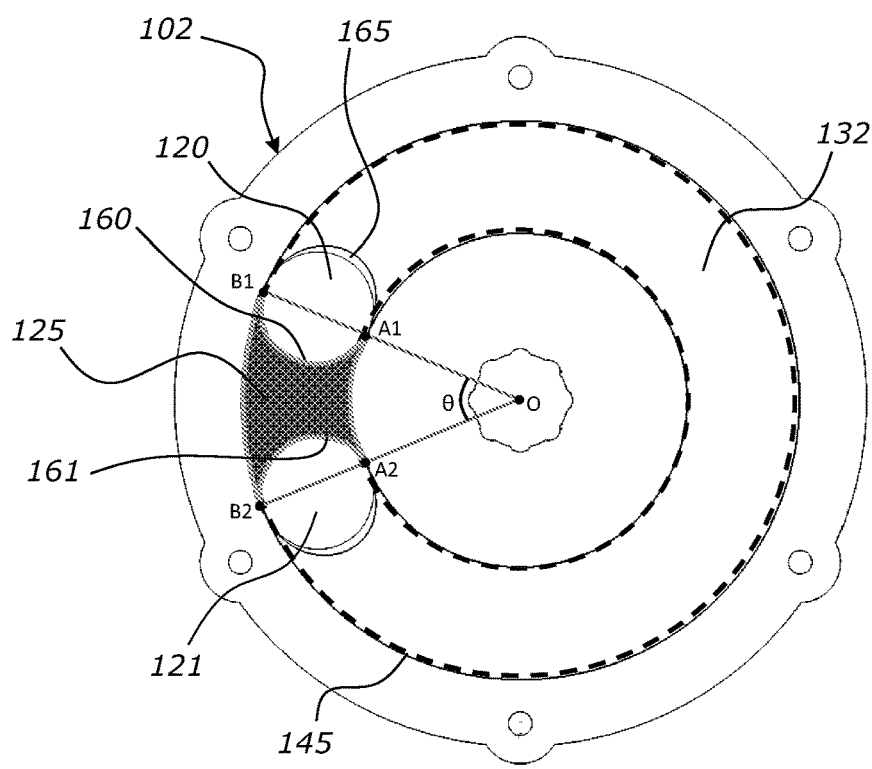
Figure 13:
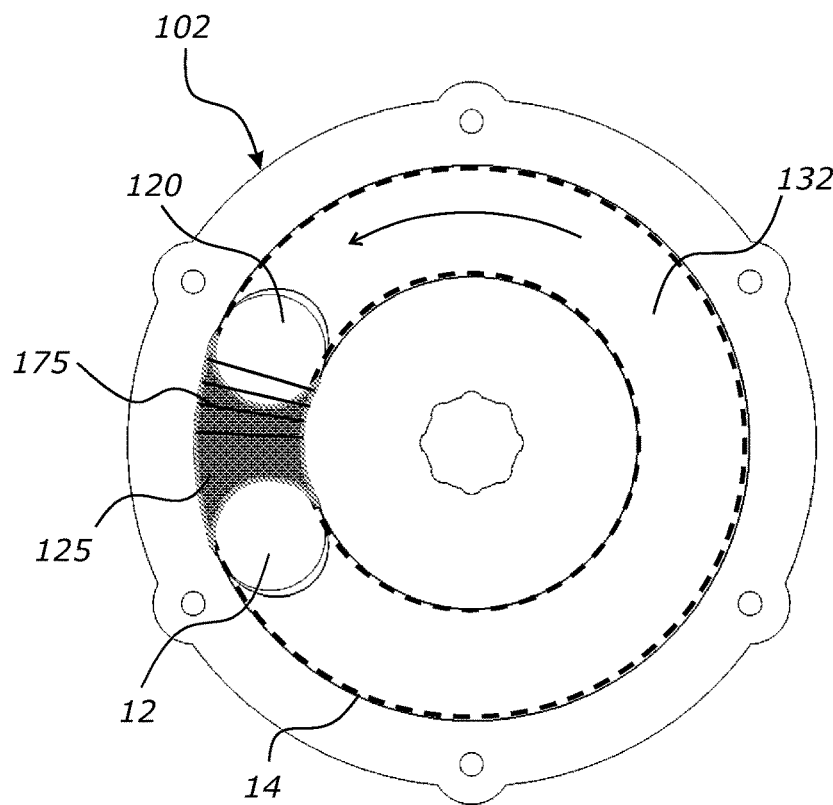
Figure 14:
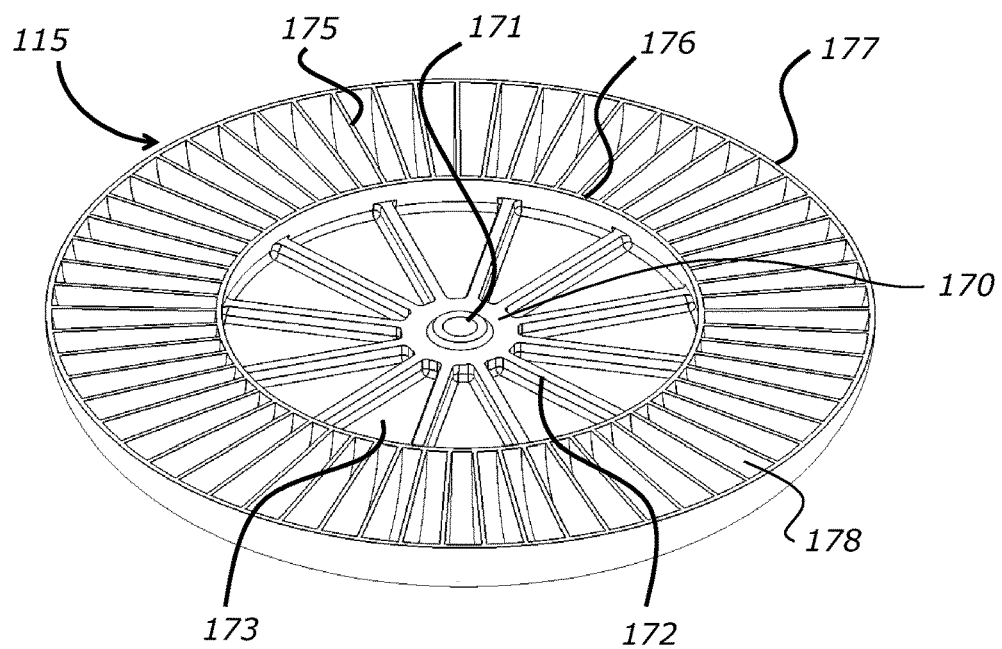
FIG. 14 shows a perspective view of an impeller of a regenerative blower.
Figure 15:
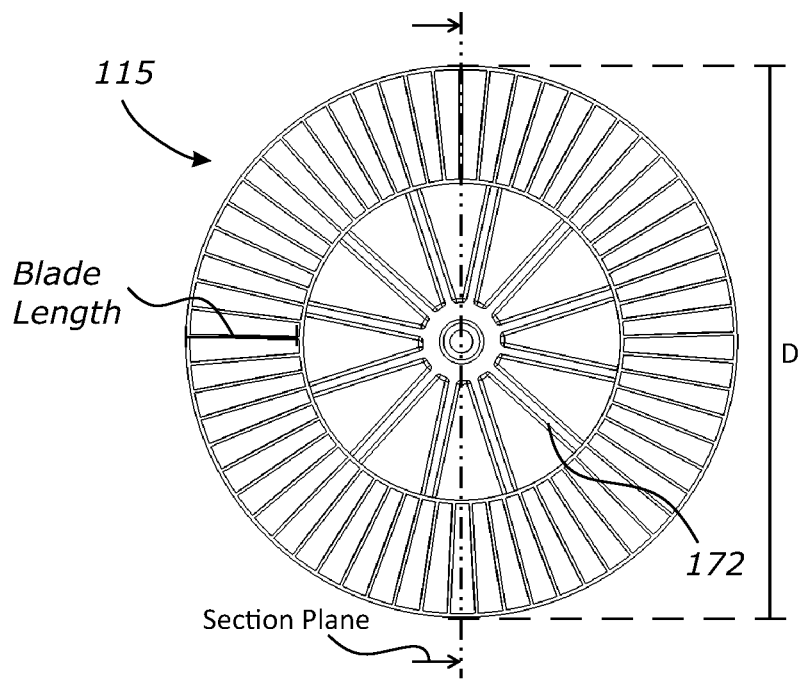
FIG. 15 shows a top view of the impeller of FIG. 14.
Figure 16:
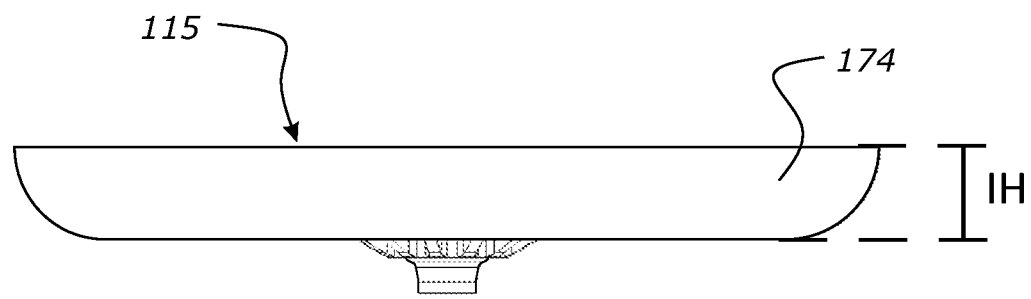
FIG. 16 shows an elevation view of the impeller of FIG. 14.
Figure 17:
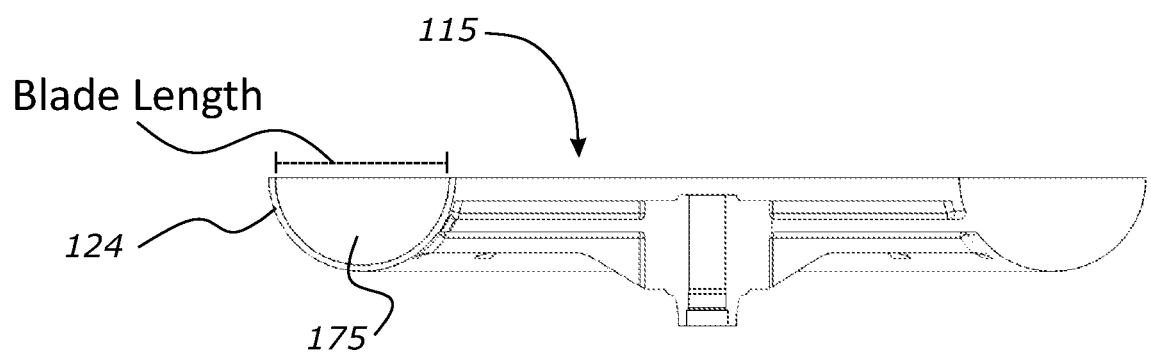
FIG. 17 shows a cross-sectional view of the impeller of FIG. 14.
Figure 18:
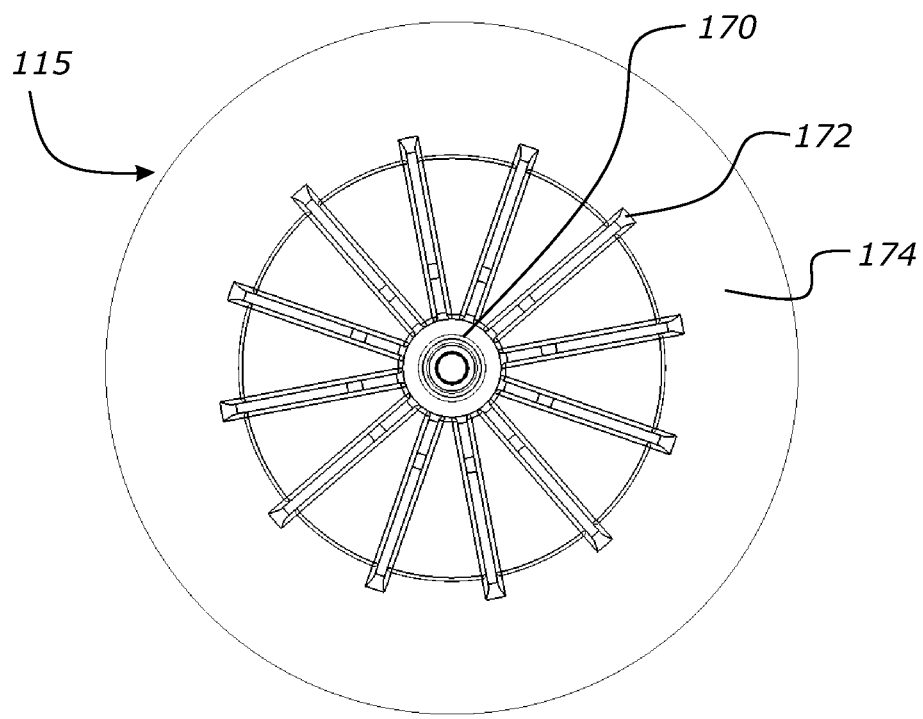
FIG. 18 shows a bottom view of the impeller of FIG. 14.

Referring to FIGS. 11 to 13, which show a bottom view of the top housing 102 of the blower 100 of FIG. 1, the interrupter 125 defines an interrupter effective region (see the shaded portion, FIG. 12) that separates the inlet port 120 from the outlet port 121. The interrupter effective region is a region blocked by the interrupter 125 on the top housing 102 that acts to limit (that is, interrupt or block) airflow from the outlet port 121 to the inlet port 120 when the blower is in use. The interrupter 125 comprises a blocking wall in the top housing 102 between the inlet port 120 and outlet port 121 (where otherwise the airflow channel 132 would be if it continued and became fully annular). The blocking wall comprises a block formed as a bridge that extends between the perimeter portion 131 and the boss 139 of the interior of the top housing 102, between the inlet port 120 and outlet port 121.

The airflow channel 132 slopes upwards around the perimeter of the inlet port 120 and/or the outlet port 121 towards the interrupter 125. The interrupter 125 comprises a leading face 161 and a trailing face 160. The leading face 161 is the face that an impeller blade 175 passes as it encounters the interrupter 125 for the first time during a given rotation. The trailing face 160 is the face that the impeller blade 175 passes as it completes its traversion of the interrupter 125. Each of the inlet port 120 and the outlet port 121 include an interrupter edge 163 and an airflow channel edge 165. The interrupter edge 163 is the edge of the inlet port 120 and/or the outlet port 121 that is adjacent to, and/or forms part of the interrupter 125. In the illustrated configuration, the interrupter edge 163 (shown in FIG. 11) of the outlet port 120 is an edge of the leading face 161 of the interrupter 125. In the illustrated configuration, the interrupter edge 163 of the inlet port is an edge of the trailing face 160 of the interrupter 161. The airflow channel edge 165 of each of the inlet port 120 and the outlet port 121 is the edge of each respective port that is adjacent to, or forms part of the boundary of the airflow channel 132 of the top housing 102. In the illustrated configuration, each interrupter edge 163 and airflow channel edge 165 are rounded. The rounded edges help reduce the blade pass noise as the impeller 115 rotates past (transits) the inlet port 120 and outlet port 121. In alternatives, each interrupter edge 162 and airflow channel edge 165 can be non-rounded or square edge, or be a chamfered edge, if different behaviours are desired. For example, sharper edges result in better pressure and flow performance, and are better for power consumption, and so can be used where noise isn't a large concern.

2.2.4 Motor

The bottom housing aperture 148 is large enough that the rotor 113 can fit through it. This is beneficial in the manufacturing process of the motor. The impeller 115 and rotor 113 can be attached to the shaft 112, and then the combined impeller/shaft/rotor part can then be fit through the bottom housing aperture 148. The side of the shaft 112 with the rotor 113 is moved through the bottom housing aperture 148 so that the rotor 113 is on the bottom side of the bottom housing 103, and the impeller 115 fits within the impeller channel 145 of the bottom housing. This can reduce the cost and/or number of steps involved in manufacturing the blower 100.

2.2.5 Impeller

As described above, the impeller 115 sits in the impeller channel 145 (bottom portion of the channel 104) and rotates therein. FIGS. 14 to 18 show a possible embodiment of the impeller 115. The impeller comprises a central hub 170 with an aperture 171 for supporting the impeller 115 on the shaft 112 extending from the motor 110. A plurality of spokes 172 supported on a central support plate 173 extend from the hub 170 to the inner side of an annular impeller blade support channel 174 that supports impeller blades 175. The support channel has a semi-circular cross-section and as such takes the form of a hollow, bottom portion of a torus. Impeller blades 175 are located in the support channel 174 extending from the inner side to the outer side of the support channel 174. The blades 175 are semi-circular in shape matching the cross-section of the support channel 174, with a straight top edge, and a semi-circular bottom edge that fits in the support channel 174. Pockets 178 are formed between each impeller blade 175. Alternatively, in other configurations, the support channel 174 and/or blades 175 can take a different cross-section such as semi-oval, rectangular or another shape/polygon. The impeller 115 can have any suitable number of blades, preferably an odd number, and more preferably a prime number to reduce blade pass noise, harmonics, resonances and/or other vibrations. As a non-limiting example, the number of blades could be selected from prime numbers 47, 53, 59, 61, 67, 71, 73, 79 or numbers either side of those, e.g. 46, 48, 52, 54, 58, 60, 63, 66, 68, 70, 72, 74, 78, 80. The impeller 115 is shown in the figures according this embodiment has 61 blades, as an example. The blades 175 are uniformly distributed around the impeller 115 at between about 7.7° (47 blades) and 4.55° (79 blades) (such as equal to or about 5.9° (61 blades)) away from each other with respect to angles taken from the centre of the impeller 115. Other numbers of blades and angular distribution are possible also. The relationship between the number of impeller blades and the angle between each adjacent pair of impeller blades can be of the form:

$$\theta = \frac{360}{N} \text{ degrees, or}$$

$$\theta = \frac{2\pi}{N} \text{ radians}$$

Where θ is the angle between respective impeller blades (in degrees or radians depending on the formula used) and N is the number of impeller blades.

The impeller blades 175 as shown extend radially along lines from the centre of the impeller 115. In other configurations, the impeller blades 175 could be angled with respect to a radial line (when viewed from the top and/or side), could be curved, swept or serpentine, for example. The impeller blades 175 could also be angled with respect to the vertical. For example, the bottom of each impeller blade 175 (where it connects to the support channel 174) could be offset from the top of the impeller blade 175. The spokes 172 help provide rigidity and strength to the impeller 115.

In this and the subsequent embodiments, the impeller 115 is constructed to be lightweight. For example, a lightweight material can be used. Also, thin blades with minimal material and large gaps between blades could be implemented to reduce weight. A lightweight impeller provides benefits such as manufacturing cost, low rotational inertia and is balanced or requires little effort to rotationally balance once manufactured. An impeller with low rotational inertia can be quickly accelerated and decelerated. A lightweight impeller is therefore suited for quickly responding to fluctuating pressure requirements, such as the normal inhalation and exhalation cycle of a patient connected to the breathing assistance device in which the impeller operates.

2.2.6 Operation

The blower 100 can be used in a gas flow apparatus, such as one of those described previously, to effect the operations of the gas flow apparatus 600. In at least one form, the respiration apparatus 600 can be a breathing assistance apparatus 600. A controller is used to control operation of the blower 100, and in particular to control provision of power to the motor and operation of the motor (more generally, "energise" the motor). Referring to FIGS. 2, 5A, 5B, in one configuration, the regenerative blower 100 is operated by the controller to blow in a single direction. The controller provides power and control to rotate the motor, which in turn rotates the impeller 115 within the impeller channel 145, drawing air in through the inlet port 120 and blowing the air out through the outlet port 121.

In another configuration, the regenerative blower 100 can be configured to rotate the impeller 115 in both of a first direction of rotation and an opposite or second direction of rotation (i.e. to function as a dual outlet, bi-directional or reversible blower). The controller energises the motor to rotate the impeller 115 in a first direction of rotation to generate a flow of gases to exit the outlet port of the housing. Energizing the motor to rotate the impeller 115 in an opposite second direction of rotation generates a flow of gases to exit what was formerly the inlet port, and is now the outlet port of the housing, drawing air through what was formerly the outlet port, and is now the inlet port. So as opposed to strictly having an inlet port and an outlet port, the bi-directional blower can be said to have a first port and a second port, where the first port is the inlet when blowing in the first direction, and the second port is the inlet when blowing in the second direction. FIG. 13 shows the blower with a reversed direction.

Cycling the direction of rotation of the impeller 115 allows rapid alternation between positive pressure and negative pressure at one of the ports of the blower 100. A rapidly reversible blower can be useful in applications including simulating lungs, or providing ventilation to patients with breathing difficulties. This effect can be performed best when a lightweight and/or low inertia impeller is used, such as that previously described (or also, build according to principles such as those described in WO2013009193, which is incorporated herein by reference in its entirety) because the moment of inertia is minimised for a lightweight impeller. A lightweight and/or low inertia impeller reduces the energy consumption of the motor configured to rapidly change directions to change the direction of flow.

In a third configuration, the regenerative blower can be configured as a suction generating device. Such a suction generating device could be used as part of a suction system, or a system configured to provide suction. The regenerative blower will be arranged to generate suction or a partial vacuum at the inlet, and connected tubing. This allows the blower to be used as a gas evacuation or gas removal device.

2.2.7 Example Dimensions for First Embodiment

Exemplary, non-limiting, examples of dimensions of the first embodiment will be detailed below.

Referring to FIG. 5A, the regenerative blower housing has a diameter D (including the lugs), which could be any suitable dimension for the housing to be assembled with the other features described and achieve the operating functions as described herein. In one, non-limiting example, the diameter D of the regenerative blower is between about 80 mm and 110 mm and for example equal to or about 90.4 mm.

FIG. 12 shows a possible angular configuration of the interrupter 125 with respect to the centre of the top housing 102. In one, non-limiting, example.

Angle θ is between about 45° and 55°, such as approximately 49.22° or approximately 45.4°.

An arc length A between A1 and A2 is approximately is between about 16 mm and 22 mm, such as approximately 17.83 mm.

An arc length B between B1 and B2 is between about 27 mm and 34 mm, such as approximately 29.85 mm.

A ratio between A:B is therefore between about 1:2.13 and 1:1.22, and can be 17.83:29.85, or approximately 1:1.67.

Referring to FIGS. 14 to 18, the impeller blades 175 are uniformly distributed around the impeller 115 at between about 7.7° (47 blades) and 4.55° (79 blades) (such as equal to or about 5.9°) away from each other with respect to angles taken from the centre of the impeller 115. The impeller 115 has a diameter D, a blade length BL and a height IH, which could be any suitable length to achieve the operating functions as described herein. As a non-limiting example, the impeller's diameter in one configuration could be between about 50 mm to 90 mm, such as equal to or about 70.5 mm. In at least one configuration, the impeller 115 can have a blade length between about 10 mm to 20 mm, such as equal to or about 14 mm. In at least one configuration, the impeller 115 can have an impeller height between about 5 mm to 10 mm, such as equal to or about 7.5 mm. Again, as a non-limiting example, blade surface area could be between about 50 mm2 to 100 mm2, such as equal to or about 76.95 mm2. In a non-limiting example, the impeller 115 can be made from plastic such as ABS plastic, or other material resulting in a relatively lightweight impeller with a low moment of inertia. As an example, an impeller made from ABS plastic or similar to the dimensions above weighs between about 3 g and 12 g, such as equal to or about 6.7 g if made from ABS plastic, or 8 g if made from 3D printed material (e.g. a photopolymer resin).

2.3 Second Embodiment of a Regenerative Blower

FIGS. 19 to 32 show a regenerative blower according to a second embodiment. Features of the second embodiment that are the same or similar to those of the first embodiment may not be described fully or at all, but it will be appreciated by those skilled in the art that relevant portions of the description relating the first embodiment or any other embodiments described herein apply to this embodiment, where appropriate.

2.3.1 Overview

Figure 19:
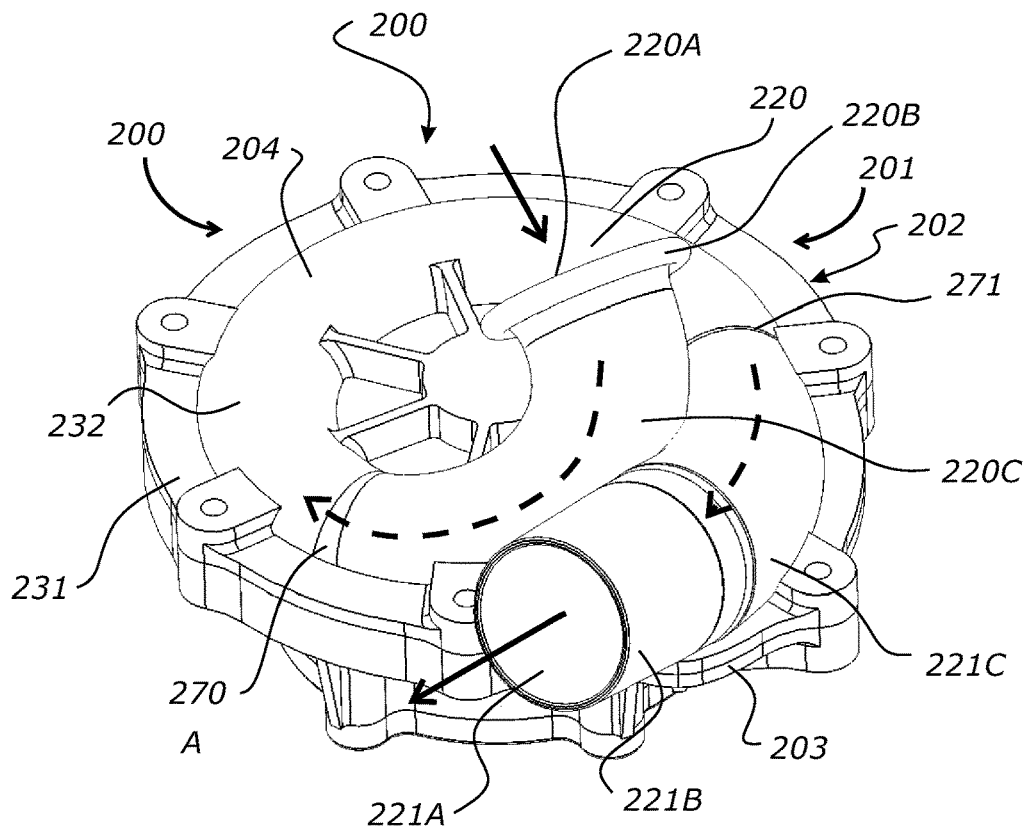
FIGS. 19 to 25 show perspective, top and elevation views of a regenerative blower according to a first configuration of a second embodiment.
Figure 20:
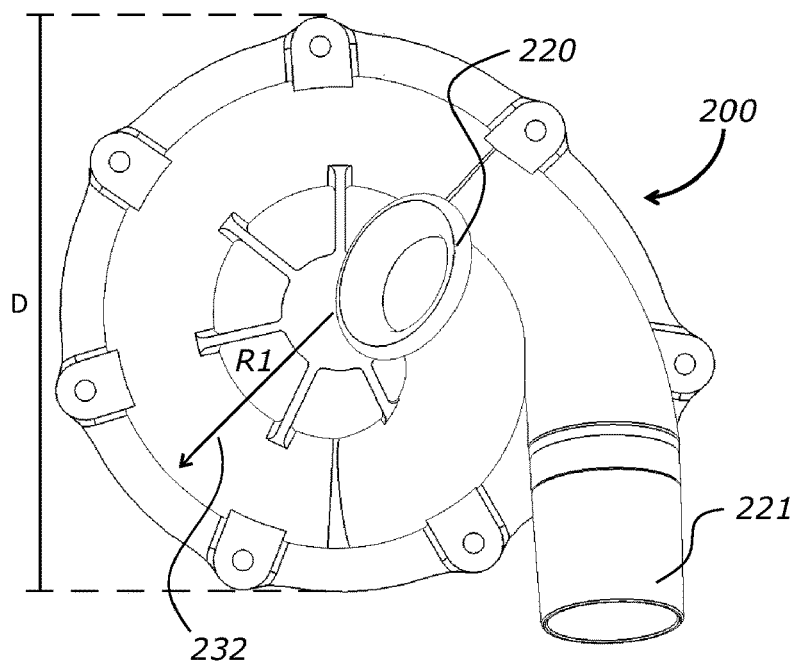
Figure 21:
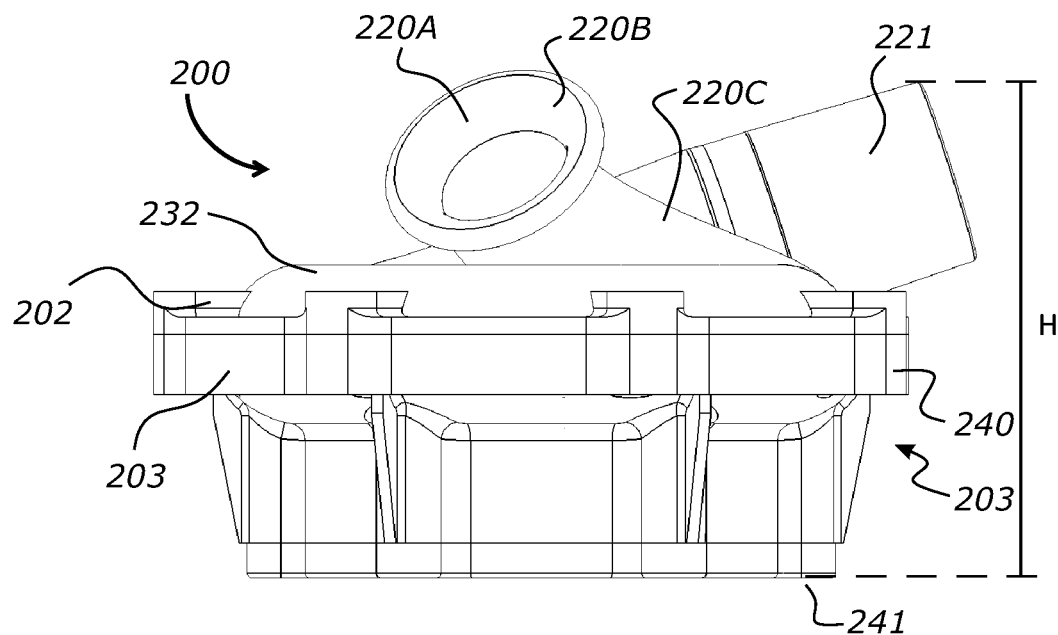

Referring to FIG. 19, the regenerative blower 200 of the second embodiment, like the first embodiment, comprises a housing 201 with a top housing 202 and a bottom housing 203. The housing 201 comprises first 220 and second 221 ports for an inlet and an outlet, a channel 204, an interrupter 225, and a motor assembly 210 including a stator 211, a rotor 213, a shaft 211, and an impeller 215 coupled to the motor 210. The impeller 215 can be that described previously in relation to the first embodiment.

Features the blower according to the second embodiment that may not have been described in relation to other embodiments will now be described in more detail.

2.3.2 Housing—Configuration #1

Like the other embodiments, the blower housing 201 comprises a top housing 202, a bottom housing 203 and a bottom housing cap 241.

In a first configuration of the second embodiment (shown in FIGS. 19-28), the top housing 202 provides a different configuration (compared to the first embodiment) of first 220 and second 221 ports (inlet port and outlet port). The inlet port 220 comprises an aperture 220A, an inlet collar 220B and inlet conduit 220C. The inlet aperture 220A and inlet collar 220B are arranged proximate the centre of the top housing 202, with the inlet aperture 220A inclined at an angle to face away from the top housing 202. The inlet collar 220B and an inlet aperture 220A are spaced vertically away from the top housing 202. The inlet collar 220B extends into the inlet conduit 220C that curves around and down in an at least partially helical/spiral (partial turn) manner to join and integrally form into an airflow channel 232 of the top housing 202 at a nominal inlet juncture 270 between the two. To achieve this, the inlet port 220 inclines at an angle other than perpendicular relative to the plane of the airflow channel 232 and extends along a curve that continues from a curve of the airflow channel 232, wherein the plane is the plane of the airflow channel 232, and the airflow channel is an upper channel, such as shown in the generic embodiment of FIG. 1. It should be noted that there is not necessarily any physical junction (although optionally there might be a physical junction) but rather this is just the nominal junction where the conduit 220C is deemed to have become the airflow channel 232. The inlet collar 220B, aperture 220A and conduit 220C form the inlet port 220. The airflow channel 232 curves around concentrically within a perimeter portion 231 of the top housing and then integrally extends and forms into the outlet port 221. The outlet port 221 comprises an outlet conduit 221C with an outlet collar 221B and outlet aperture 221A. The airflow channel 232 meets the outlet conduit 221C at a nominal outlet juncture 271. It should be noted that there is not necessarily any physical junction (although optionally there might be a physical junction) but rather this is just the nominal junction where the conduit 221C is deemed to have become into the airflow channel 232. The outlet conduit 221C, collar 221B and aperture 221A are configured and arranged to extend in a partially helical manner and tangentially from the airflow channel. The outlet port 221 extends at an angle other than perpendicular relative to the plane of the arcuate airflow channel 232. In this arrangement the inlet and outlet ports 220, 221 form a spiral (or partial spiral, such as a partial helix) with the airflow channel 232. The spiral can be constant or variable pitch and radius.

This configuration introduces air tangentially or at least partially tangentially into the channel 204 at approximately point "A" (after curving through a partially helical flow path and the inlet conduit 220C), directing the air across the impeller 225 disposed in an impeller blade region ("impeller channel") of the channel 204. The configuration also provides for an outlet airflow from the blower 200 in a tangential, substantially tangential or at least partially tangential direction with respect to the impeller rotation. The first and second port configuration reduces internal resistances to flow within the blower 200, improving performance. This can allow better pressure and flow performance to be achieved compared to a regenerative blower with a similarly sized impeller, but an inlet port oriented perpendicular to the direction of impeller rotation, and an outlet oriented perpendicular to the direction of impeller rotation.

Figure 26:
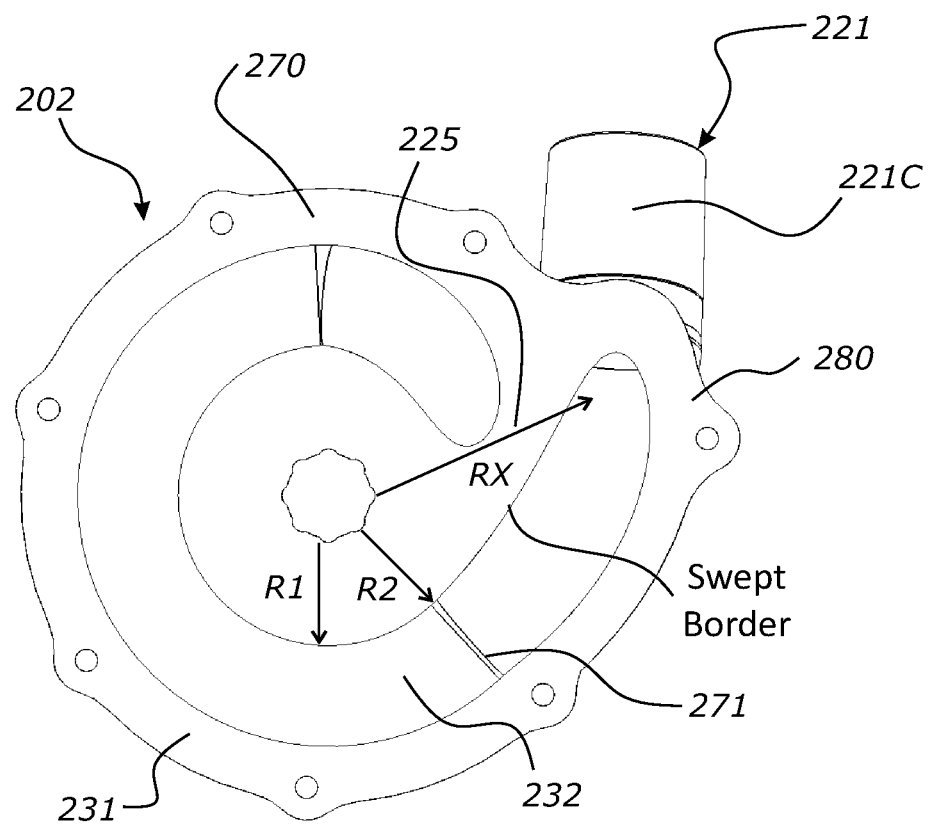
FIGS. 26 to 28 show a bottom view of a housing of the regenerative blower according to the first configuration of the second embodiment detailing an interrupter and airflow channel according to the first configuration.

In this embodiment 200, the channel 204 of the housing 201 has a different configuration to that previously described for first embodiment, as is apparent from the configuration of the top housing 202 and the airflow channel 232 formed in the top housing 202. Referring to FIG. 26, the top housing 202 is not circular, but rather has an eccentric portion 280 protruding from the nominal circular perimeter 231. The airflow channel 232 has one end at the nominal inlet juncture 270 where the inlet conduit 220C integrally forms with the airflow channel 232, and the airflow channel 232 extends in a generally circular manner with a radius R1 in the top housing 202 concentrically within the perimeter portion 231 until it reaches the nominal outlet juncture 271 where the outlet conduit 221C integrally meets with the airflow channel 232. From there, the airflow channel 232 continues to follow in a curved but increasingly larger radius (R2 to Rx) path on the inside of the perimeter 231 into the eccentric portion 280 of the top housing 202. This results in an airflow channel 232 and outlet port 221 which has an at least partial spiral formation. The airflow channel 232 may be considered to terminate at the nominal juncture 271, after which point the airflow channel 232 becomes part of the outlet conduit 221C. The airflow channel 232 has a semi-circular cross section that is formed into the top cover of the top housing 202 (see, e.g. FIG. 19). The airflow channel 232 is punctuated by the interrupter 225 between the inlet port 220 and the outlet port 221. As such, the airflow channel 232 is not complete annular channel. The interrupter 225 will be described in detail later.

The bottom housing 203 at least partially defines an impeller channel 245 similar to the impeller channel 145 described with reference to blower 100. The impeller channel 245 is circular, the same as the first embodiment, and the impeller 215 rotates therein. An air recirculation path allows the recirculating air to encounter the impeller 215 multiple times on its way from the inlet port 220 to the outlet port 221. The air cycles through the air recirculation path enabling a successive pressure increase at each impeller pass, producing the regenerative characteristic of the blower 200.

2.3.3 Interrupter—Configuration #1

Figure 27:
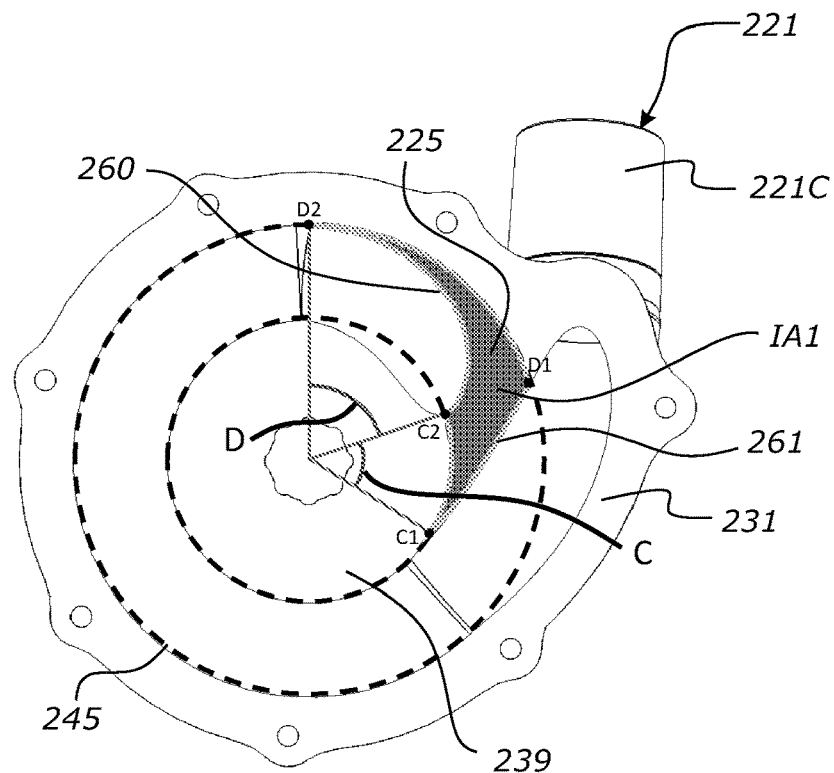

The interrupter 225 (providing the grey interrupter region of FIGS. 27 and 28) of the second embodiment differs from the first embodiment and will be described with reference to FIGS. 27, 28. The interrupter is swept, with a shorter arc length on the leading face 261 in the airflow channel 232 and a longer arc length on the trailing face 260 in the airflow channel 232. This configuration of the interrupter 225 provides a leading face 261 and a trailing face 260 which are non-square to the impeller blades. That is the leading face 261 and the trailing face 260 (and the edges thereof) are orientated and/or shaped to present at an angle to the impeller blades when they rotate.

In the first configuration of the second embodiment interrupter 225 (shown in FIGS. 27 and 28), the interrupter 225 comprises a blocking wall on the top housing 202 between the inlet port 220 and the outlet port 221. The blocking wall is in the form of a bridge between a hub 239 and the perimeter portion 231. The interrupter 225 comprises a leading face 261 adjacent/interfacing with the outlet conduit 221C (the leading face 261) and forms a wall of at least some of the outlet conduit 221C on the top housing 202. The leading face 261 is concave curved as per the concave surface of the outlet conduit 221C. The leading face 261 can be in the form of a swept leading face. The leading face 261 can be swept when viewed from bottom of the interrupter 225 as shown in FIG. 27. The leading face 261 can comprise a leading edge. The leading face 261 extends from point C1 to point D1 across the airflow channel 232 of the top housing 202, such that the leading face 261 blocks the airflow channel 232 to limit airflow going directly from the outlet port 221 to the inlet port 220. The leading face 261 sweeps across an angle C formed between the radius line between the central aperture and C1 and the radius line between the central aperture and D1 (which is also on other same radius line as C2). The sweep of the leading face 261 can be any suitable configuration or shape, such as straight, curved or the like. The angle C can be anything such that the leading face 261 may take any configuration from between radial to tangential, depending on the required configuration and the configuration of the outlet conduit.

The interrupter 225 also has a trailing face 260 adjacent/interfacing the inlet conduit 220C and forms a wall of at least some of the inlet conduit 220C on the top housing 202. The trailing face 260 is concave curved as per the concave surface of the inlet conduit 220C. The trailing face 260 can be swept when viewed from bottom of the interrupter 225. The trailing face 260 extends from point C2 to point D2 across the airflow channel 232 of the top housing 202, such that the interrupter 225 blocks the airflow channel 232 to limit airflow going directly from the outlet port 221 to the inlet port 220. The trailing face 260 sweeps across an angle D formed between the radius line between the central aperture and C2 and the radius line between the central aperture and D2. The sweep of trailing face 260 can be any suitable configuration or shape. The angle D can be anything such that the swept edge may take any configurations from between radial to tangential, depending on the required configuration and the configuration of the inlet conduit 220C.

In this configuration, the arc length between point C1 and point C2 is less than the arc length between point D1 and point D2. Furthermore, point D1 is displaced counter-clockwise from a radial line passing through the origin and C1 (when the top housing is viewed from below as shown in FIG. 27). The angle C formed between the centre of the impeller's axis of rotation and the points C1 and C2 (angle C) is less than the corresponding angle formed between D1 and D2 (angle D). These design features lead to the "swept" interrupter profile, where the leading and trailing edges are "swept".

Figure 28:
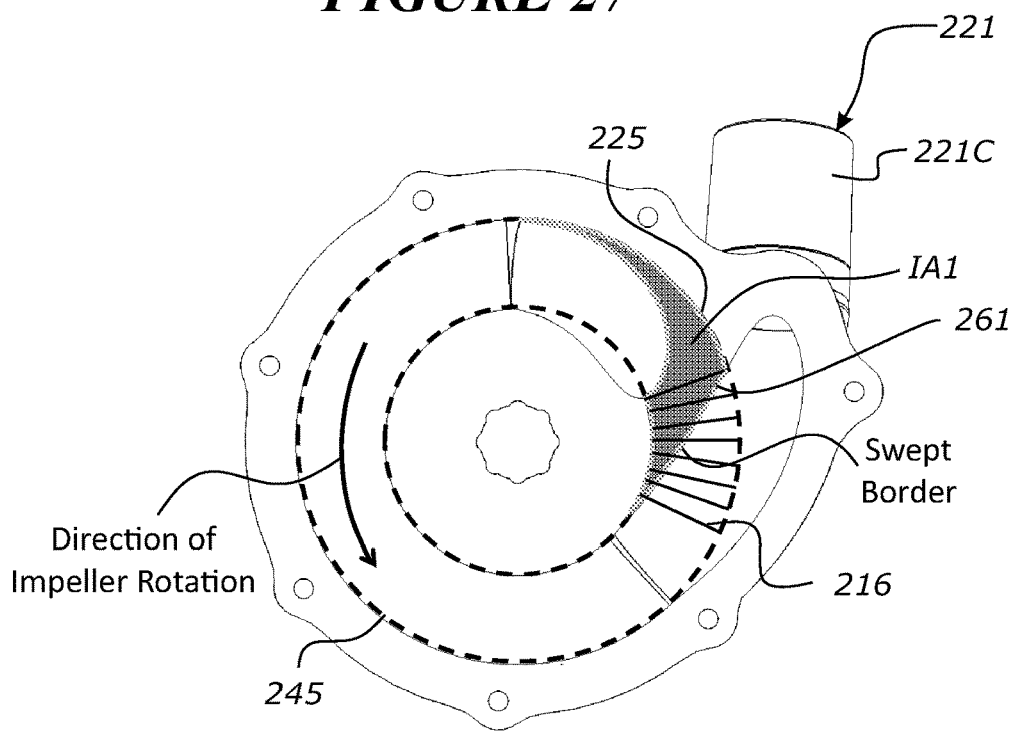

FIG. 28 shows the rotation of the impeller 215/impeller blades 275 and the resultant path of the impeller blades 275. The impeller blades 275 span the interior dashed circle to the exterior dashed circle, representing the impeller channel 245 in the lower housing 203. As the impeller 215 rotates, the blades pass the swept leading face 261 of the interrupter 225. The configuration of the interrupter 225 (that is that shape and orientation) is such that a plurality of impeller blades 275 transit the leading face 261 at any point in time during rotation of the impeller 215. Also this configuration of the interrupter 225 means that the leading edge 261 presents non-square to the impeller blades 275 such that each impeller blade 275 intersects the leading face 261 in a (non-zero) angle (that is, not parallel). This reduces the noise produced by the impeller 215 as the blades pass the interrupter 225.

This is because the interaction produced by the volume of air that is pushed passed the interrupter 225, in addition to each impeller blade itself passing the interrupter 225 is spread over an extended period of time. Each impeller blade 275 encounters the swept/curved leading face 261, forming an angle q with the leading face 261.

Each impeller blade rotating within the impeller channel 245 will gradually meet the swept leading edge 261 of the interrupter 225 as the impeller 215 rotates. A leading face of each respective impeller blade will first transit the interrupter 225 at C1, and after rotating further, transit a central portion of the interrupter 225 and then, the trailing edge of the impeller blade will eventually transit the trailing edge of the interrupter (and trailing face 261) at D1 at a (non-zero) angle and such that a plurality of blades are in transit past the trailing face 261 at any point in time. The impeller 215 therefore transits the interrupter 225 in a sweeping or slicing motion and the leading face 261 and trailing face 260 being swept/curved respectively present at an angle relative to the impeller blades. The gradual pass over of the interrupter 225 at a (non-zero) angle by the impeller blades 275 reduces the noise produced by the blower 200 by the impeller-interrupter interaction substantially. Noise is reduced further as the swept leading face 261 of the interrupter also results in a larger number of impeller blades simultaneously transiting (passing or encountering) the interrupter border at a given time.

2.3.4 Interrupter—Configuration #2

In a second configuration of the interrupter of this embodiment, the length of the interrupter, and therefore a distance between the inlet and the outlet port is increased compared to the first configuration. That is, the airflow channel length is reduced.

Figure 29:
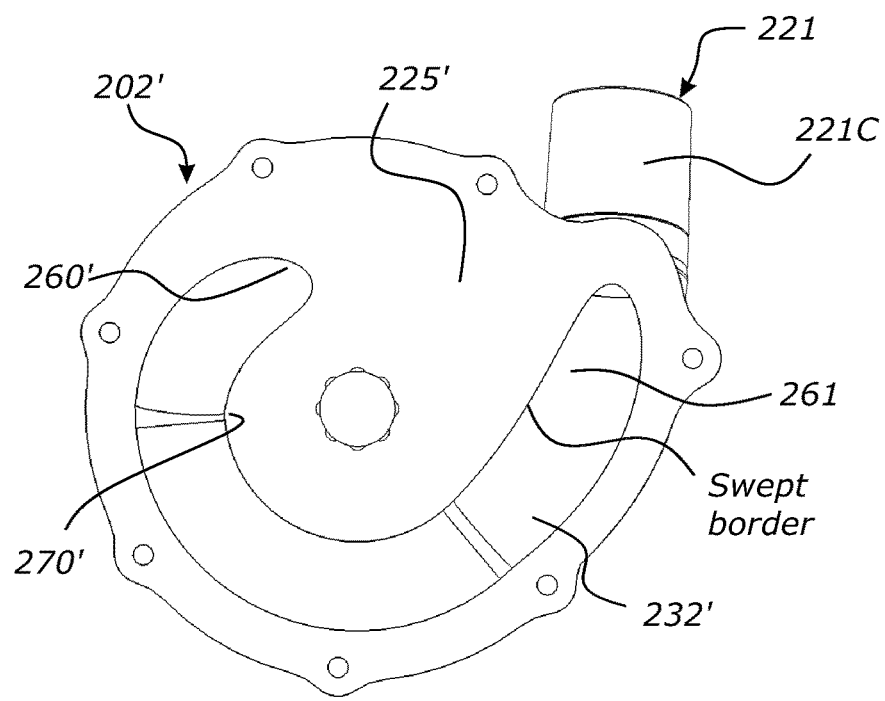
FIGS. 29 to 32 show a bottom view of a top housing, a perspective view, and a top view of a second configuration of the second embodiment of the regenerative blower detailing an interrupter and airflow channel according to the second configuration.
Figure 30:
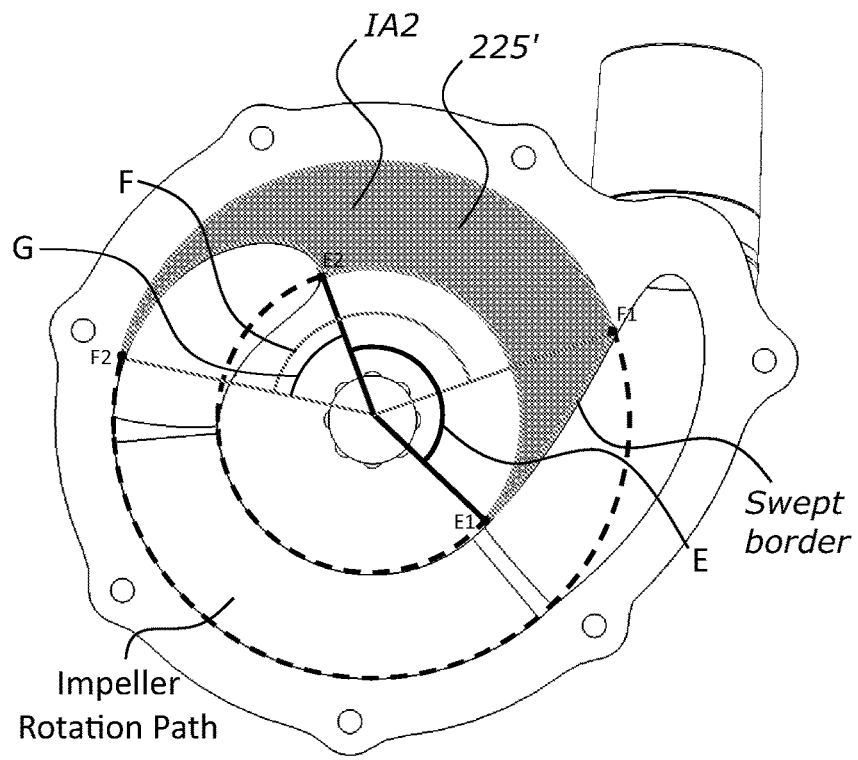

FIGS. 29, 30 are a bottom view of the top housing 202' showing the airflow channel 232' and interrupter 225' of the second configuration. The interrupter trailing face 260' starts at a later point (E2) in the airflow channel 232' of the top housing 202' and extends further around (to point F2) the airflow channel 232' of the top housing 202', providing a larger interrupter effective region. The point E2 is still at the nominal juncture 270' of the inlet port 220' and the airflow channel 232'. The trailing face 260' is a swept concave configuration when viewed from bottom of the top housing that extends from point E2 to point F2 across the airflow channel 232' of the top housing 202', such that the interrupter 225' blocks the airflow channel 232' to limit airflow going directly from the outlet port 221' to the inlet port 220'. The trailing face 260' sweeps across an angle G formed between the radius line between the central aperture and E2 and the radius line between the central aperture and F2. The sweep of the trailing face 260' can be any suitable configuration of shape. The angle G can be anything such that the swept trailing face 260' may take any configurations from between radial to tangential, depending on the required configuration and the configuration of the inlet conduit. The arc length between point E1 and point E2 is less than the arc length between point F1 and point F2, again leading to the "swept" interrupter profile. The angle E formed between the centre of the impeller's axis of rotation and the points E1 and E2 is less than the corresponding angle F formed between F1 and F2, and F1 is rotated counter-clockwise relative to a radial line through E1.

The leading face 261 of the interrupter remains similar as the first configuration, although it may start at a slightly more advanced point in the arcuate channel, at point E1. The airflow channel 232' is shortened because the trailing face 260' is located at a larger angle from the leading face 261.

Like in the first configuration, the interrupter of the second configuration provides blade pass noise reduction compared to existing regenerative blowers. The longer interrupter is, the more it reduces air leak between the inlet port and the outlet port. Overall however, the two interrupter configurations perform similarly.

2.3.5 Housing—Configuration #2

Figure 31:
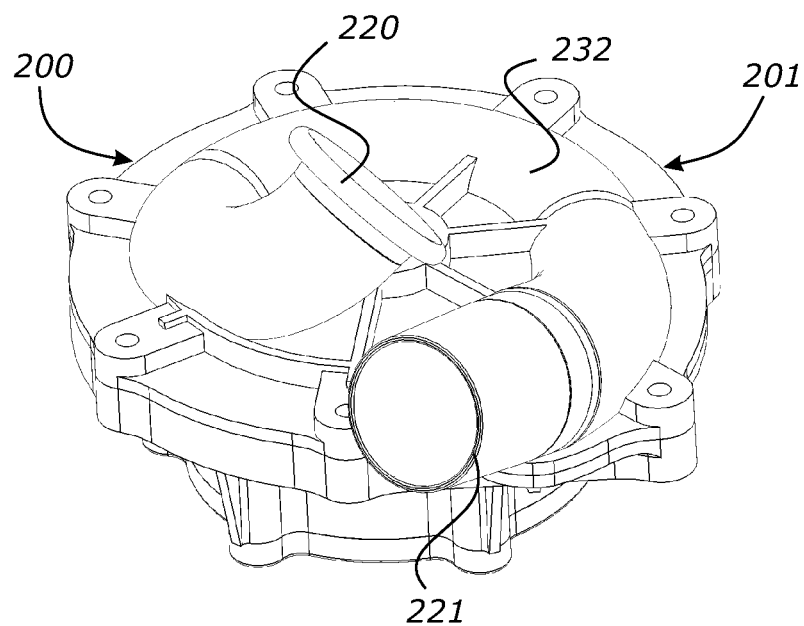
Figure 32:
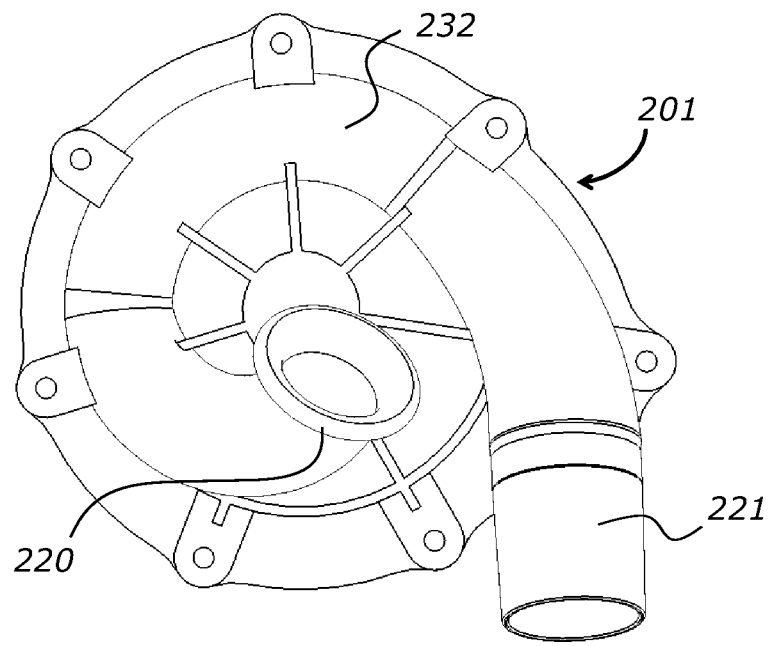
Figure 33:
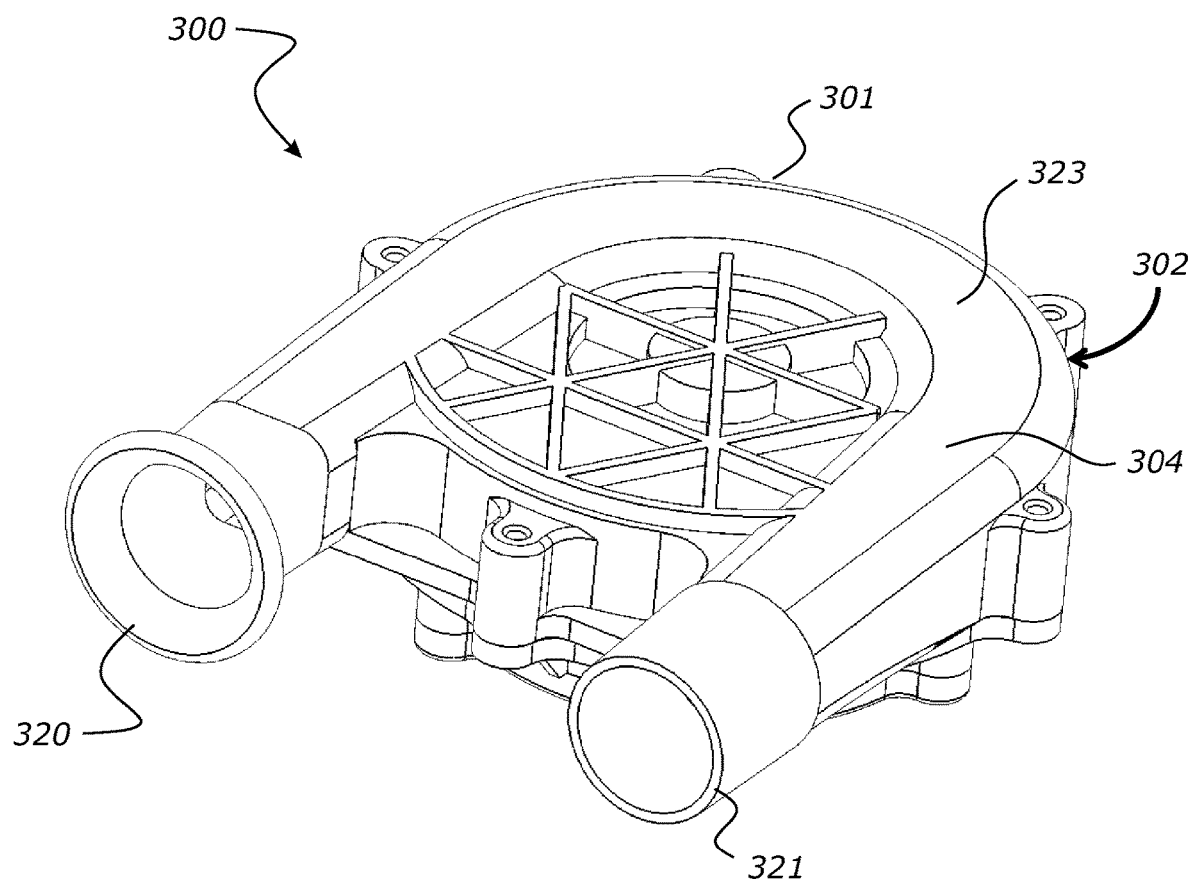
FIG. 33 shows a perspective view of a regenerative blower according to a third embodiment.

The interrupter of configuration #2 leads to a slightly different configuration of the inlet port 220 and outlet port 221 of the top housing. Referring to FIGS. 31, 32, the inlet aperture 220A and collar 220B are spaced further away from the outlet aperture 221A and collar 221B along the arcuate path, resulting in the inlet conduit integrally forming into the airflow channel 232' at the nominal inlet juncture 270' at a later position further around the airflow channel 232' than for configuration #1.

2.3.6 Example Dimensions for Second Embodiment

Exemplary, non-limiting, examples of dimensions of the second embodiment will be detailed below.

Figure 22:
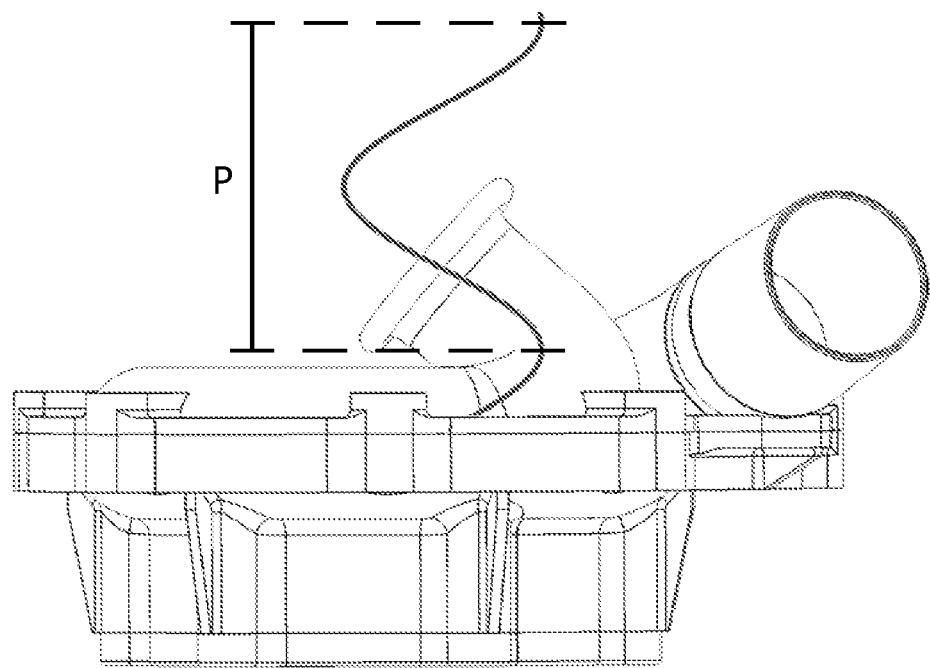
Figure 23:
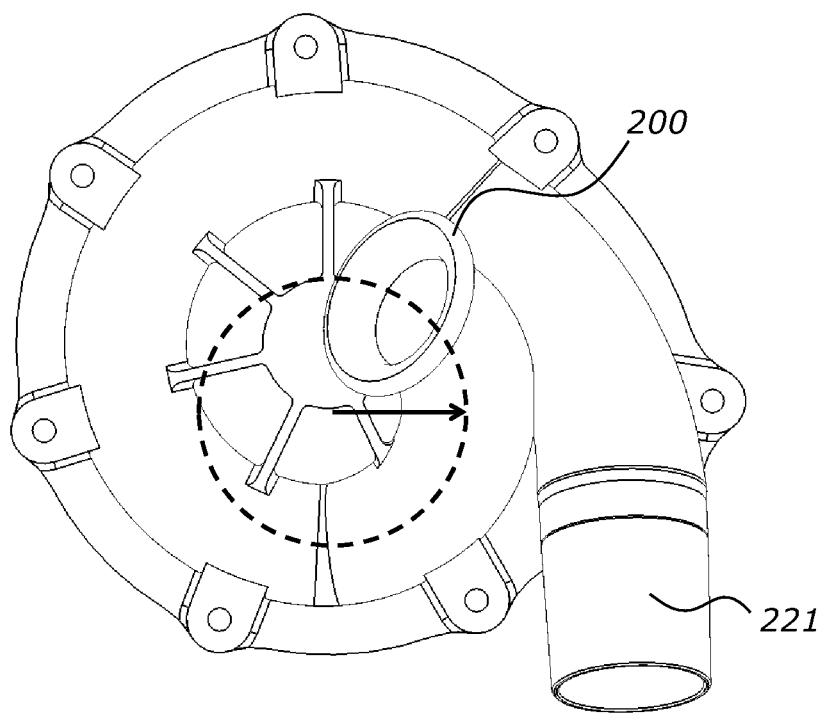
Figure 24:
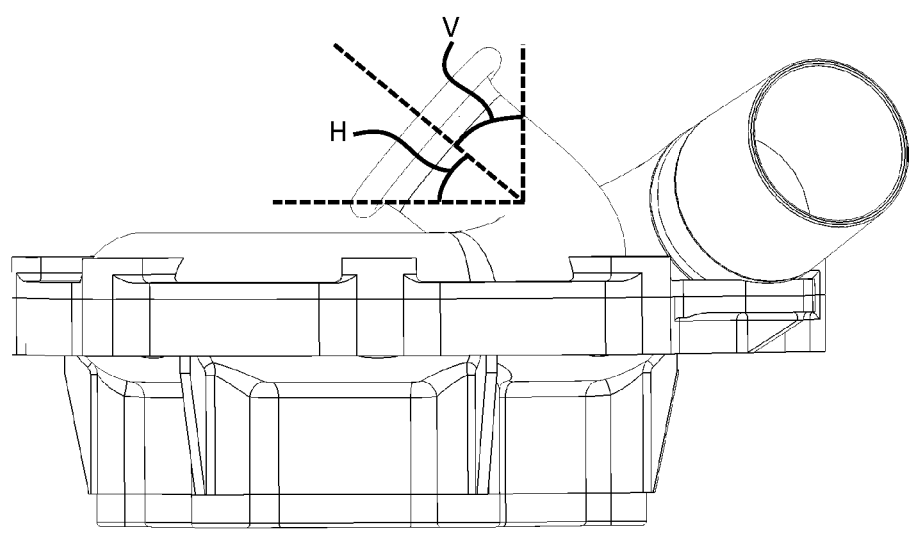
Figure 25:
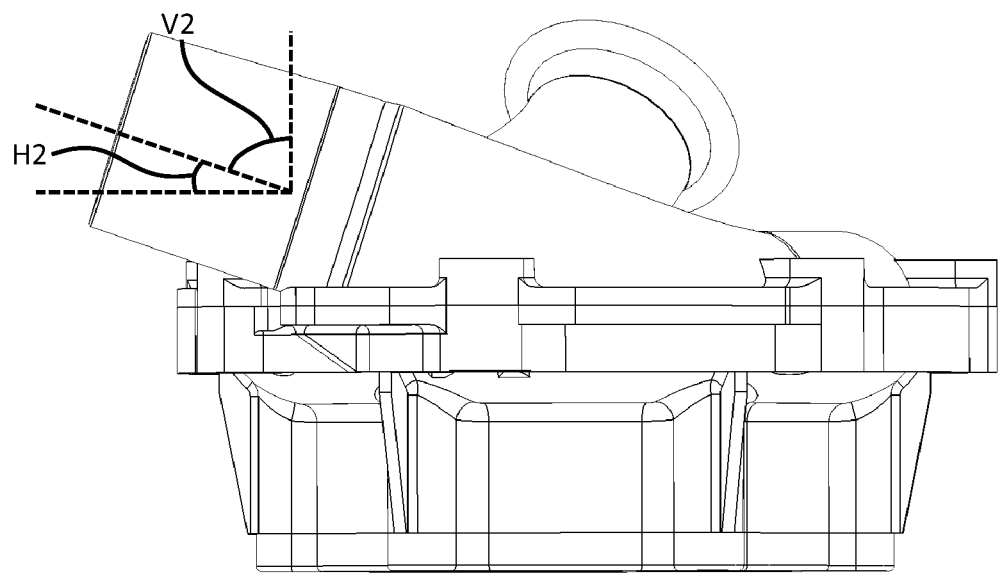

As a non-limiting example, the inlet can include an inlet helical section. The inlet helix is an inlet partial helix that is a variable pitch helix, with respect to an origin in the centre of the base of the helix. Referring to FIGS. 22, 23, the inlet could have the following dimensions.
Where the helix intersects with the airflow channel, the helix has the dimensions:
Height=0, Rev=0, Pitch (P)=20 mm, Radius (R)=27.75 mm (diameter=55.5 mm)
Where the helix finishes, it has the following dimensions:
Height=18 mm, Rev=0.3, Pitch=100 mm, Radius=13 mm (diameter=26 mm)
Where Rev=0.3 means the helix has rotated 30% around a complete revolution, or 108°.
Alternatively, where the inlet helix intersects with the airflow channel, the helix can have dimensions within the ranges:
Height=0, Rev=0, Pitch=10-30 mm, Radius=25-30 mm (diameter=50-60 mm)
Where the alternate arrangement finishes, it may have the following dimensions:
Height=15-20 mm, Rev=0.2-0.4, Pitch=90-110 mm, Radius=10-20 mm (diameter=20-40 mm).
In an alternative non-limiting example, the inlet helix can be a standard (non-variable) helix. The inlet has the following dimensions.
Pitch=20 mm, Radius=27.75 mm (diameter=55.5 mm), or
Pitch=100 mm, Radius=13 mm (diameter=26 mm)
In alternative non-limiting examples, the inlet helix can be a standard (non-variable) helix with dimensions within the following ranges.
Pitch=10-110 mm, Radius=15-40 mm (diameter=30-80 mm).
In alternative configurations, these dimensions may be varied depending on size requirements or constraints on the blower.
Referring to FIGS. 22, 23, the outlet port can include an outlet helical section. The outlet helix is again a variable pitch helix. Where the helix intersects with the airflow channel, the helix has the properties:
Height=0, Rev=0, Pitch=7 mm, Radius=27.75 mm (diameter=55.5 mm)

Where the helix finishes, it has the following properties: Height=11 mm, Rev=0.2, Pitch=103 mm, Radius=45 mm (diameter=90 mm)

Alternatively, where the outlet helix intersects with the annular channel, the helix can have dimensions within the ranges:
Height=0, Rev=0, Pitch=2-20 mm, Radius=20-35 mm (diameter=40-70 mm)

Where the alternate arrangement finishes, it may have the following dimensions:
Height=5-20 mm, Rev=0.1-0.4, Pitch=80-120 mm, Radius=20-70 mm (diameter=40-140 mm).

Alternately, the outlet helix can be a standard or non-variable helix with the following properties:
Pitch=7 mm, Radius=27.75 mm (diameter=55.5 mm), or Pitch=103 mm, Radius=45 mm (diameter=90 mm)

In alternative non-limiting examples, the outlet helix can be a standard (non-variable) helix with dimensions within the following ranges.
Pitch=2-120 mm, Radius=15-60 mm (diameter=30-120 mm).

Certain physical constraints on the helixes described are accounted for in the designs as the inlet and outlet ports cannot pass through each other.

More generally, the profile of the inlet helical section and/or the outlet helical section can be a helix with a radius between about 10 and about 40 mm, and a pitch between about 1 and about 120 mm, depending on the physical constraints of the blower.

In one, non-limiting, example of configuration #1 of the interrupter, the arc length of the interrupter between point C1 and point C2 is less than the arc length between point D1 and point D2. Furthermore, point D1 is displaced counter-clockwise from a radial line passing through the origin and C1. The angle C formed between the centre of the impeller's axis of rotation and the points C1 and C2 (angle C) is less than the corresponding angle formed between D1 and D2 (angle D). Angle C is between about 55° and 70°, such as equal to or about 63.2° and angle D is between about 60° and 80°, such as equal to or about 69.6°. The interrupter effective region has an area IA1, with IA1 being the area of the greyed shape of FIG. 28. In the illustrated embodiment, IA1 is between about 200 mm$^2$ to 300 mm$^2$, such as equal to or about 247.43 mm $^2$.

In one, non-limiting, example of configuration #2 of the interrupter, angle E is between about 140° and 165°, such as equal to or about 153.6° and angle F is between about 150° and 170°, such as equal to or about 159.6°. The interrupter effective region of this configuration has an area IA2, with IA2 being the area of the greyed shape of FIG. 30. In the illustrated embodiment, IA2 is between about 700 mm$^2$ and 1000 mm$^2$, such as equal to or about 856.17 mm$^2$. Comparatively, the ratio of IA1:IA2 is between about 1:2 and 1:5, such as equal to or about 247.43:856.17, or equal to or about 1:3.46. The interrupter effective region of the example of configuration #1 of the interrupter is therefore between about 2× and 5×, such as equal to or about 3.46× the surface area of the interrupter effective region of the example of configuration #2 of the interrupter, or between about 200% and 500%, or equal to or about 346% of the size of the region.

Each radial impeller blade encounters the swept leading face, forming an angle φ with the swept border of the leading face. In one, non-limiting example, φ is initially between about 80° and 110°, such as equal to or about 90° as the interior edge of each impeller blade encounters the swept border. This angle varies along the length of the swept boarder, to finish at the tip of the impeller blade at between about 35° and 45°, such as equal to or about 41°.

2.4 Third Embodiment of a Regenerative Blower

FIGS. 33 to 66 show a regenerative blower 300 according to a third embodiment. Features of the third embodiment that are the same or similar to those of the first embodiment or second embodiment may not be described fully or at all, but it will be appreciated by those skilled in the art that relevant portions of the description relating the first and second embodiment or any other embodiments described herein apply to this embodiment, where appropriate.

2.4.1 Overview

The regenerative blower 300 comprises a housing 301, formed of a top housing 302 and bottom housing 303 which are coupled together to form an interior region for a motor and a channel 304. The housing 301 comprises a first port 320 and a second port 321, which can provide/function as inlet and outlets to the channel 304. As describe previously, the direction of airflow through the first port 320 and second port 321 ports can be reversable such that each port can act as an inlet or an outlet depending on the direction the impeller rotates. The first port 320 and the second port 321 are parallel or approximately parallel with respect to each other, and are each are integrally formed with the housing 301 to fluidly communicate with the channel 304 of the blower 300.

Figure 34:
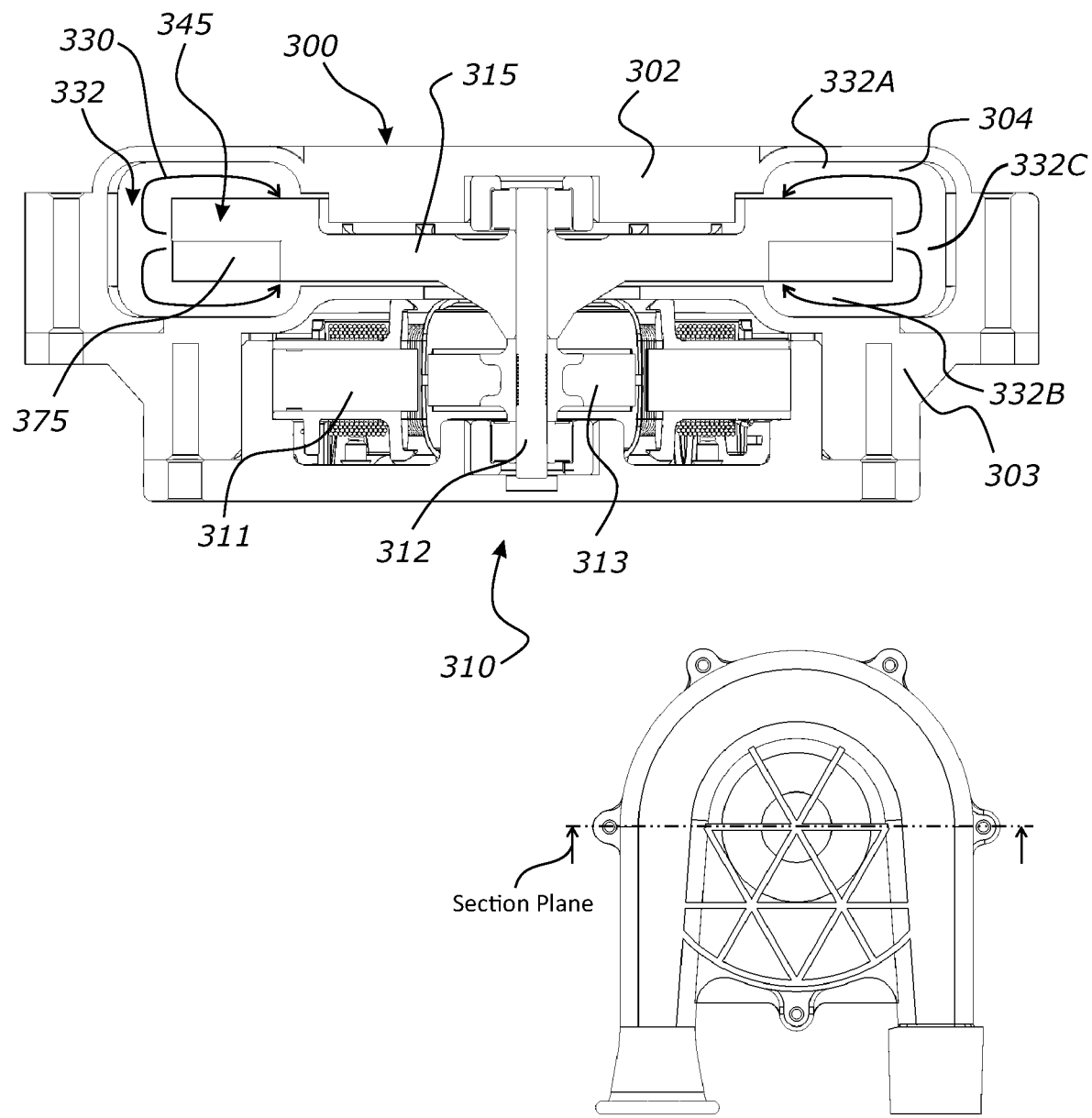
FIGS. 34 to 39 show cross-sectional and elevation views of the regenerative blower according to a first configuration of the third embodiment.

In this embodiment, the channel 304 comprises an airflow channel 332 and an impeller channel 345. The airflow channel comprises an upper airflow channel 332A (which is arcuate), lower airflow arcuate channel 332B, and lateral airflow channel 332C, such as previously described in relation to the generic embodiment of FIG. 1 and as will be described below. The upper airflow channel 332A and lower airflow channel 332B are defined by the top and bottom housings respectively, and provide airflow channels above and below the impeller channel/impeller. In other words, the upper airflow channel 332A is defined by a space between the upper side of the impeller 315 (when oriented as shown in FIG. 34) and an inner surface of the top housing 302. The lower airflow channel 332B is defined by a space between the underside of the impeller 315 (when oriented as shown in FIG. 34) and an inner surface of the bottom housing 303. This allows airflow on both sides of the impeller 315. The lateral airflow channel 332C provides for additional recirculation of airflow in the upper 332A and lower 332B channels. The upper 332A, lower 332B and lateral 332C airflow channels combine to provide the airflow channel 332 of the blower 300. The impeller 315 rotates within the impeller channel 345. The impeller channel 345 at least partially coincides with the airflow channel 332. The inlet port 320 and outlet port 321 approach tangentially or approximately tangentially with respect to the channel 304/direction of rotation of an impeller blades 375 within the impeller channel 345. The channel 304, has an arcuate pathway 304B between the inlet port 320 and the outlet port 321, as well as an annular cavity 304A for receiving the impeller 315 (the impeller channel 345). An interrupter 325 separates the outlet port 321 from the inlet port 320. The interrupter 325 acts to prevent or at least reduce airflow from leaking from the outlet port 321 to the inlet port 320 during use by providing a physical impediment preventing the air flow.

Figure 35:
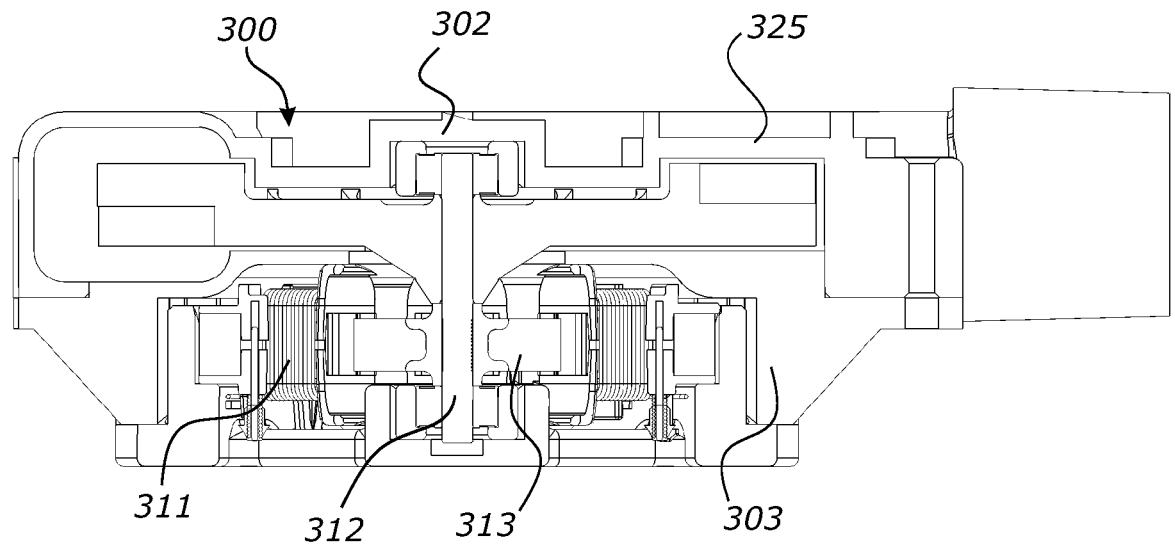
Figure 35:
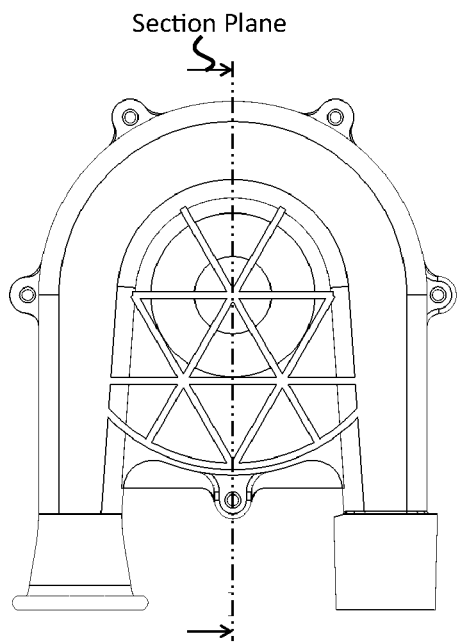

Referring to FIGS. 34, 35 there is a motor assembly 310 comprising a stator 311, a shaft 312 and a rotor 313 located in the interior region of the bottom housing 303. Details of motors, their assembly and operation will be known to those skilled in the art and will not be described further here. An impeller 315 is coupled to the shaft 312 and driven by the motor 310 in use.

Impeller blades 375 formed into the impeller 315 rotate within the impeller channel 345 to provide airflow into and out of the inlet/outlet ports. A clearance is provided between the impeller blades 375 and the outer wall of the channel 304 to provide the lateral airflow channel 332C. As opposed to the regenerative blowers of the first and second embodiments, the channel 304 of the third embodiment can be considered an 'open' channel, as the lateral ends of the impeller blades are not directly adjacent the exterior perimeter of the channel 304. A radial clearance (shown in FIG. 34, for example) separates the end of the impeller blades 375 from the external perimeter of the channel 304. In the previous first and second embodiments, it was desirable to keep the radial clearance as small as possible, close to manufacturing tolerances, to maximise the performance of the blowers. In the case of the previously described embodiments, manufacturing tolerances can lead to a radial clearance between the impeller blades and the end of the channel of about 0.5-1 mm. In at least one configuration however, the radial clearance can be less than 0.5 mm, for example, approximately 0.1, 0.2, 0.3 or 0.4 mm. Increasing the radial clearance changes the air recirculation path 332C within the channel 304.

FIG. 34 show an air recirculation path 330 of the embodiment. The air recirculation path 330 allows the recirculating air to encounter the impeller multiple times on its way from the inlet port to the outlet port. The air cycles through the air recirculation path 330 enabling a successive pressure increase at each impeller pass, producing the regenerative characteristic of the blower 300.

2.4.2 Housing—Configuration #1

The housing 301 will be described in further detail with reference to FIGS. 40 to 42.

The housing 301 comprises a top housing 302 and a bottom housing 303. Referring to FIGS. 36 to 42, the top housing 302 is a generally arcuate body formed of a generally circular part 302A, with the first port 320 and second port 321 extending tangentially from opposing sides of the generally circular part. In the illustrated configuration, the first port 320 can be an inlet port 320. In the illustrated configuration, the second port 321 can be an outlet port 321. In this case, air flows 323 from first port 320 to second port 321. The top housing 302 comprises an arcuate path/channel defining the upper airflow channel 332A and at least part of the impeller channel 345. The inlet port 320, formed of a generally straight inlet, comprising itself and inlet aperture 320A, inlet collar 320B and inlet conduit 320C, integrally forms with the upper airflow channel 332A at a nominal junction 370. The upper airflow channel 332A is formed in the generally circular portion 302A of the top housing. The upper airflow channel 332A extends between the inlet port 320 and the outlet port 321. The outlet port 321 comprises an outlet aperture 321A, outlet collar 321B and outlet conduit 321C which is integrally formed at a nominal juncture 371 with the other end of the upper airflow channel 332A as the inlet port 320.

A plurality of lugs 342 are formed in a perimeter portion of the top housing to allow for coupling of the top housing 302 with the bottom housing 303, with screws, bolts or other fasteners. A perimeter wall 331 extends from the inlet port 320 around the perimeter of the top housing to the outlet port 321, and also between the space between the inlet and outlet ports ("front wall" 331A). The inner wall of the upper airflow channel 332A extends up and across into a flat shelf/plateau 380 that extends between opposite sides of the upper airflow channel 332A. An inner portion of the interior of the top housing 302 on the top shelf 380 comprises a central hub/boss 339 with an aperture or hole 338 for receiving a motor shaft 312 bearing. The hub 339 defines a wall of the impeller channel 345. The hub 339, like the interrupter 325, acts to impede the flow of air leaking from the outlet port 321 to the inlet port 320 during operation by creating a barrier preventing the flow of air from the outlet port 321 to the inlet port 320 via the central region of reduced vertical thickness of the impeller 315. The hub 339, the shelf 380 above the channel between hub and the front wall 331A, and the front wall 331A together form an interrupter 325, which will be described further below. The front wall 331A comprises an inside surface 369. The inside surface 369 of the front wall 331A is adjacent to, or at least partially defines a boundary of the impeller channel 345 in the region of the interrupter 325.

Figure 40:
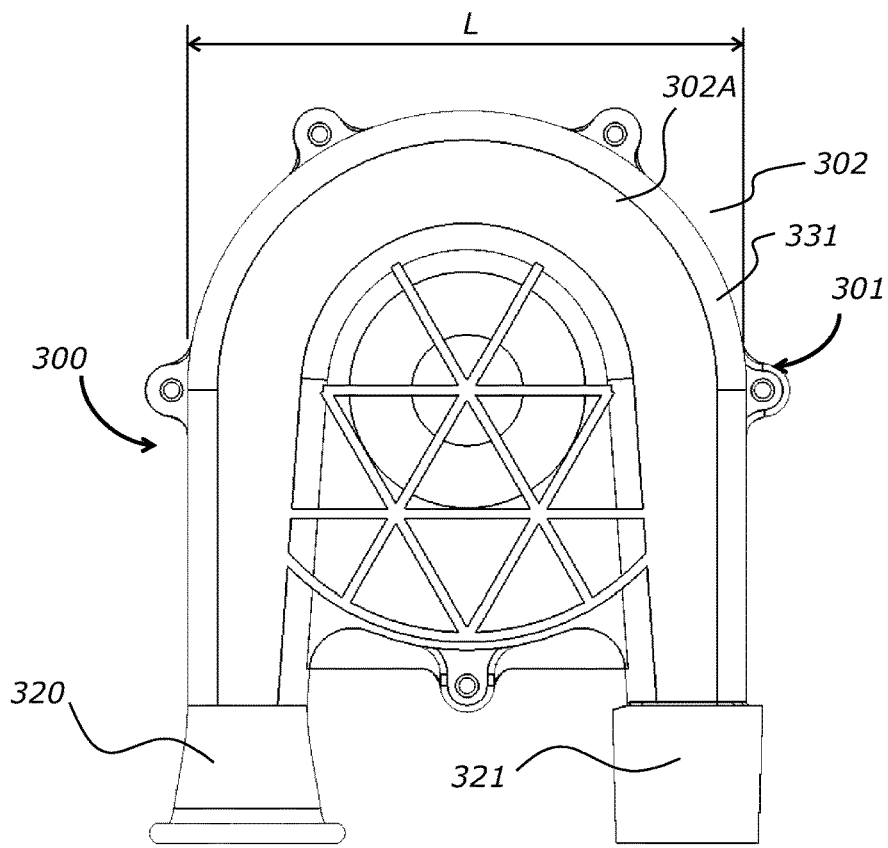
FIGS. 40 to 42 show the top housing and channels of the first configuration of the third embodiment.

The top housing 302 also has a triangular lattice and central hub as shown in FIG. 40 which provide stiffening for the structure.

Figure 41:
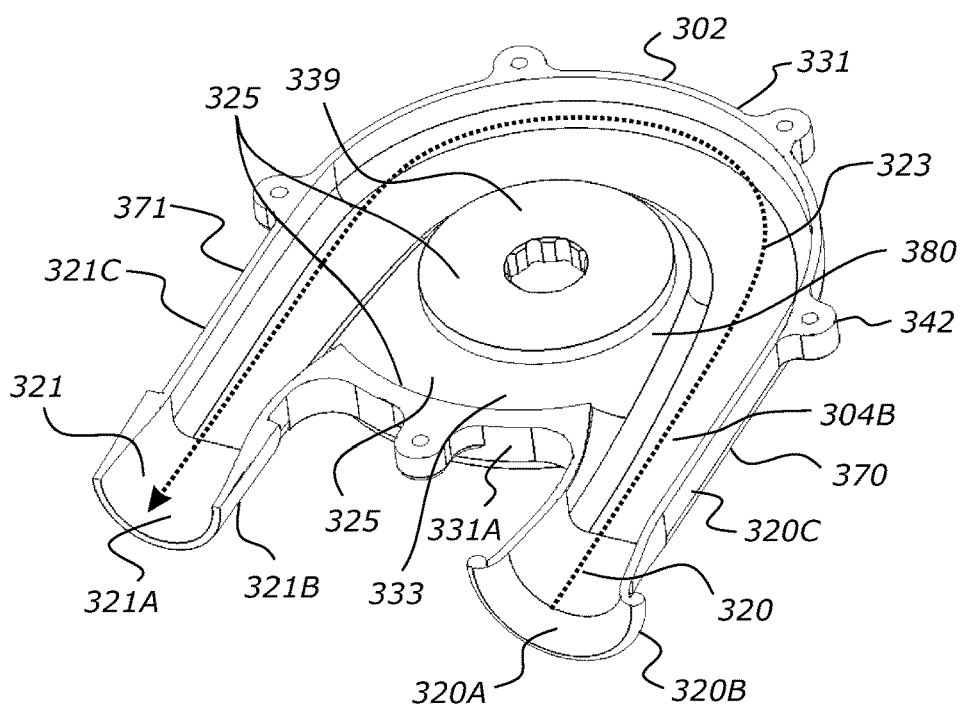
Figure 44:
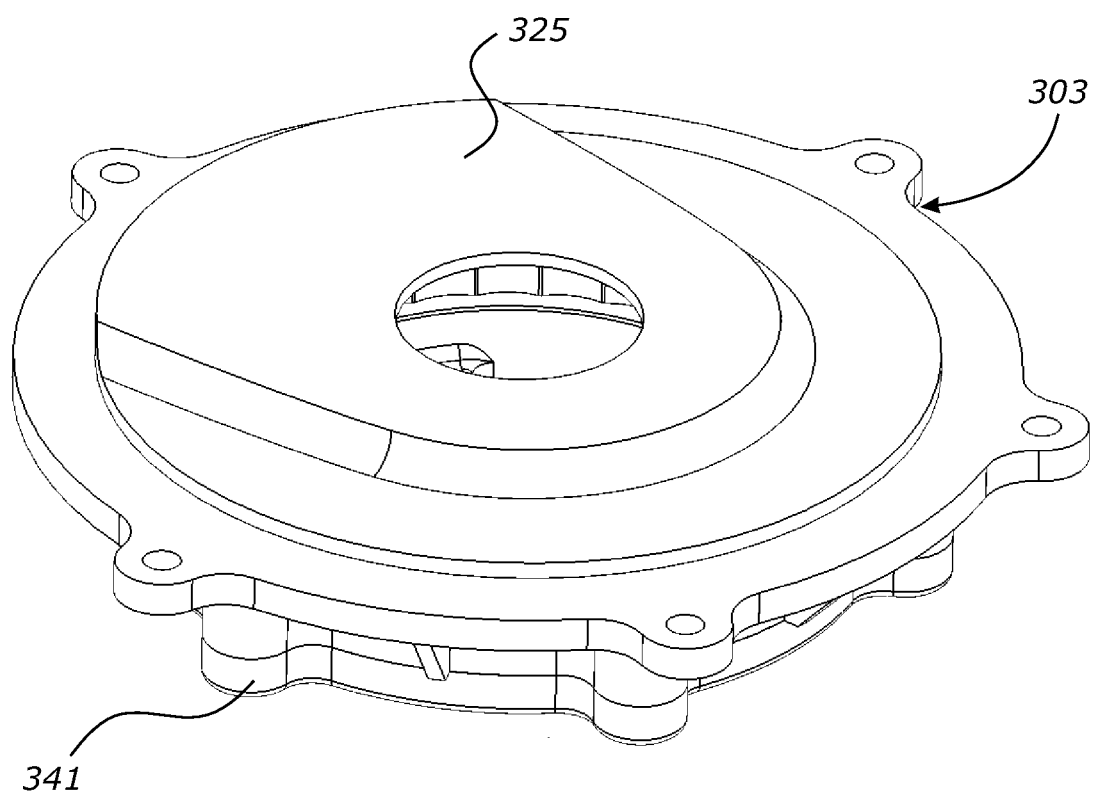
FIG. 44 shows a perspective view of a bottom housing of the first configuration of the third embodiment.

It should be appreciated that FIG. 41 does not show the full height of the top housing as is apparent from FIGS. 34 and 35. As can be seen from those Figures, the top housing 302 forms or holds the majority of the height of the airflow channel 332 (being the upper, lower and later airflow channels) which is rectangular in cross-section with filleted or rounded corners. The bottom part of the lower airflow channel 332B and inside corner of the lower airflow channel 332B is formed from a plate of the bottom housing 303, and the inside surface of the airflow channel 332 is formed from the central plateau/interrupter portion of the bottom housing. FIG. 44 shows a top perspective view of the bottom housing 303 and the bottom housing cap 341.

Figure 43:
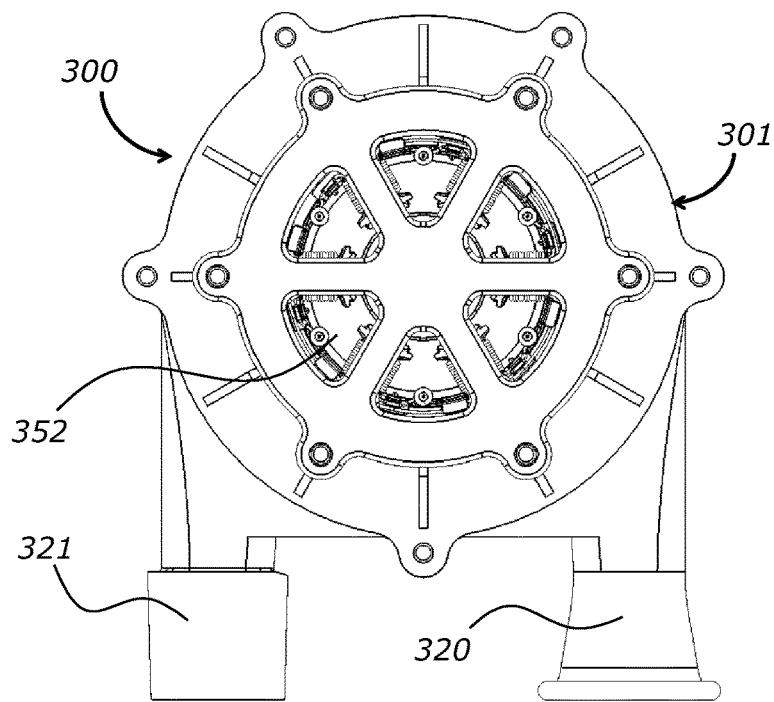
FIG. 43 shows a bottom view of the first configuration of the third embodiment of the regenerative blower.

Referring to FIG. 43, the bottom housing cap 341 also has a plurality of bottom housing cap apertures 352 for airflow for the reasons described in relation to the previous embodiments.

It is typically beneficial to maximise the length of the airflow channel 332, and therefore minimise the length of the interrupter 325, as doing so maximizes the pressure and flow performance of an impeller with a fixed radius. Having a relatively small interrupter however requires precise tolerances between the interrupter and the impeller to prevent or minimise leaks from the outlet port 321 to the inlet port 320.

One way to decrease the required tolerance is to increase the length of the interrupter. Increasing the length of the interrupter acts to impede the leakage of gas from the outlet port 321 to the inlet port 320 by creating a path of higher resistance to air flow.

2.4.3 Interrupter

Figure 45:
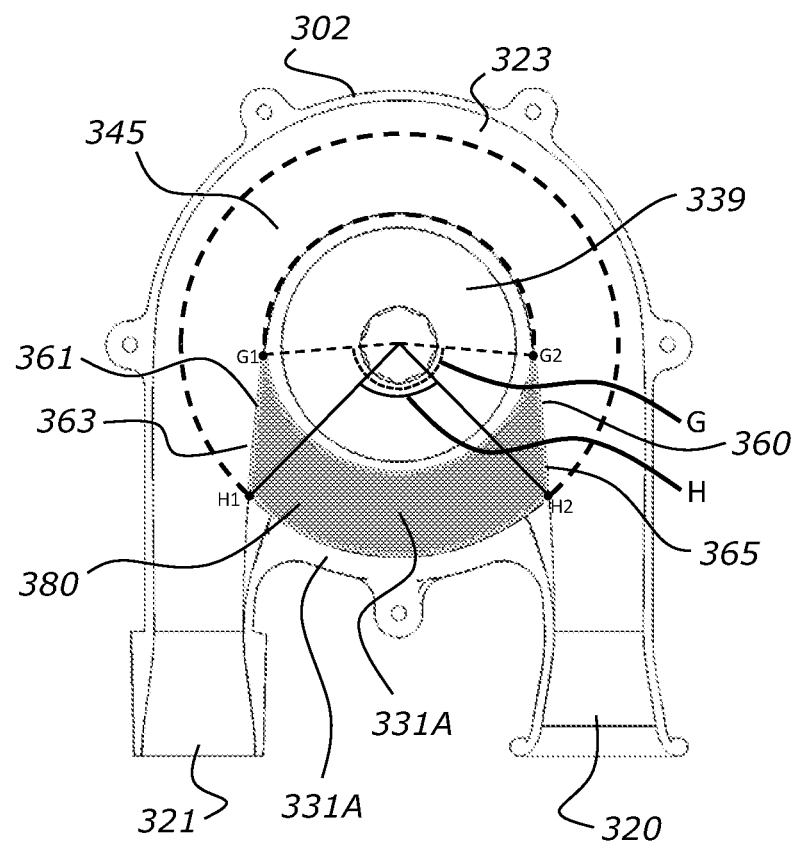
FIGS. 45 and 46 show a bottom view of the top housing detailing the interrupter and impeller channel of the first configuration of the third embodiment.
Figure 46:
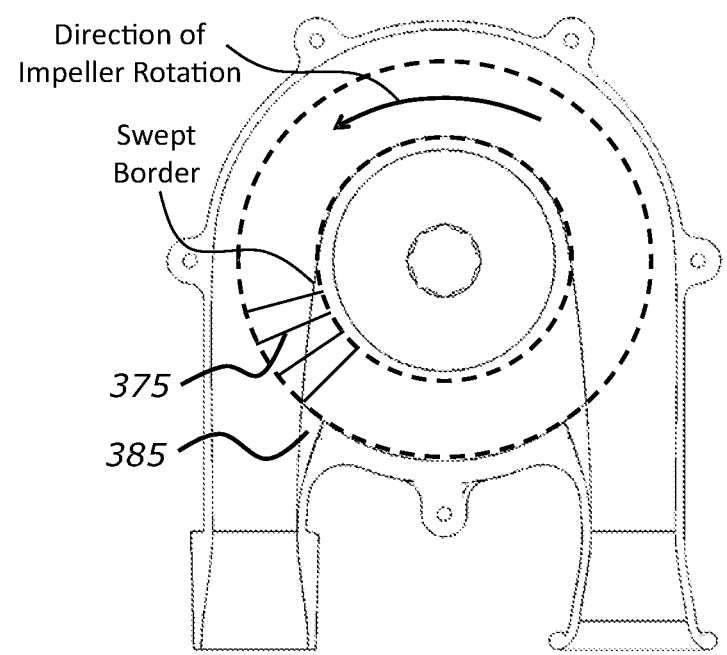

Referring to FIGS. 45 and 46, the interrupter (forming an interrupter effective region as shown in grey) is formed from the hub 339, the shelf 380, and the front wall 331A. The front wall 331A can be considered a vertical, perpendicular or transverse interrupter region 367, and the shelf 380 can be considered a planar interrupter region on the top housing 302. Corresponding vertical and planar interrupter regions can be on the bottom housing 303 matching the contour of the impeller 315 form the complete interrupter 325.

The shelf 380 and the front wall 331A at least partially define a leading face 361 of the interrupter 325. The leading face 361 is considered a leading face because it is the face of the interrupter 325 first encountered by each impeller blade 375 as it rotates through the impeller channel 345 as would be the case with the inlet port 320 and outlet port 321 as identified in the figures. The shelf 380 and the front wall 331A also at least partially define a trailing face 360 of the interrupter 325. The shelf 380 therefore defines a leading edge 363 and a trailing edge 365 respectively. In the illustrated configuration, the leading face 361 defines the leading edge 363, and the trailing face 360 defines the trailing edge 365. The leading edge 363 is the edge or corner of the shelf 380 where the interrupter effective region as shown in FIG. 45 meets the leading face 361. The trailing edge 365 is the edge or corner of the shelf 380 where the interrupter effective region as shown in FIG. 45 meets the trailing face 360. The edge between G2 and H2 on the shelf 380 provides the trailing edge 365. The trailing edge 365 can be in the form of a swept edge. Likewise, the edge between G1 and H1 on the shelf 380 provides the leading edge 363. The leading edge 363 can be in the form of a swept edge. If the direction of rotation of the impeller 315 was the reverse of what is shown in FIG. 46, the illustrated leading face 361 would become a trailing face 360, and the illustrated trailing face 360 would become a leading face 361.

Referring to FIG. 46, the configuration of the interrupter 325 (that is that shape and orientation) is such that a plurality of impeller blades 375 to transit the leading face 361 and/or the leading edge 363 at any one point in time during rotation of the impeller 315. Also this configuration of the interrupter 325 result in the leading face 361 and/or the leading edge 363 presenting non-square to the impeller blades 375 such that each impeller blade 375 intersects the leading face 361 and/or leading edge 363 at an (non-zero) angle (that is, not parallel). This provides advantages as discussed the previous embodiment.

Figure 47:
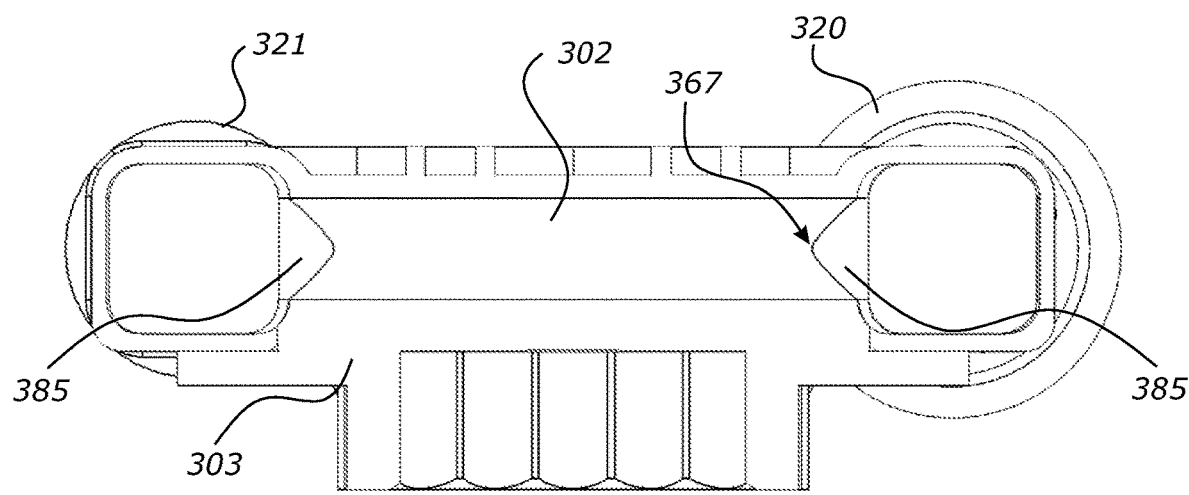
FIG. 47 shows a cross sectional view of the housing of the first configuration of the third embodiment.
Figure 47:
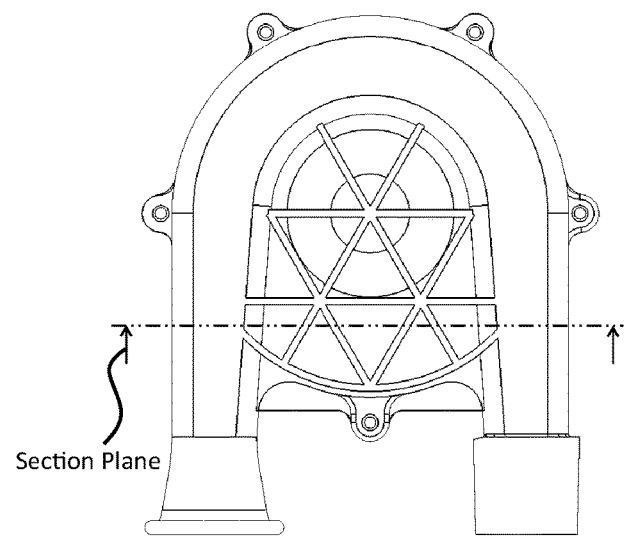
Figure 48:
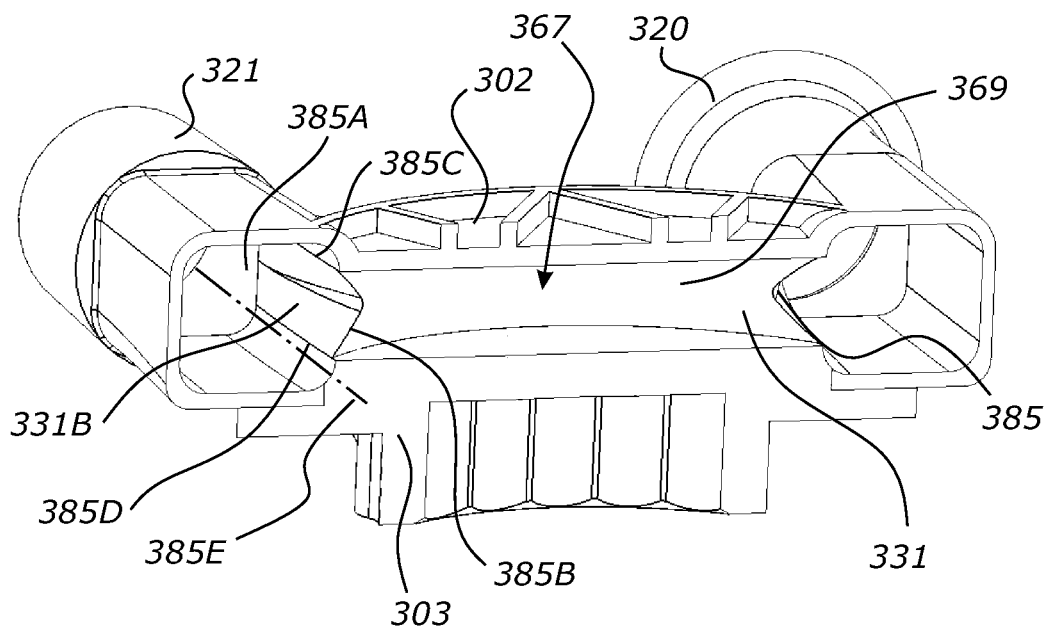
FIG. 48 shows a perspective view of a cross-section of the housing of the first configuration of the third embodiment.

Referring to FIGS. 47, 48, the interrupter 325 can optionally comprise a recess 385 (e.g. a notch, groove, indent, channel or the like). The recess 385 can be disposed on front wall side portions 331B bordering the inside of the inlet port 320 and outlet port 321 respectively. The recess 385 can optionally extend beyond the edges of the front wall side portion 331B and into the wall 320C, 321C and/or collar of the conduit of the inlet/outlet port itself. This provides a swept border on the perpendicular region of the interrupter 325. In addition to swept edges on the planar portion of the interrupter, a swept border on the perpendicular/transverse interrupter region can improve the noise characteristics of the blower 300. In one, non-limiting, example, the recess is a substantially 'v'-shaped notch as shown in FIG. 47. In one example, referring to FIG. 47, each notch can be 9.3% of the total horizontal length of the front wall 331A. Alternatively, each notch can be between 5-15% of the horizontal length of the front wall 331A (measured along the curved surface), and for example 5, 6, 7, 8, 9, 10, 11, 12, 13, 14 or 15% of the horizontal length of the front wall when viewed like in FIG. 47.

Referring to FIG. 48, recess 385 starts at the outlet/inlet port end 385A of the front wall side portion 331B bordering the outlet/inlet port 320/321. It is formed from the front wall side portion 331B gradually curving inwards (in the vertical plane) to a centre line/axis from the outlet/inlet port end 385A to the front edge 385B of the front wall side portion 331B in combination with the front wall side portion 331B curving inwards to the centre axis/line (planar with the axis of rotation of the impeller 315) from the top 385C and bottom 385D edges towards the centre line 385E of the bordering wall 331B. This forms the V shaped cross-section recess 385 along the centre 385E of the bordering wall 331B that increases in depth along the length of the front wall side portion 331B.

The configuration of FIGS. 47 and 48 can be described in another way. The front wall 331A has a first side face 331B proximate the first end of the channel 304, and the impeller blades 375 are adapted in use to rotate away from and pass the first side face 331B, wherein the first side face comprises a recess 385. The front wall 331A has a second side face 331B proximate the second end of the channel 304, the impeller blades 375 adapted in use to rotate towards and pass the second side face 331B, wherein the second side face comprises a recess 385. The recess on the first side face 331B and/or the recess on the second side face 331B: a) curves inwards from a back edge to a front edge along the centre axis, and b) curves inwards from the top and bottom edges towards a centre axis between the top and bottom edges.

Alternatively, the recess 385 can be other shapes, such as a gradient from the upper end of the vertical interrupter region 367 to the lower end, a substantially 'U'-shaped, 'W'-shaped, 'M'-shaped cross-section recesses or the like.

Figure 49:
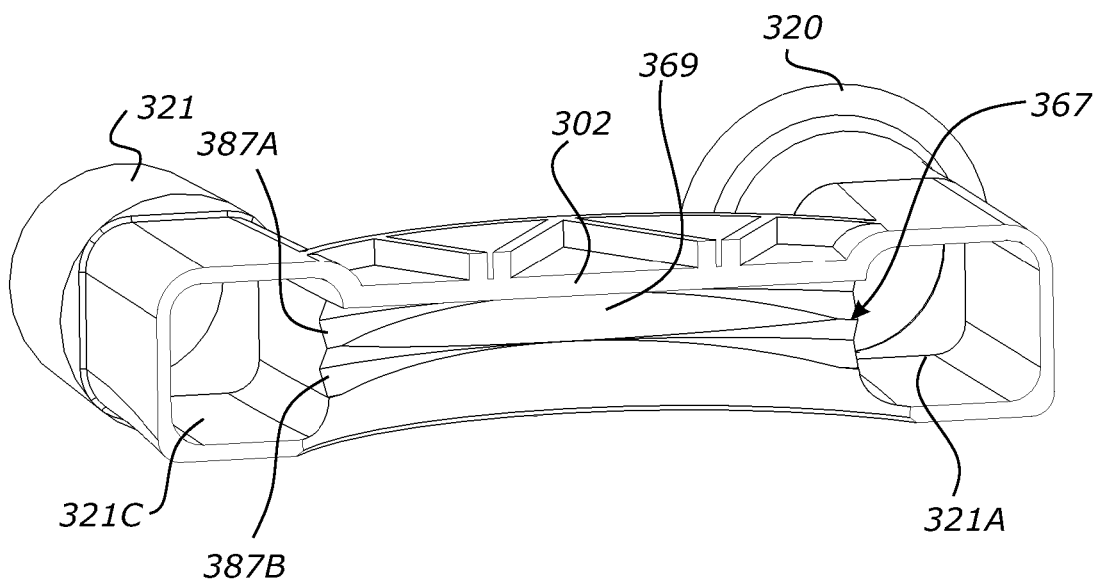
FIG. 49 shows a perspective view of a cross-section of a housing of a second configuration of the third embodiment with recesses in a transverse face of the interrupter.
Figure 50:
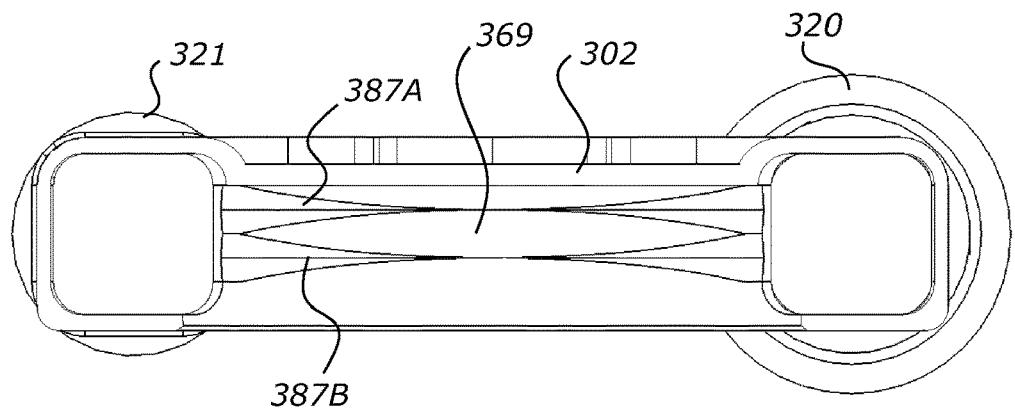
FIG. 50 shows an elevation view of the cross-section of FIG. 49.

In an alternative configuration, instead of a recess 385 in the front wall side portions 331B, a recess or recesses 386 (e.g. groove, notch, indent, channel or the like) are provided in the inside surface 369 of the front wall 331A bordering the impeller channel 345. In at least one form, the one or more recesses 386 can be in the form of, or referred to as transverse recesses. Referring to FIGS. 49 and 50, there are two tapered elongated recesses 387A, 387B at each end of the inside surface 369 of the front wall 331A. Each of these recesses can be called a transverse recess 387A, 387B. The recesses 387A, 387B span across the concave front wall 331A, with each recess 387A, 387B starting with a maximum width and depth at a one edge 385B of the inside surface 369 of the front wall 331A, decreasing to a minimum width and depth towards the centre of the front wall 331A and then expanding out to a maximum width and depth at the opposite edge 385B of the front wall 331A. In at least one alternative configuration, instead of two recesses 386, the interrupter front wall 331A could have one recess, or more than two recesses. Also, the configuration of the recess could take a different shape.

In another alternative configuration a recess starts at one or both edges of the front wall 331A and each proceeds as a tapered recess across the inside surface 369 of the front wall towards the centre and terminates at an end point along the surface, such as some percentage along the length of the surface. Where there is a recess starting at both edges, they can meet at a nominal juncture, which may be half way, but also could be at another point. But, alternatively, the recesses might not meet at all and not traverse the entire inside surface 369 of the front wall 331A. As such, each recess terminates at a distance along the front wall which can be some percentage of the width of the inside surface 369 of the front wall 331A, between 0-100%, such as 30%, 40%, 50%, or any other real number percentage, and each recess might traverse a different percentage of the inside surface 369 of the front wall 331A. Each recess can start with a maximum width of approximately 50% of the total width of the inside surface 369 of the front wall 331A at each end of the front wall 331A, and has a minimum width along the inside surface 369 of the front wall 331A (for example towards the centre of the inside surface).

Figure 51:
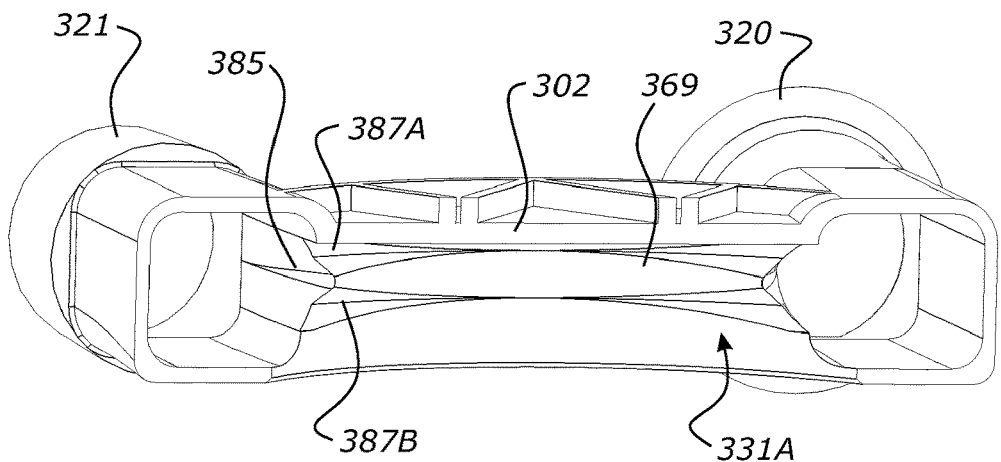
FIG. 51 shows a perspective view of a cross-section of a housing of a third configuration of the third embodiment with recesses in side faces and a transverse face of the interrupter.
Figure 52:
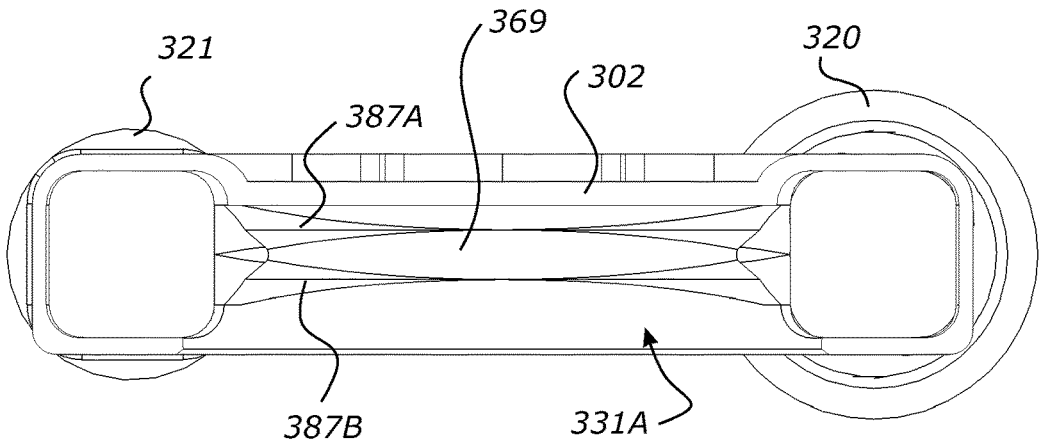
FIG. 52 shows an elevation view of the cross-section of FIG. 51.

In yet another configuration, as shown in FIGS. 51, 52, the recesses of both configurations above can be combined. That is, there are recesses on the front wall side portions 331B and on the inside surface 369 of the front wall 331A. The front wall side portions 331B includes recesses 385 as described with reference to FIGS. 47 and 48. The inside surface 369 of the front wall 331A includes elongated recesses 387A, 387B as described with reference to FIGS. 49 and 50.

The introduction of recesses 385 in the front wall side portions 331B and elongated recesses 387A, 387B on the inside surface 369 of the front wall 331A as shown in FIGS. 51 and 52 can assist in reducing the blade pass noise produced by the blower 300. The purpose of the recesses is to spread the effect of the interrupter on a given blade over a longer time period, which reduces the maximum noise produced by the blade passing the interrupter 325.

Figure 53:
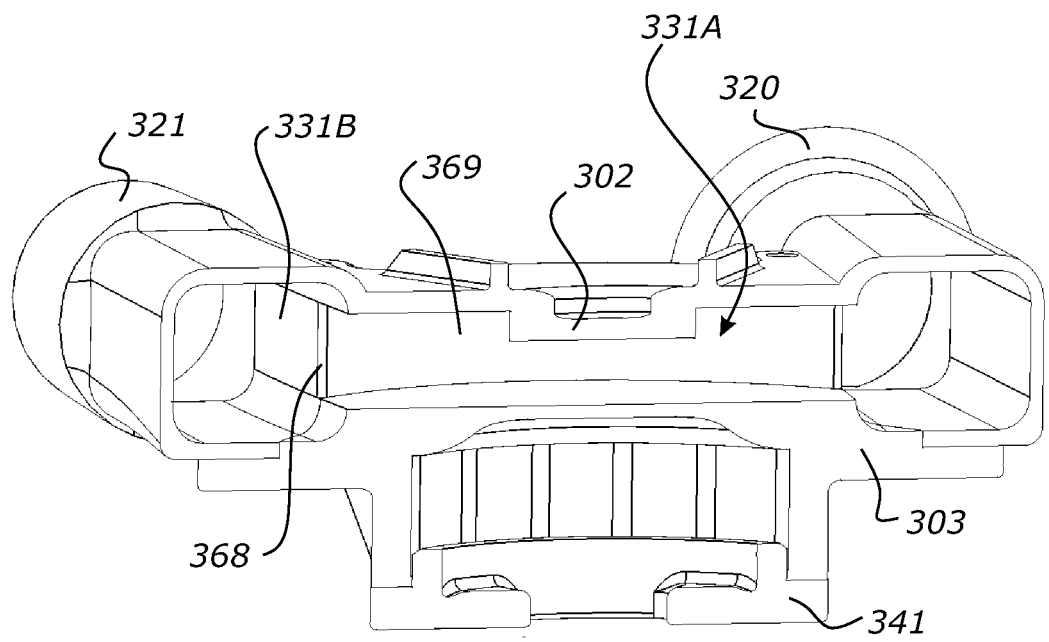
FIG. 53 shows a perspective view of a cross-section of a housing of a fourth configuration of the third embodiment.
Figure 54:
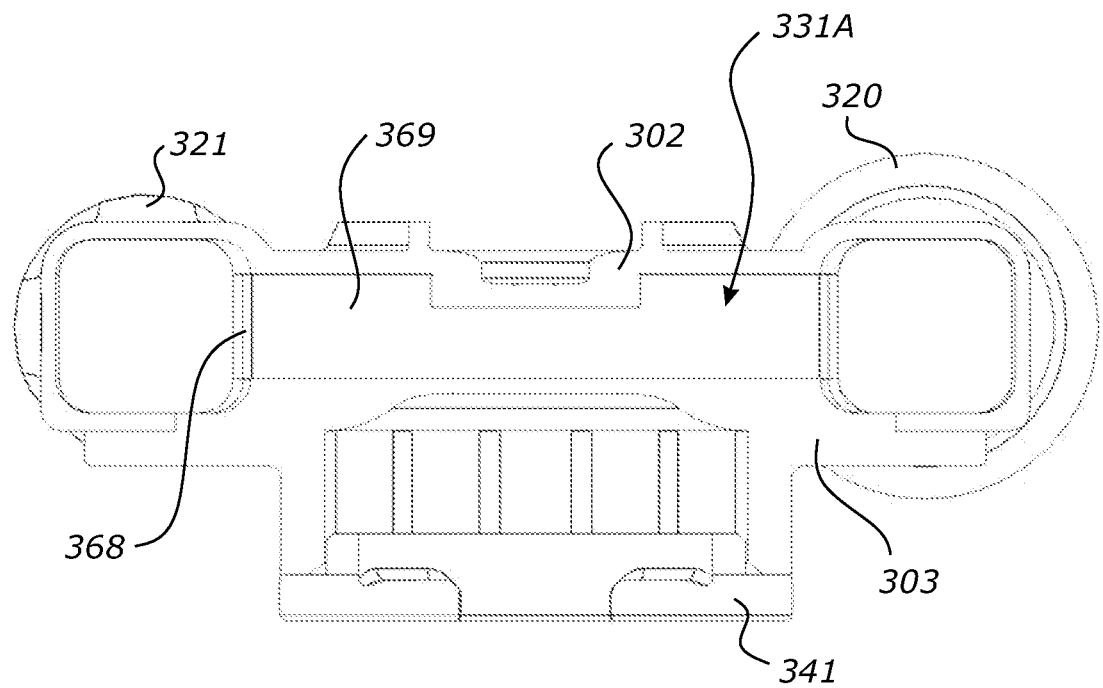
FIG. 54 shows an elevation view of the cross-section of FIG. 53.

In yet another configuration, as shown in FIGS. 53, 54, the front wall side portions 331B meet the inside surface 369 of the front wall 331A at corners 368. For example, the corners 368 can be shaped to be relatively sharp, to act to slice and divert air as the impeller 315 passes, reducing the noise produced by blade pass. Alternately, the edges can be rounded or chamfered. In the illustrated configuration, the angle between the inside surface 369 of the front wall 331A and each front wall side portion 331B is an acute angle.

2.4.4 Impeller

The impeller 315 described in this section can be used with embodiment three, and also the fourth and fifth embodiments described later, although with different dimensions as required.

Figure 55:
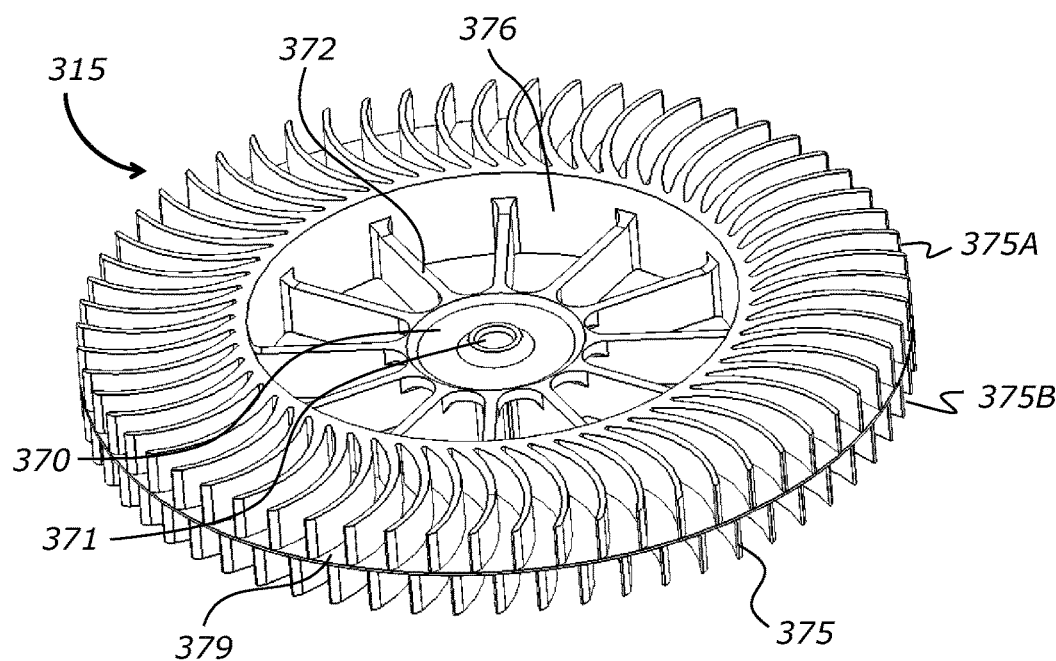
FIGS. 55 to 57 show perspective, top and elevation views of an impeller suitable for use with the third embodiment of the regenerative blower.
Figure 56:
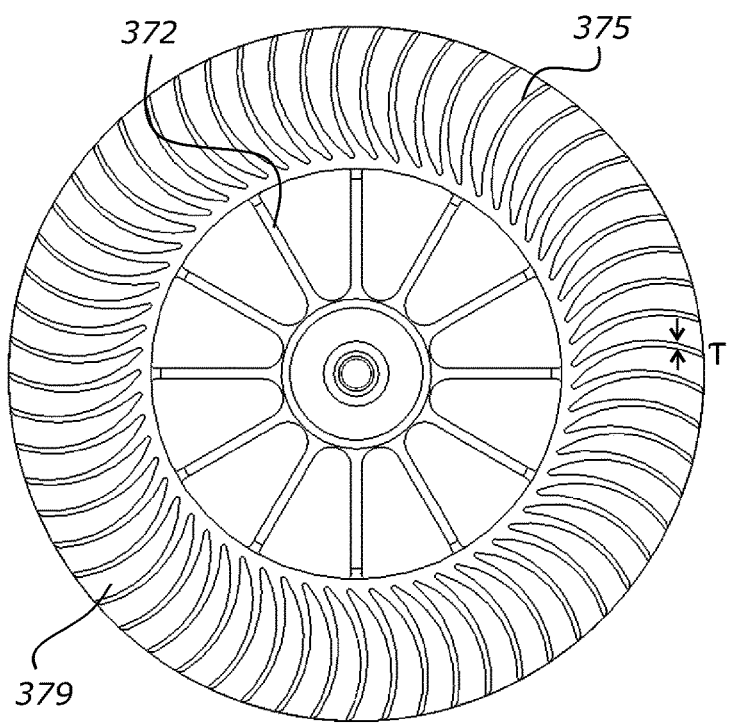
Figure 57:
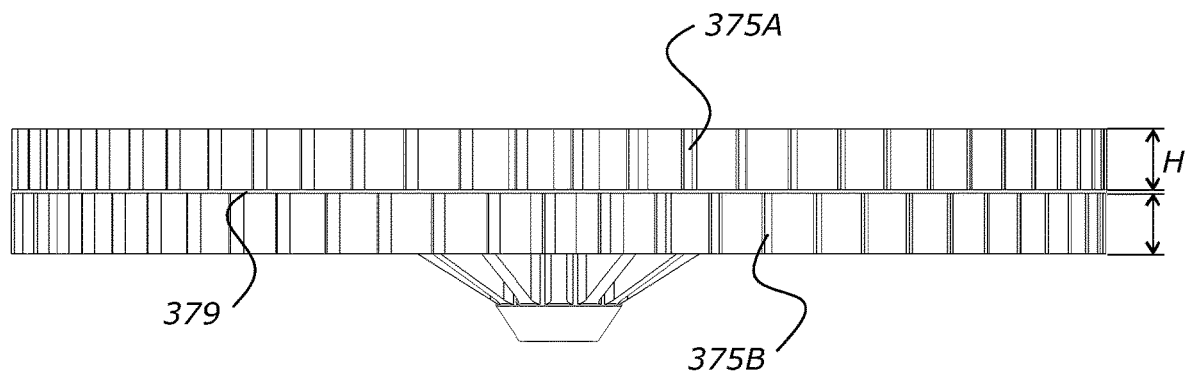
Figure 58:
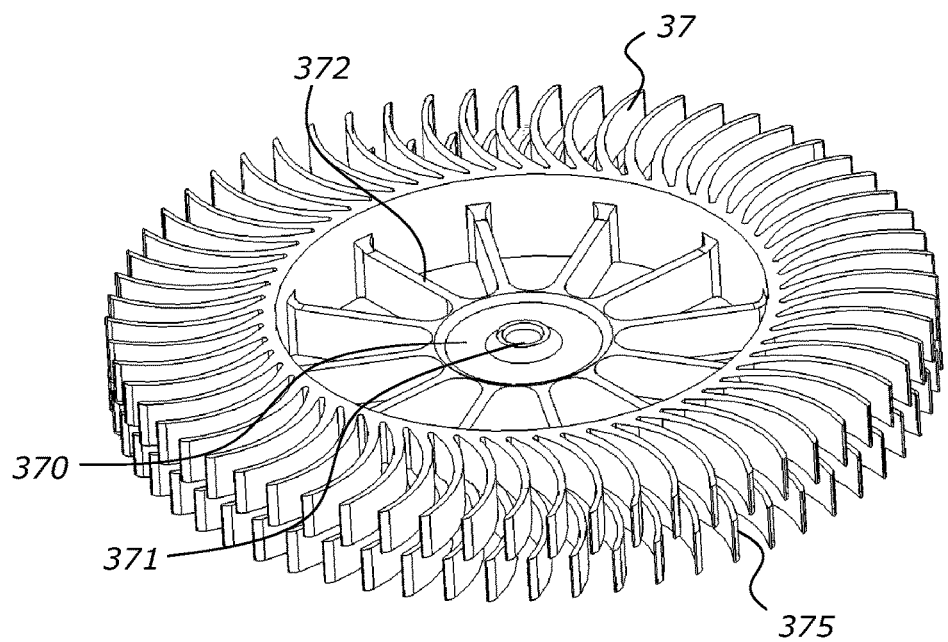
FIGS. 58 and 59 show a perspective view and a top view of another embodiment of an impeller suitable for use with the third embodiment of the regenerative blower.
Figure 59:
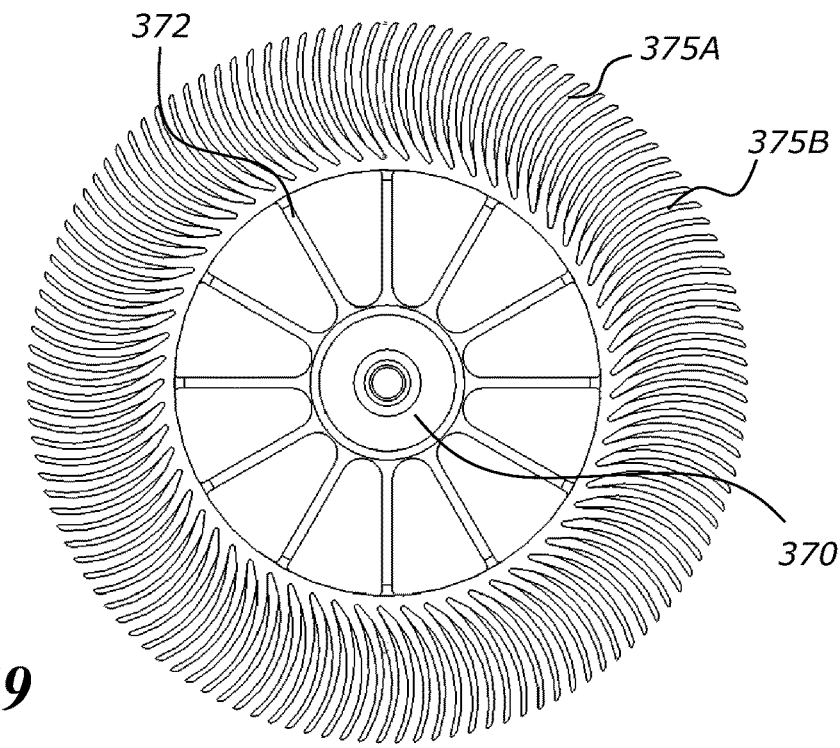

The impeller 315, which is coupled to the shaft 312, is located in and rotates within the impeller channel 345 predominately formed in the top housing 302. The impeller 315 is shown in FIGS. 55 to 57.

The impeller 315 comprises a hub 370 with a central aperture 371 for coupling to a rotor or shaft of a motor. A plurality of spokes 372 project radially from the hub towards an annular ring support 376. An annular impeller support plate 379 extends from the annular ring support 376. A plurality of impeller blades 375 are supported on and extend outwards from the annular ring support 376 and are supported on the annular impeller support plate 379. In the illustrated configuration, the hub 370, spokes 372, annular ring support 376, impeller blades and annular impeller support plate 379 are integrally formed. The annular support plate 379 can provide strength to the impeller blades 375 and can improve pressure and flow performance of the blower. There is an upper row of impeller blades 375A and a lower row of impeller blades 375B. The upper row of impeller blades 375A is rotationally offset from the lower row of impeller blades 375B. Any suitable number of impeller blades could be provided, but preferably in odd number, and more preferably a prime number to reduce blade pass noise, harmonics, resonance and other vibrations. In one non-limiting example, the number of upper and lower impeller blades is the same (for example, 61 blades each). The illustrated impeller 315 includes the annular impeller support plate 379, however in an alternative configuration, (see, e.g., FIG. 58, 59) the annular impeller support plate 379 can be excluded. Removing the annular impeller support plate 379 can reduce the mass and therefore inertia of the impeller 315 if the rigidity and extra strength provided by the annular impeller support plate 379 is not needed.

The lower impeller blades 375B are offset relative to the upper impeller blades 375A so that each lower impeller blade sits between (and more preferably in the middle of the gap between) the corresponding upper impeller blades. As a non-limiting example, the lower impeller blades 375B could be offset/rotated by 2.95° with respect to the upper impeller blades 375A. More generally, the lower impeller blades 375B can be offset by:

$$\theta = \frac{360}{2N} \pm X \text{ degrees, or}$$

$$\theta = \frac{\pi}{N} \pm X \text{ radians}$$

Where θ is the angle that the lower impeller blades 375B are offset relative to the upper impeller blades 375A, N is the number of upper impeller blades 375A and X is an offset angle. When X=0, the lower impeller blades 375B are offset such that they align centrally with each gap between the upper impeller blades 375A. X can be a percentage of $$\frac{360}{2N}.$$

For example, X can be such that X=α×

$$\frac{360}{2N}$$

using the first equation. Therefore, when α=0.1, X is 10% of $$\frac{360}{2N}.$$

α may equal 0, 0.1, 0.2, 0.3, 0.4, 0.5, or may be between 0-0.5, 0-0.1, 0.1-0.2, 0.2-0.3, 0.3-0.4 or 0.4-0.5, for example. Preferably, N is a prime number or an odd number.

Each of the impeller blades 375 are curved in a swept forward/backward manner. As a non-limiting example, the impeller blades 375 could be curved with a circular radius of curvature of between about 8 mm and 13 mm, such as equal to or about 10.81 mm. Although curved blades are used, alternate configurations of the impeller may include straight blades, serpentine blades, convex blades, or another shape as desired. For example, straight blades may be preferred in a blower arranged to operate in two directions (a dual outlet or bi-directional blower). In a variation, a different number of blades a provided on the top to the bottom. For example, 61 blades on the top and 67 blades on the bottom.

Offsetting the upper impeller blades 375A from the lower impeller blades 375B as shown is beneficial in reducing the noise produced by the blower. Reasons for this comprise reducing the impact of the blades encountering the interrupter 325, by further splitting when the upper row and the lower row of impeller blades encounter the interrupter (in comparison to a single "full" row of blades). Furthermore, offsetting the blades can increase the frequency of the noise produced by the blower. Higher frequencies can be easier to attenuate. If pushed high enough, the frequencies can also be outside the audible range (of approximately 20 kHz). Although the blades of this embodiment of the impeller 315 are curved, splitting the blades would reduce the noise produced by impellers with straight blades, or other blade arrangements as well.

Figure 60:
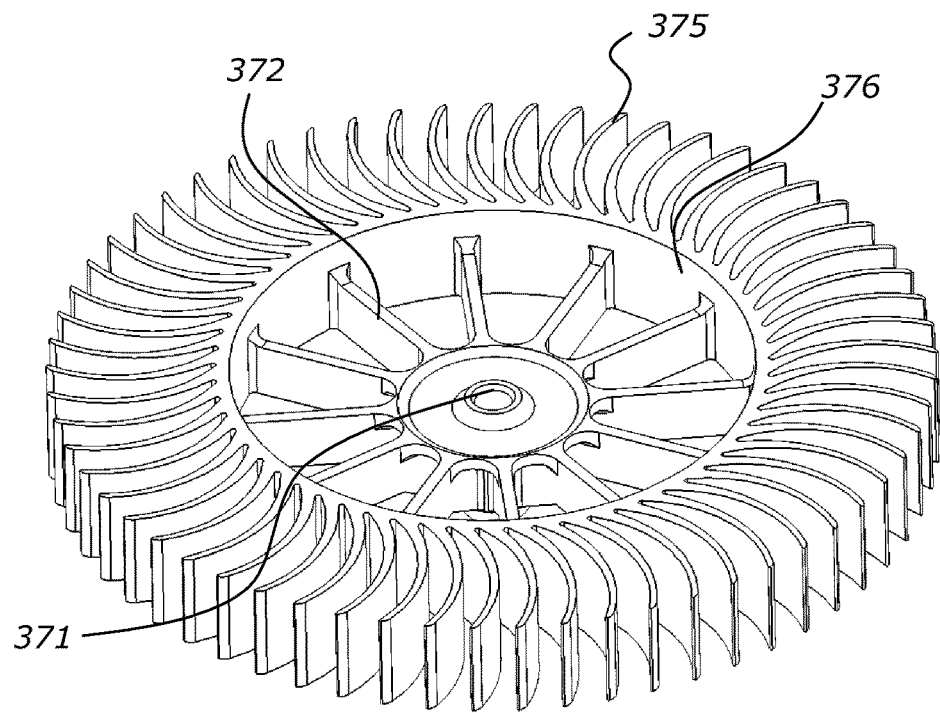
FIGS. 60 and 61 show a perspective view and a top view of another embodiment of an impeller suitable for use with the third embodiment of the regenerative blower.

Referring to FIG. 60, 61, in another configuration, there is only one row of impeller blades 375. Each impeller blade 375 is the height of the annular ring support 376, as opposed to split blades of previous impellers. Therefore each blade spans the full height of the impeller 315.

Each of the spokes 372 are optionally of a height that is less than the combined stacked height of the impeller blades 375/annular ring support 376. This reduces the mass and inertia of the impeller 315. When the impeller 315 rotates, the spokes 372 cause turbulence in the central region of the impeller 315. This turbulence acts as a fluid seal to help 'seal' the central portion of the blower, reducing leak across the central portion of the impeller 315.

The impeller can include a number of central notches, or alternatively, region/s of reduced vertical thickness in the hub and/or spokes of the impeller, between the centre of rotation of the impeller and the blades. These regions of reduced thickness allow the spokes and hub to accommodate the height of the annular ring support, while still reducing the thickness to allow the impeller's mass, and therefore moment of inertia to be reduced. As a result, the impeller requires less energy to operate, and its direction and/or speed can be changed more rapidly.

In one configuration, the impeller is made from a plastic or one or more other polymeric materials. For example, ABS, polycarbonate, Nylon or the like could be used. Also fillers such as carbon or glass fibre could be used. In some configurations, the impeller 315 can be overmolded onto the shaft 312. Alternatively, the impeller 315 can be independently molded and connected to the shaft 312. Alternatively, in another configuration, the impeller 315 can be made from a metal, a composite (e.g. carbon fibre), or another material suitable for a lightweight impeller.

2.4.5 Operation

Figure 62:
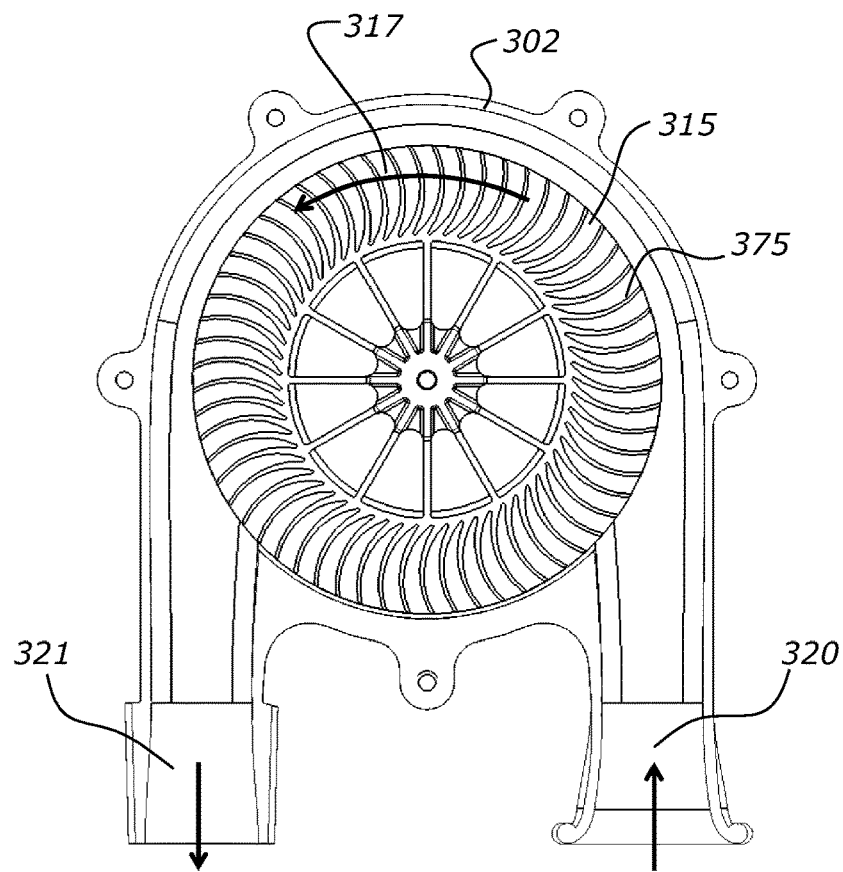
FIG. 62 shows a top view of a cross section of the third embodiment of the regenerative blower illustrating an impeller spinning in a first direction.
Figure 63:
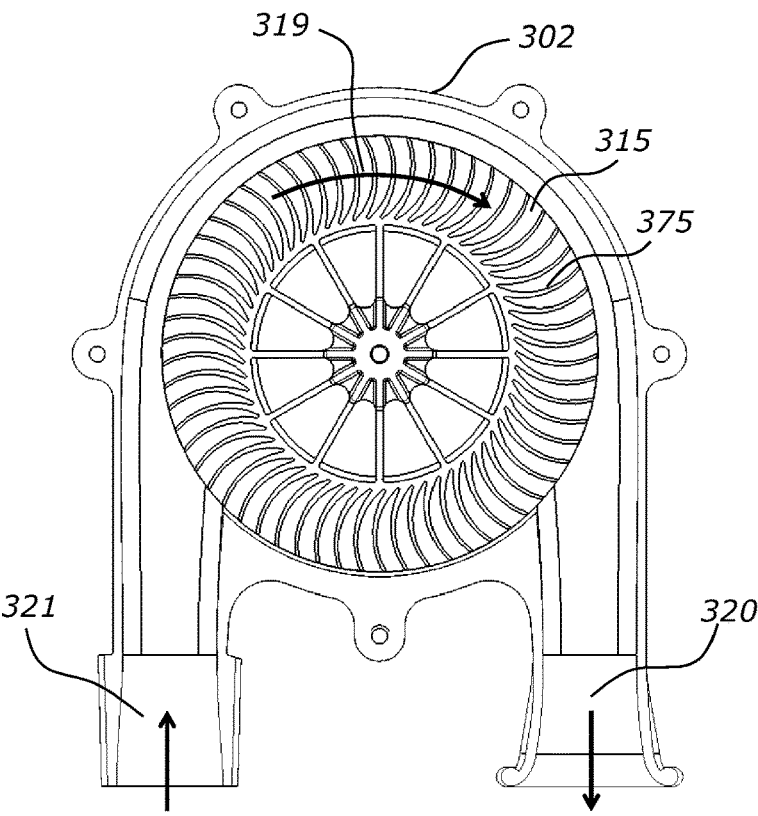
FIG. 63 shows the top view of the cross section of FIG. 62, illustrating the impeller spinning in an opposite direction to that of FIG. 62

Referring to FIGS. 62, 63, in some embodiments, the blower 300 can be used as a dual outlet, reversible or bi-directional blower. In this case, it is more appropriate to refer to the previously described inlet port 320 and outlet port 321 as the first port 320 and second port 321 respectively due to the bi-directional operation of the blower. Energising the motor to rotate the impeller 315 in a first direction of rotation 317 generates a flow of gases from the first port 320, through the housing 301, and out through the second port 321. Energising the motor to rotate the impeller in an opposite second direction of rotation 319 generates a flow of gases through the ports 320, 321 in the opposite direction.

Figure 64:
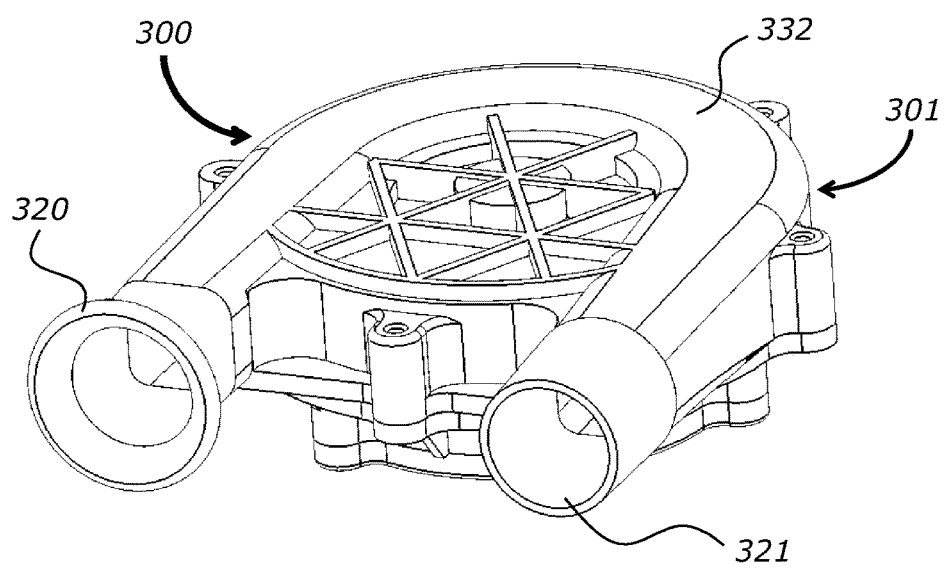
FIG. 64 shows a perspective view of a fifth configuration of the third embodiment of the regenerative blower.

FIG. 62 shows a bottom view of a cross section of the blower 300, showing the impeller 315, top housing 302 and the first direction of rotation 317 of the impeller 315. FIG. 63 shows a view of the cross section of FIG. 64 showing the second direction of rotation 319 of the impeller 315. Any of the impellers of FIGS. 57 to 63 can be used for the dual outlet blower. Alternately, an impeller with straight blades may be preferred for more uniform bi-directional flow behaviour. Alternatively, an impeller with serpentine blades could be provided, which can be beneficial for bi-directional flow where different flow characteristics are desired when flowing in one direction from the other.

2.4.6 Example Dimensions for Third Embodiment

Exemplary, non-limiting, examples of dimensions of the third embodiment will be detailed below.

In one, non-limiting, example of dimensions for the housing are:

A length L (as shown in FIG. 40) of between about 75 mm and 105 mm, such as equal to or about 85 mm.

Figure 36:
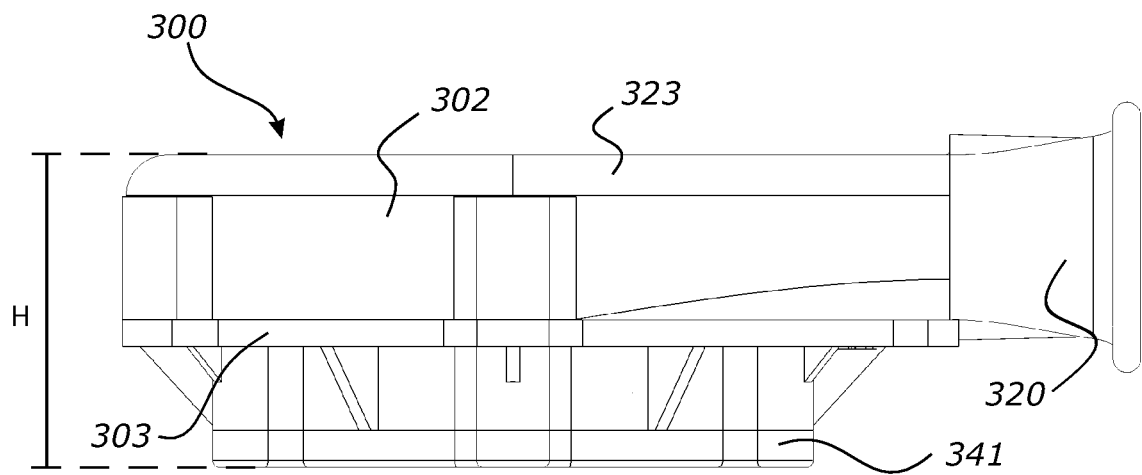
Figure 37:
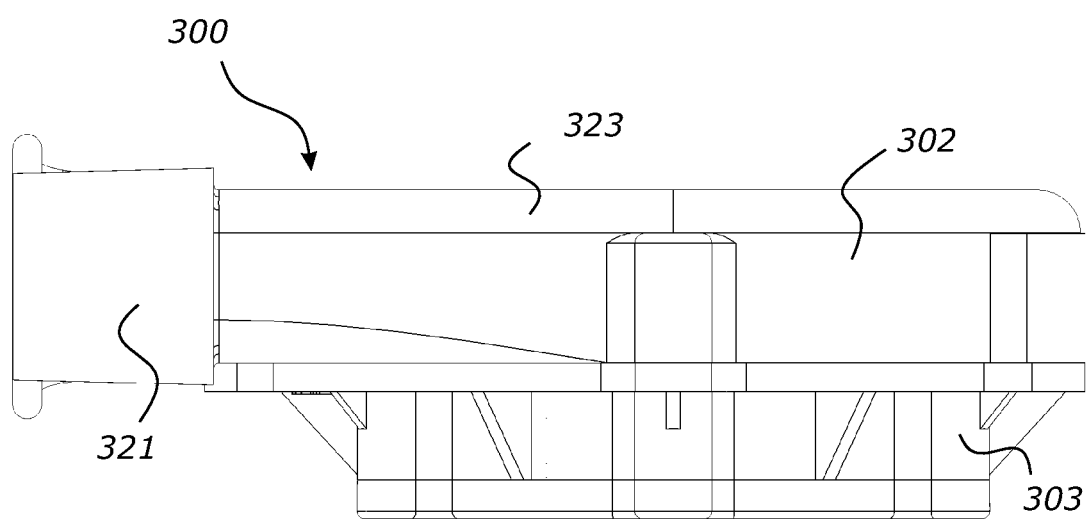
Figure 38:
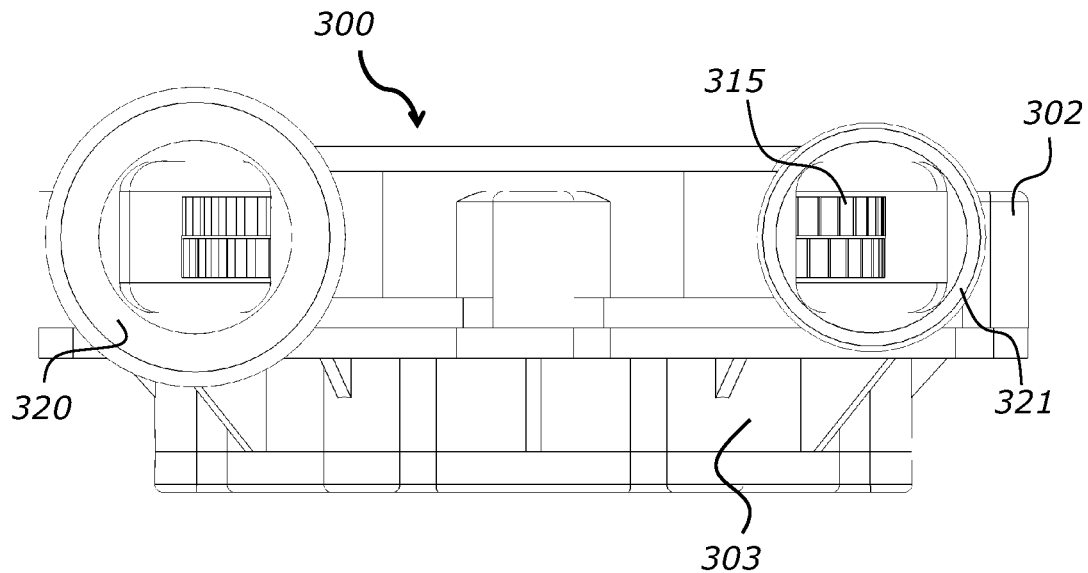
Figure 39:
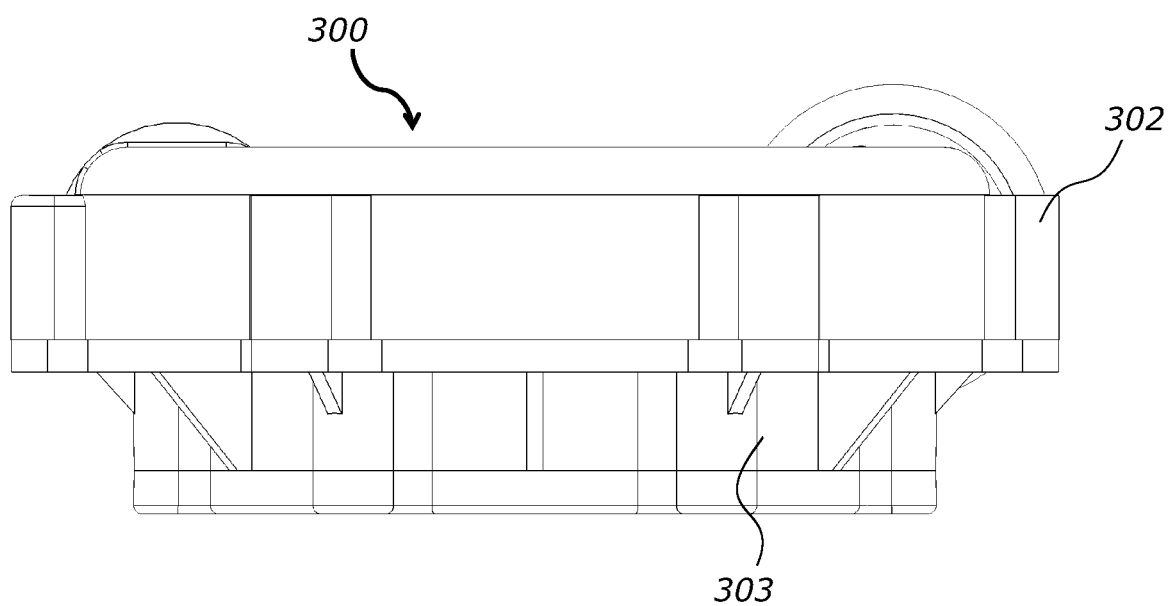

A height H (as shown in FIG. 36) of between about 25 mm and 45 mm, such as equal to or about 34.25 mm In one, non-limiting example of the interrupter 325, an arc length between point G1 and point G2, as identified in FIG. 45, can be between about 35 mm to 55 mm, and for example is or is about 45.0 mm. An arc length between point H1 and point H2 can be between about 40 mm to 60 mm, and for example is or is about 50.28 mm. An angle G can be between about 145° to 165°, and for example is or is about 155°, and an angle H can be between about 80° to 100°, and for example is or is about 89.85°. A ratio of the angles, G:H can be between about 2:1 to 1.4:1, and for example is or is about 155:89.85 or 1.725:1.

The impeller 315 has dimensions suitable to be assembled with the other features described and achieve the operation functions as described herein. In one non-limiting example, the impeller 315 has a diameter of between about 60 mm and 80 mm, such as equal to or about 69.69 mm. The impeller blades 375 have a blade thickness T (shown in FIGS. 56 and 61) ranging from of between about 0.5 mm and 1.5 mm (e.g. equal to or about 1 mm) at the root of each blade, to between about 0.25 mm and 0.75 mm (e.g. equal to or about 0.5 mm) at the tip of each blade. The impeller 315 of FIGS. 55 to 57 has a blade height H (from the annular impeller support plate 379) of between or about 3 mm and 4.5 mm, such as equal to or about 3.875 mm. The annular impeller support plate 379 height itself is between about 0.1 mm and 0.4 mm, such as equal to or about 0.25 mm, so the impeller 315 of FIGS. 55 to 57 has a total height of between about 6.1 mm and 9.4 mm, such as equal to or about 8 mm.

As a non-limiting example, the lower impeller blades 375B could be offset/rotated by or about 2.95° with respect to the upper impeller blades 375A. Alternately, each of the lower impeller blades 375B could be offset/rotated by an angle θ with respect to the upper impeller blades 375A according to:

$$\theta = \frac{360}{2N} \pm X \text{ degrees, or}$$

$$\theta = \frac{\pi}{N} \pm X \text{ radians}$$

Where θ is the angle that the lower impeller blades are offset relative to the upper impeller blades, N is the number of upper impeller blades and X is an offset angle, as previously described. When X=0, the lower impeller blades 375B are offset such that they align centrally with each gap between the upper impeller blades 375A. X can be a percentage of $$\frac{360}{2N}.$$

For example, X can be such that X=αx $$\frac{360}{2N}$$

using the first equation. Therefore, when α=0.1, X is 10% of $$\frac{360}{2N}.$$

α may equal 0, 0.1, 0.2, 0.3, 0.4, 0.5, or may be between 0-0.5, 0-0.1, 0.1-0.2, 0.2-0.3, 0.3-0.4 or 0.4-0.5, for example. Preferably, N is a prime number or an odd number.

Each of the impeller blades 375 are curved in a swept forward/backward manner. As a non-limiting example, the impeller blades 375 could be curved with a circular radius of curvature of by between about 8 mm and 13 mm, such as equal to or about 10.81 mm.

Figure 42:
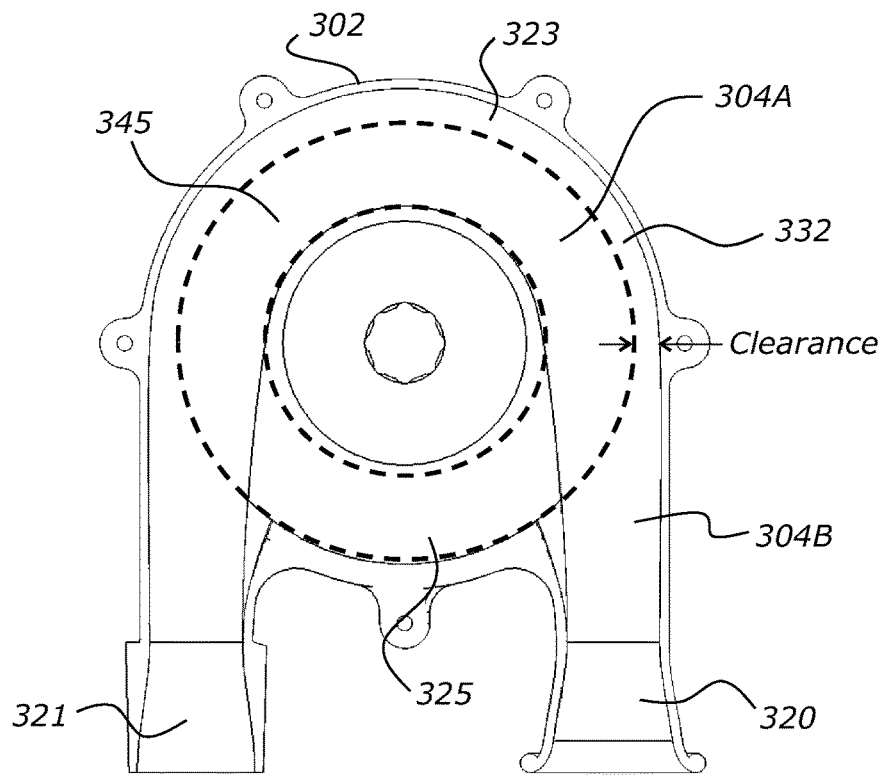

Referring to FIGS. 34, 35, 42, the radial clearance between the impeller blades 375 and the airflow channel 332 outer perimeter is between about 5 mm and 7 mm, such as equal to or about 6.15 mm. The radial clearance is the distance between the tips of the impeller blades 375 and the inner surface of the airflow channel 332. In other words, the ratio of the radial clearance to the impeller blade length (e.g. 13.23 mm in the radial direction) is between about 1:2 to 1:3, such as equal to or about 6.15:13.23 or 1:2.15. The ratio of the radial clearance to the impeller diameter (e.g. 69.69 mm) is between about 1:10 to 1:14, such as equal to or about 6.15:69.69 or 1:11.33. The channel 304 is between about 16 mm and 23 mm, such as equal to or about 19 mm in width. That is, the width of the impeller channel 345 and the airflow channel 332 together can be approximately 19 mm. The radial clearance is therefore between about 20% and 43% (e.g. equal to or about 32.3%) of the width of the annular channel. The specified radial clearance can be beneficial in improving the performance of the blower.

2.4.7 Housing—Configuration #2

Figure 65:
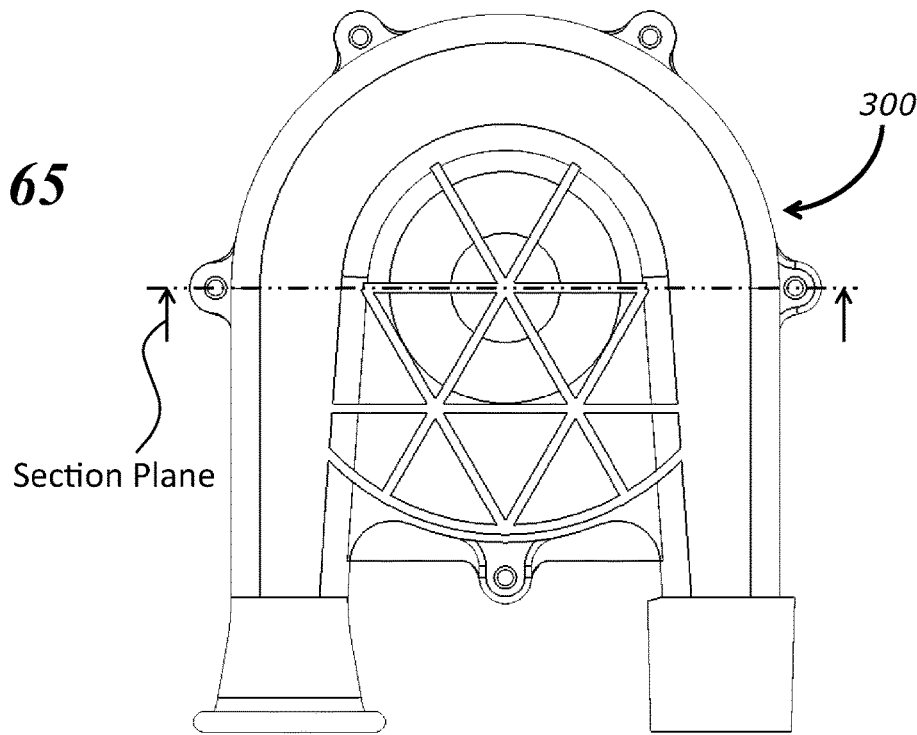
FIG. 65 shows a top view of the fifth configuration of the third embodiment of the regenerative blower.
Figure 66:
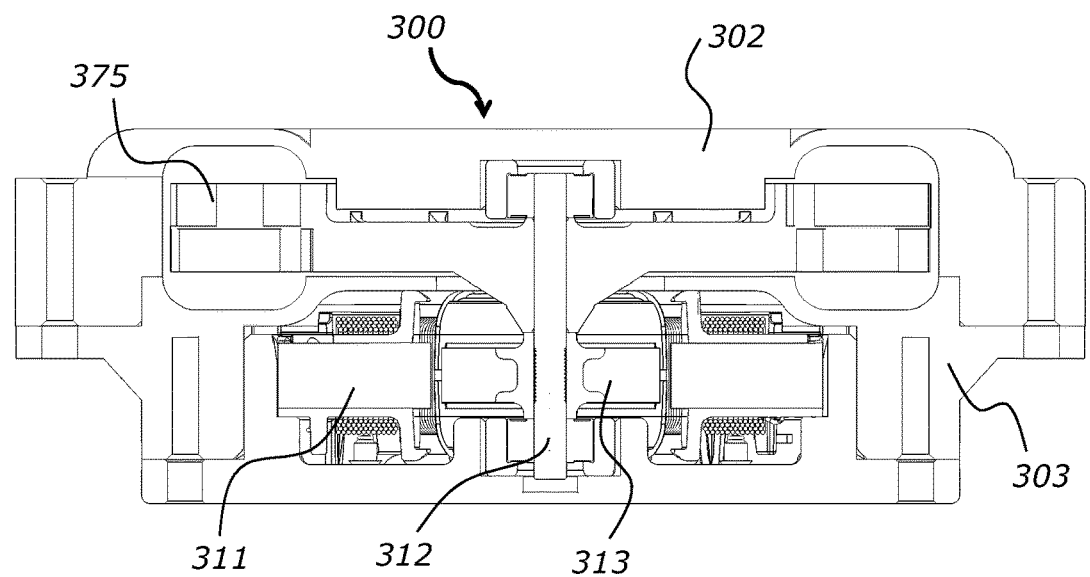
FIG. 66 shows an elevation view of a cross-section of the fifth configuration of the third embodiment of the regenerative blower.
Figure 67:
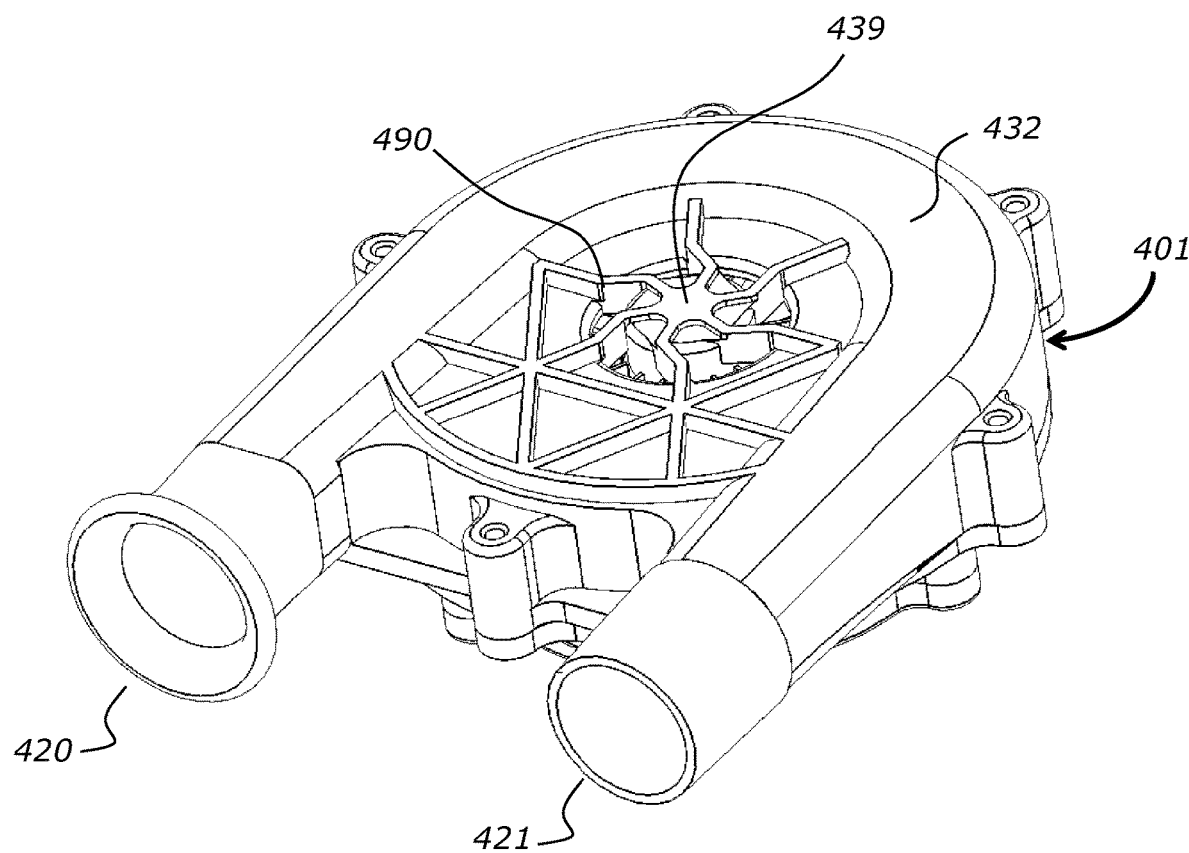
FIG. 67 shows a top perspective view of a regenerative blower according to a fourth embodiment.

FIGS. 64 to 66 show a second configuration of the third embodiment of the regenerative blower.

The second configuration of the third embodiment differs from the first configuration in that the width of the channel 104 is reduced. That is, the combined width of the impeller channel 345 and airflow channel 332 is reduced. Referring to the structure established with reference to FIG. 1, the second configuration of the third embodiment can be said to lack a lateral channel. As a result, the radial clearance (distance between the tips of the impeller blades 375 and the interior surface of the airflow channel 332) is substantially reduced. The radial clearance can be reduced to a distance of the order of magnitude of the manufacturing tolerances of the blower housing 101 and/or the impeller 315. In some cases this can be between 0.5-1 mm. This provides for reduced blower size and reduced power consumption in relatively low flow operation—e.g. below about 60 L/min 2.5 Fourth Embodiment of a Regenerative Blower FIGS. 67 to 78 show a regenerative blower according to a fourth embodiment. Features of the fourth embodiment that are the same or similar to those of the third embodiment or other embodiments may not be described fully or at all, but it will be appreciated by those skilled in the art that relevant portions of the description relating the first and second embodiment or any other embodiments described herein apply to this embodiment, where appropriate.

2.5.1 Overview

Figure 68:
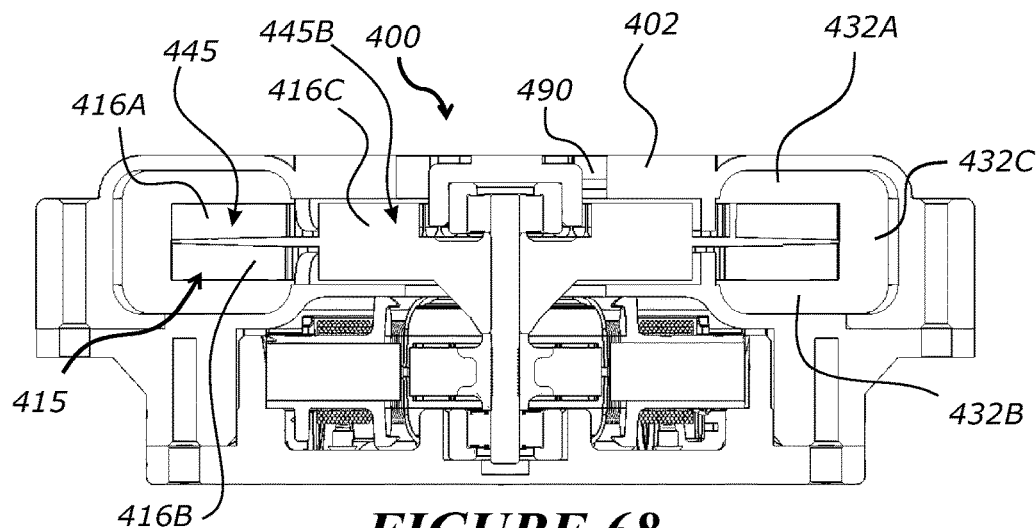
FIG. 68 shows a cross-sectional view of the fourth embodiment of the regenerative blower.
Figure 69:
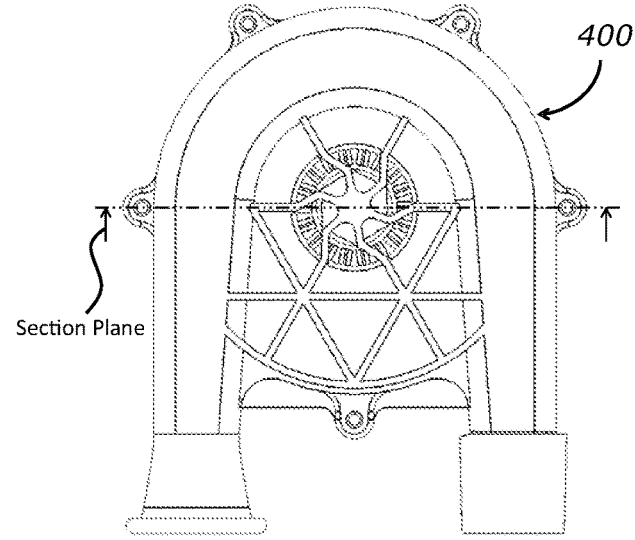
FIGS. 69 and 70 shows another cross-sectional view of the fourth embodiment of the regenerative blower.
Figure 70:
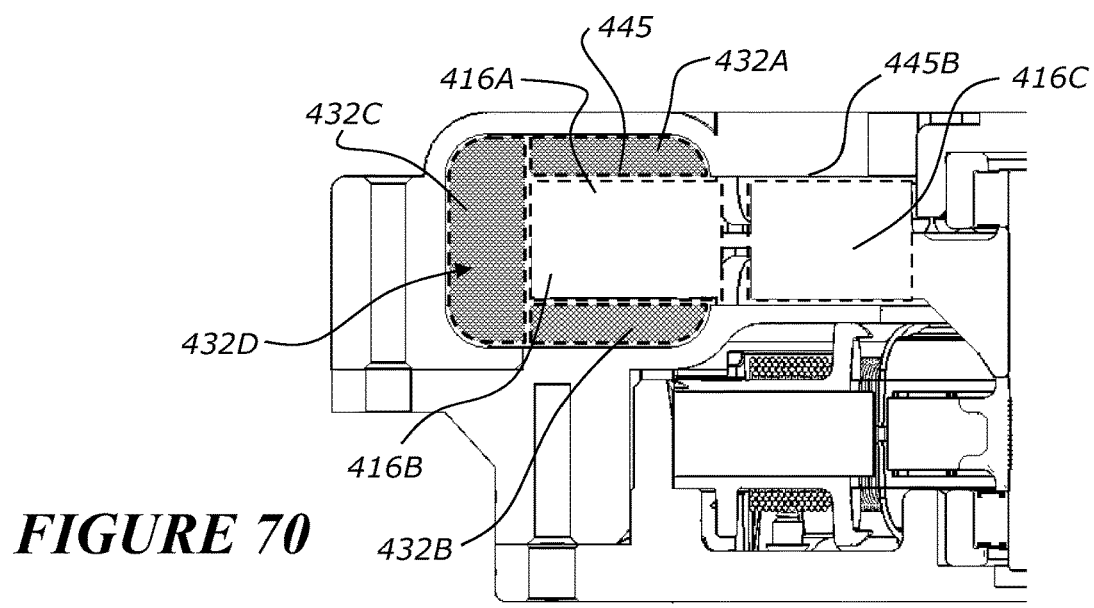
Figure 71:
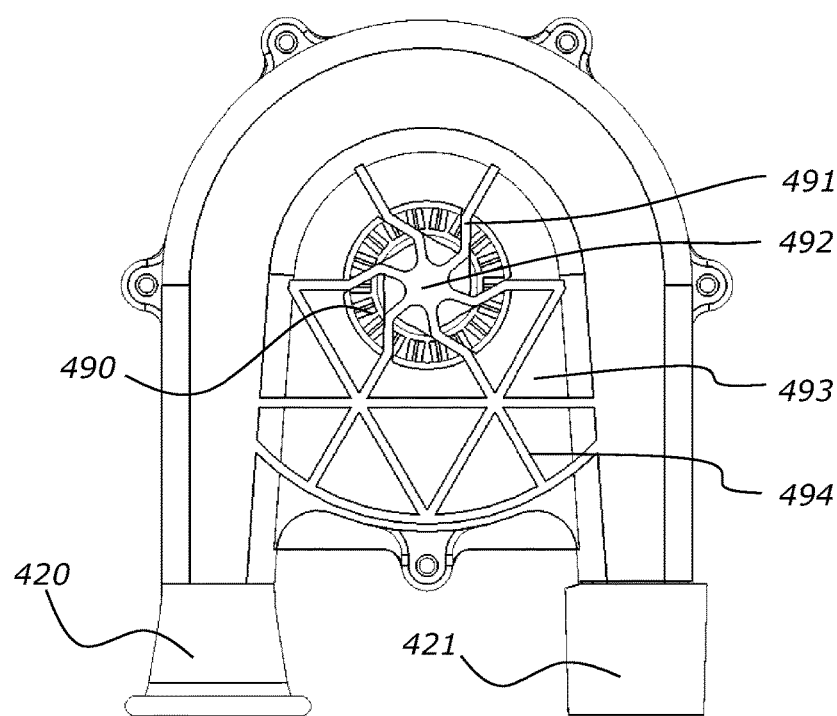
FIG. 71 is a top view of the fourth embodiment of the regenerative blower.

Referring to FIGS. 67 to 73, like the third embodiment, the fourth embodiment has housing 401 with an first port 420, second port 421 and channel 404. In the illustrated configuration, the first port 420 is the inlet port and the second port 421 is the outlet port, as under usual operation, the impeller 415 is rotated in a clockwise direction when the blower 400 is viewed from above as in FIG. 71. Reversing the direction of impeller rotation will reverse the purpose of each of the ports however. The channel 404 of the fourth embodiment has a different topology to that of the third embodiment, and the blower has a different impeller configuration and an additional inlet/outlet port 490. Referring to FIG. 68, the channel 404 comprises an impeller channel 445, and also upper 432A, lower 432B and lateral 432C airflow channels as previously described with reference, for example, to FIG. 1. The upper airflow channel 432A, lower airflow channel 432B and the lateral airflow channel 432C together form the airflow channel 432 of the blower 400. The housing 401 also defines an outer impeller channel 445 and an inner impeller channel 445B. The outer impeller channel 445 at least partially coincides with the airflow channel 432. The differences will now be explained in further detail.

2.5.2 Housing—Configuration #1

Referring to FIGS. 69, 70, 71, 72 the top housing 402 comprises the port 490. The port 490 can be in the form of a top housing port 490. The top housing 402 has a central hub 439 with a recess 438 for supporting a shaft bearing. The central hub 439 is supported in place by way of a plurality of optionally angled spokes 491 extending from a central hub 492 above the central recess 438. The angled spokes 491 deviate from radial lines projecting from the origin of the spokes 491 on the central hub 439. Angling the spokes with respect to radial lines projecting from the origin of the spokes 491 on the central hub can help reduce noise produced by the blower, for example noise produced by impeller blades passing the spokes 491. The top housing 402 includes a top plate 493 that extends between two limbs of the airflow channel 432. The top plate 493 also comprises a triangular lattice 494 which can stiffen the structure. The top housing port 490 is provided by way of apertures 490 between the central hub 439 and the top plate 493 of the top housing. The apertures 490 are formed by way of angled spokes 495 that extend from the central hub 439 through an annular aperture to the top plate 493, thus splitting the annular aperture into a plurality of airflow apertures forming the top housing port 490. The top housing port 490 allows air to be drawn in from the atmosphere or expelled to the atmosphere, depending on the operation of the blower. Therefore, the top housing port 490 can be an additional (third) port, that can be an additional inlet or outlet port. When operating as an inlet, the air from the top housing port 490 is directed into the airflow channel 432 via the inner impeller channel 445B to combine with the air from the (first) inlet as previously described. Under relatively high flow conditions, the top housing port 490 acts like another inlet (a second inlet (or a third inlet if you consider the bottom housing aperture 448 an inlet)), allowing additional air to be drawn into the blower, improving the high flow performance. Under relatively low flow conditions, the top housing port 490 acts like another outlet, with an amount of air drawn into the blower being blown out through the top housing port 490.

Figure 72:
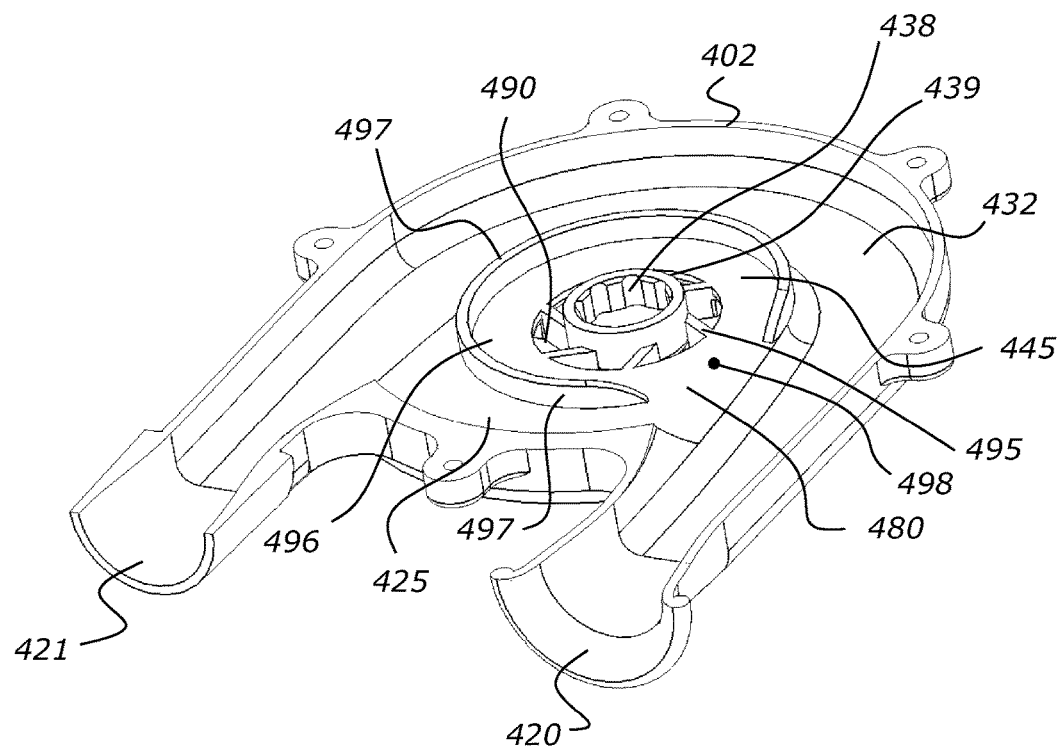
FIG. 72 is a bottom perspective view of a cross-section of a top housing of the fourth embodiment of the regenerative blower.
Figure 73:
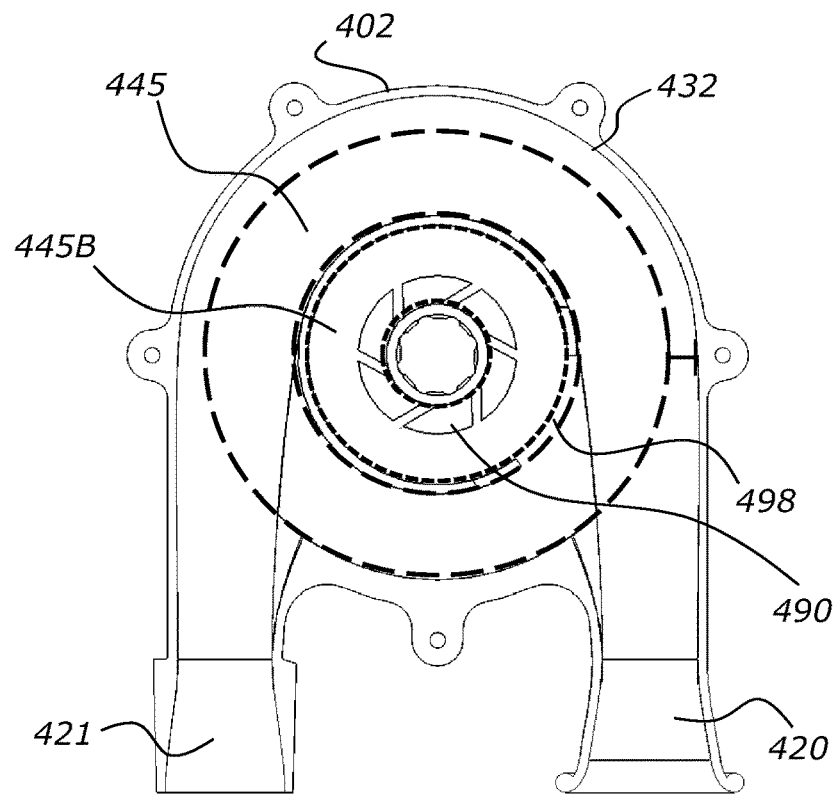
FIG. 73 is a bottom view of the cross-section of FIG. 71.
Figure 74:
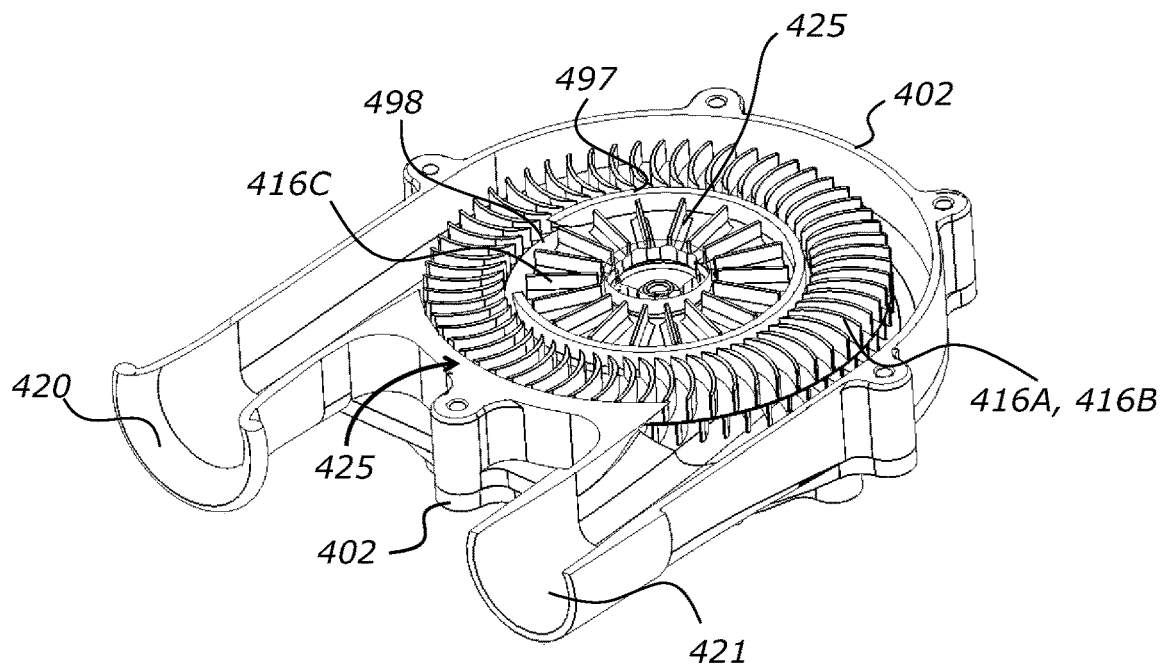
FIG. 74 is a bottom perspective view of a cross-section of the fourth embodiment of the regenerative blower.
Figure 75:
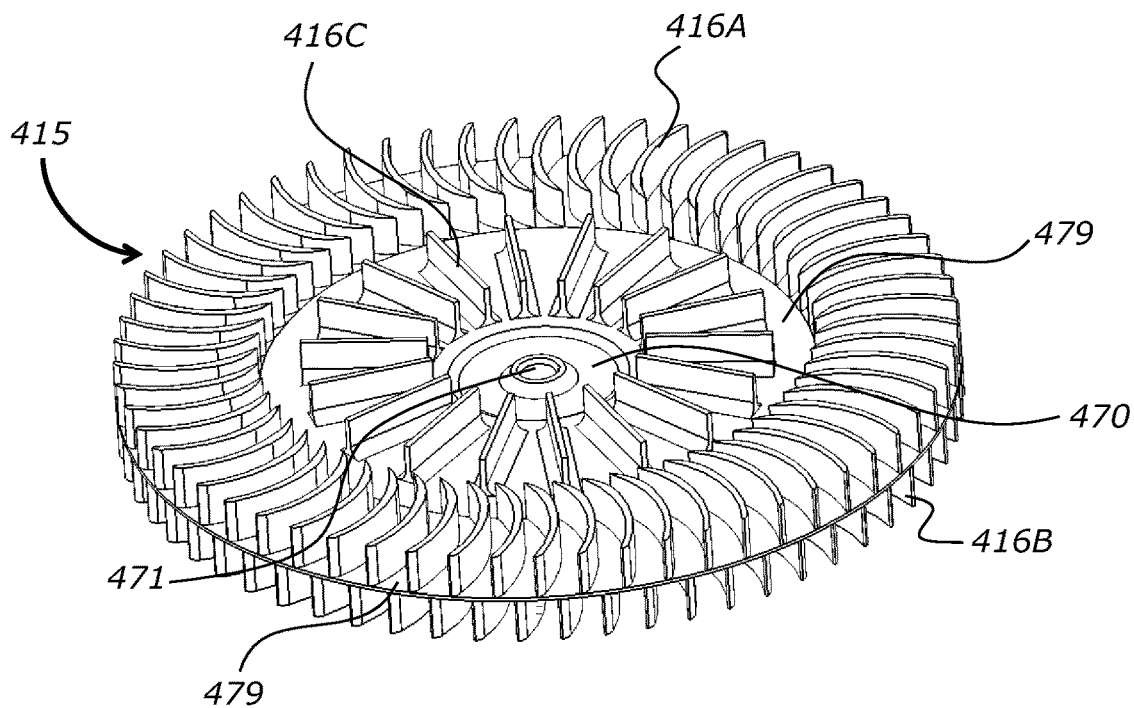
FIG. 75 shows a top perspective view of an impeller suitable for use with the fourth embodiment of the regenerative blower.
Figure 76:
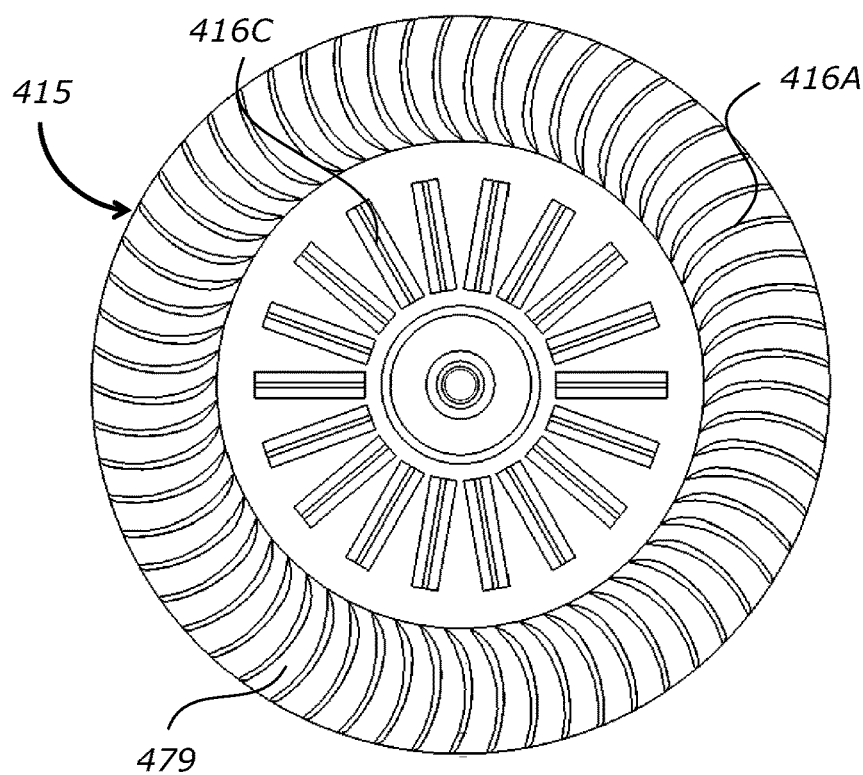
FIG. 76 shows a top view of the impeller of FIG. 75.

Referring to FIG. 72, which shows the interior region of the top housing 402, the top housing 402, in addition to an having an arcuate upper airflow channel 432A, lateral airflow channel 432C, part of the lower airflow channel 432B and outer impeller channel 445 as per the third embodiment, further comprises an inner annular channel, which provides an inner annular impeller channel 445B. The internal impeller channel 445B is formed by way of a channel isolator 497 formed as an arcuate wall 497 disposed on the top shelf 480 and extending concentrically around the central hub 439. The arcuate wall 497 is broken to provide an air flow opening 498 between the inner impeller channel 445B and the: a)(outer) upper/lower/lateral airflow channels, and/or b) the outer impeller channel 445. The channel isolator 497 isolates the air flow from the inner impeller channel 445B and outer airflow channels, except for the air flow path through the air flow opening 498. Referring to FIG. 72, an impeller 415 is disposed in the inner 445B and outer 445 impeller channels, as will be described later. In other words, the impeller 415 occupies the inner impeller channel 445B and the outer impeller channel 445.

As the behaviour of the top housing port 490 is variable, (acting as an inlet when running at high flow, and an outlet when running at high pressure) it can be beneficial to use a one-way valve to control the behaviour of the top housing port 490. In a variation, optionally, a one-way valve ("check-valve") can be incorporated into the top housing port 490 to make port act only as an inlet. Examples of a one way valves that can be used include mechanical valves, or fixed-geometry passive valves such as a Tesla Valve. Incorporating the one-way valve improves the performance of the blower in both low flow (high pressure) conditions, as leak through the port is no longer able to occur, or is at least reduced, and high flow (low pressure) conditions, as the port is able to be used as an inlet to draw in additional air. Such a valve can also be combined with a one-way valve also covering the bottom housing apertures 448 so that they act only as an inlet as well. This improves pressure performance of the blower.

2.5.3 Impeller—Configuration #1

Referring to FIGS. 75 to 78, the impeller 415 comprises a central hub 470 with a central aperture 471 for connection of the impeller 415 to the motor shaft 412. A circular plate 479 extends from the hub 470. Extending from the hub 470 and disposed on the circular plate 479 is a plurality of, optionally straight, inner impeller blades 416C. The inner impeller blades 416C are of constant height and extend radially across the circular plate 479. The inner impeller blades 416C are shaped with a generally rectangular configuration, and extend from a flared base on the circular plate 479 to tips of uniform thickness. There is also an annular ring of curved outer impeller blades 416A, 416B disposed on the outer perimeter region of the plate, arranged in two rows in an offset manner and separated by the circular plate 439 (web/shroud), like that for the third embodiment. The outer impeller blades 416A/416B are arranged to rotate within the outer impeller channel 445 of the housing 401, and the inner impeller blades 416C are arranged to rotate within the inner impeller channel 445B, driven by the motor via the shaft 412. The outer impeller channel 445 allows flow behaviour as previously described. The inner impeller channel 445B can allow flow behaviour like that within a volute of a centrifugal blower. The inner impeller channel 445B is fluidly connected to the outer airflow channels and outer impeller channel 432 via the air flow opening 498. The straight inner impeller blades 416C provide an airflow characteristic of a centrifugal blower in the inner impeller channel 445B prior to air passing through the air flow opening of the channel isolator 497 into the outer impeller channel 445.

The circular plate 479 acts as a strengthening and/or rigidity providing member to support the outer impeller blades 416A, 416B and the inner impeller blades 416C. The circular plate 479 spans the length of the outer impeller blades 416A, 416B. In some configurations, it may be beneficial to reduce the profile of the circular plate 479, so that it only spans a portion of the length of the outer impeller blades 416A, 416B. The modified circular plate 479 would still provide strength and/or rigidity to the impeller 415; however the reduced material would produce a lower mass impeller with a lower moment of inertia. This could be beneficial for rapid impeller control or direction change.

Figure 77:
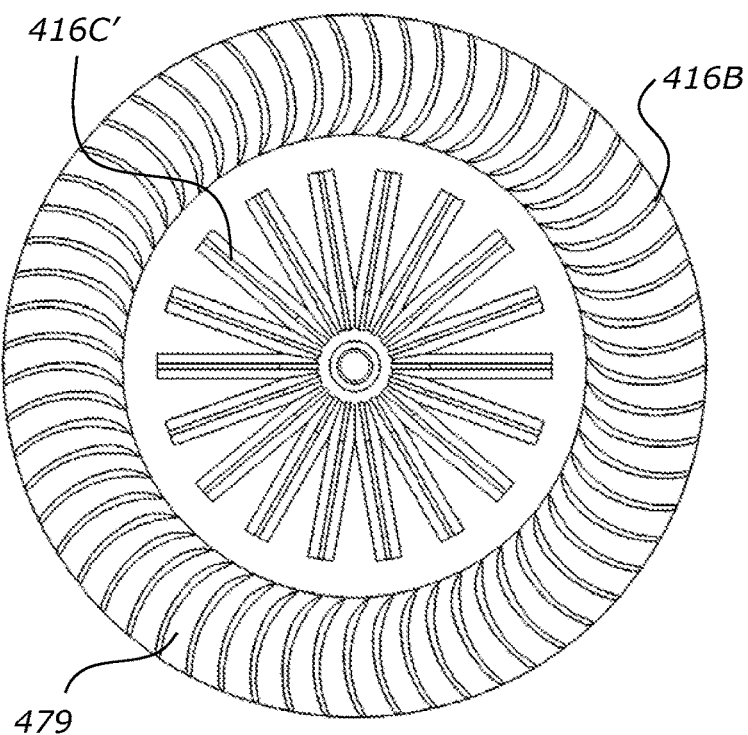
FIG. 77 shows a bottom view of the impeller of FIG. 75.
Figure 78:
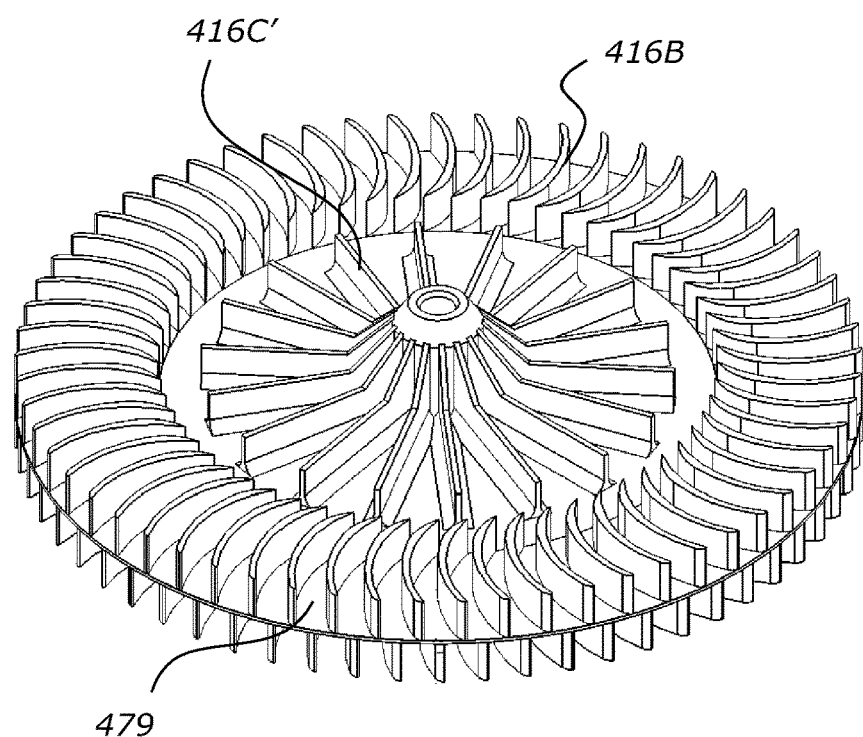
FIG. 78 shows a bottom perspective view of the impeller of FIG. 75

FIG. 78 shows a bottom perspective view of the impeller 415. FIG. 77 shows a bottom view of the impeller 415. The impeller comprises a set of bottom inner impeller blades 416C' with a varied height on the underside of the circular plate 479. Referring to FIG. 78, the central hub 470 and aperture extend downwards from the underside of the circular plate 479. The bottom inner impeller blades 416C' began by extending from the hub at the full height with each blade height then ramping down at an angle to a lower constant height at a distance from the central hub 470. The remainder of the height is constant in the radial direction until the end of the bottom inner impeller blade 416C'.

2.5.4 Operation

In use, rotation of the outer impeller blades 416A, 416B (in a clockwise direction when referring to the top view of FIG. 71) draws air through the tangential inlet port 420. Additionally, rotation of the inner impeller blades 416C in the inner impeller channel 445B draws in air through the top housing inlet port 490 into the inner impeller channel 445B. The inner impeller blades 416C rotate to pressurize the air drawn from the top housing port 490 prior to its entry into the outer impeller channel 445. The pre-pressurised air passes through the air flow opening 498 in the arcuate wall (channel isolator 497) to combine in the airflow channel 432 and outer impeller channel 445 with air drawn directly from the tangential inlet port 420. The air is then pressurized in the channel 404 by rotation of the outer impeller blades 416A, 416B and directed through the outlet port 421. The channel isolator 497 forms part of an interrupter 425 and acts in a similar manner to the hub 339 in the third embodiment, to interrupt flow leaking from the outlet port 421 to the inlet port 420, in addition to flow leaking from the outer airflow channel 332 to the inner impeller channel 445B.

Rotating the motor in an opposing direction can change the direction of airflow in the blower, such that it is a reversible blower, or a dual outlet blower.

Similar to the first embodiment, the fourth embodiment optionally can comprise a bottom housing aperture large enough for the rotor to fit through to simplify and/or reduce the cost of the manufacturing process. Alternatively, the bottom housing aperture of RG4 can be of reduced size as disclosed for the first embodiment.

2.6 Fifth Embodiment of a Regenerative Blower

FIGS. 79 to 87 show a regenerative blower according to a fifth embodiment. This blower is of a reduced size compared to the other embodiments.

Features of the fifth embodiment that are the same or similar to those of the fourth embodiment or other embodiments may not be described fully or at all, but it will be appreciated by those skilled in the art that relevant portions of the description relating the first and second embodiment or any other embodiments described herein apply to this embodiment, where appropriate.

Like the other embodiments, the fifth embodiment blower 500 has a housing 501 with an inlet port 520, outlet port 521 and channel 504. The channel 504 comprises an upper airflow channel 532A and a lower airflow channel 532B. The channel 504 also comprises an impeller channel 545. Again the impeller 515 rotates within the impeller channel 545. However, there are differences from the other embodiments.

2.6.1 Housing

Figure 79:
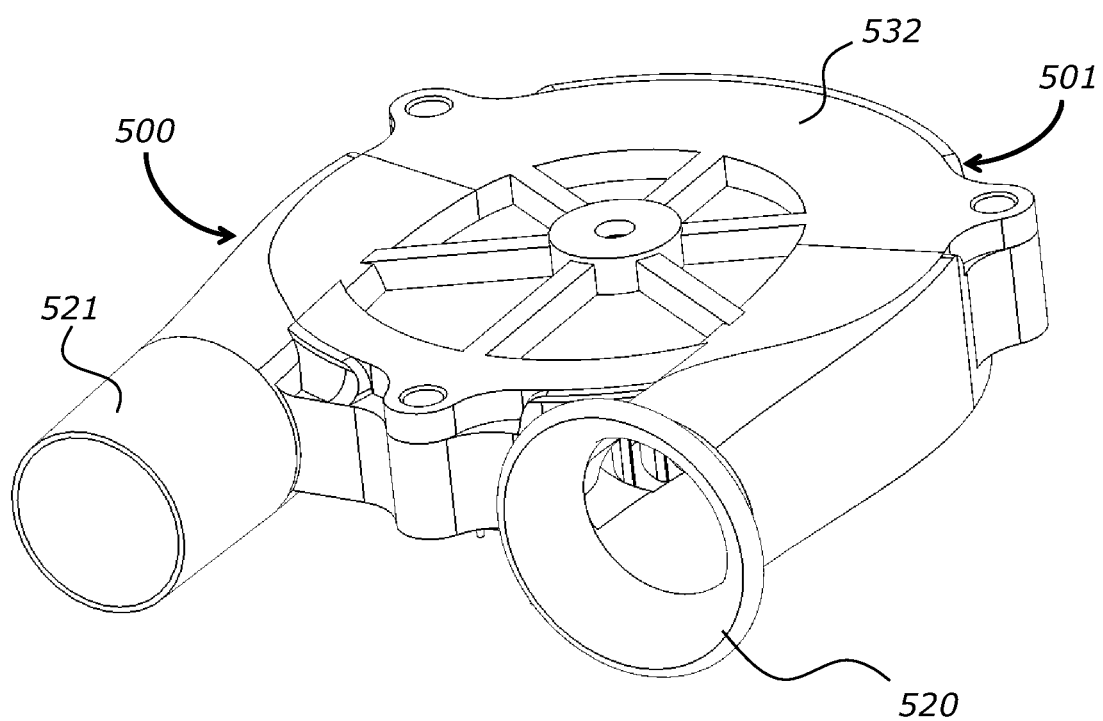
FIG. 79 shows a top perspective view of a regenerative blower according to a fifth embodiment.

Referring to FIG. 79, the top housing 502 couples with the bottom housing 503. The top housing 502 comprises a plateau/shelf 580 that comprises a central hub 539 with an aperture or hole 538 for receiving a motor shaft 512 bearing. The housing 501 defines a channel 504. The channel 504 comprises an impeller channel 545, an upper airflow channel 532A and a lower airflow channel 532B. The top housing 502 at least partially defines the upper airflow channel 532A.

Figure 80:
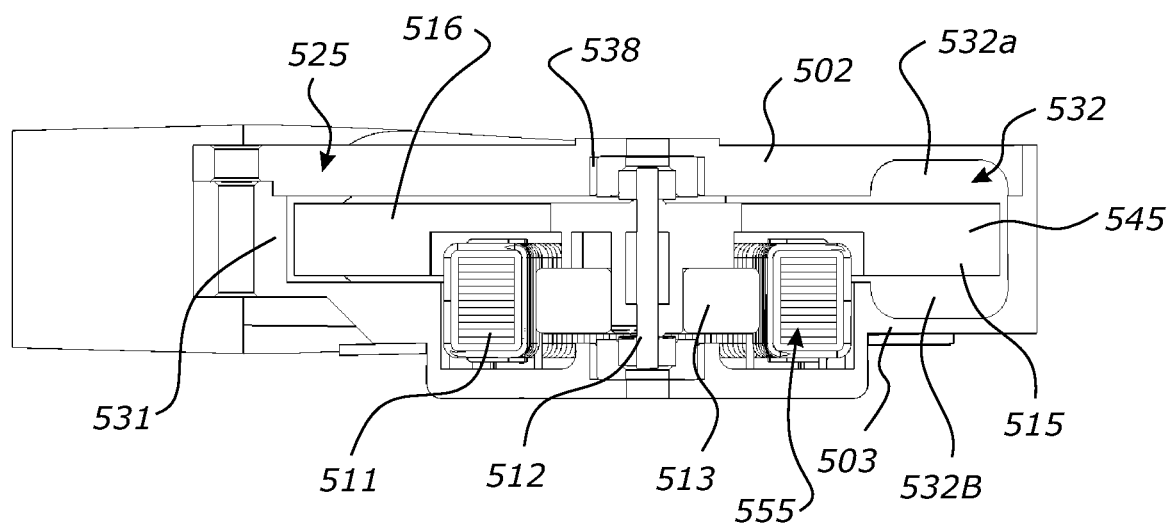
FIG. 80 shows a cross-sectional view of the fifth embodiment of the regenerative blower.
Figure 80:
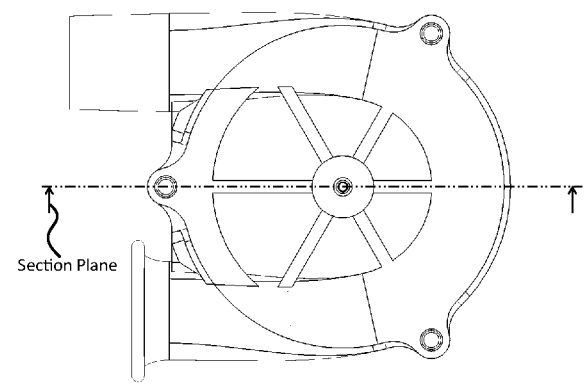
Figure 81:
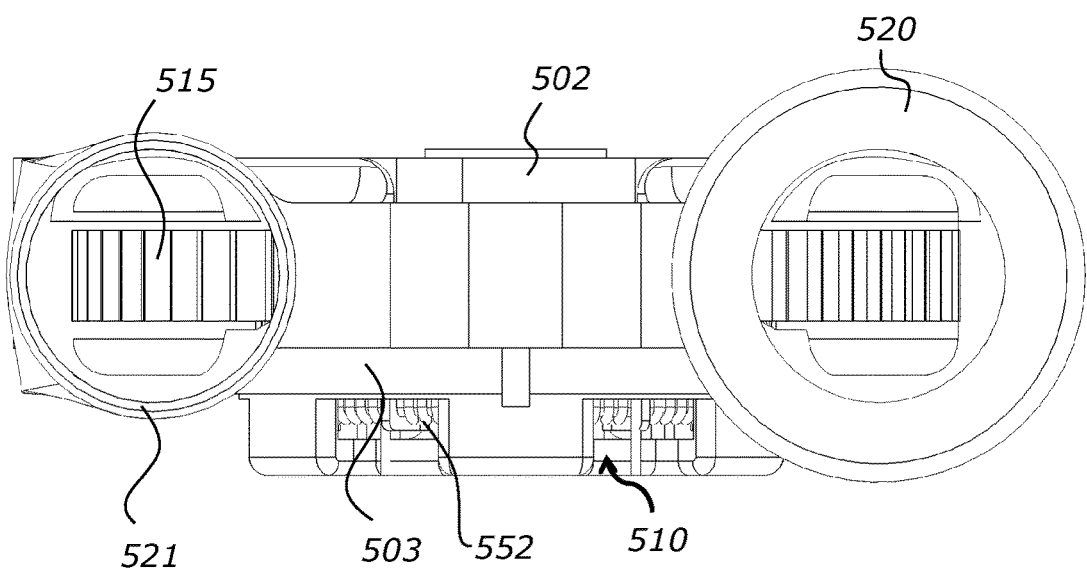
FIGS. 81-84 show elevation views of the fifth embodiment of the regenerative blower.
Figure 82:
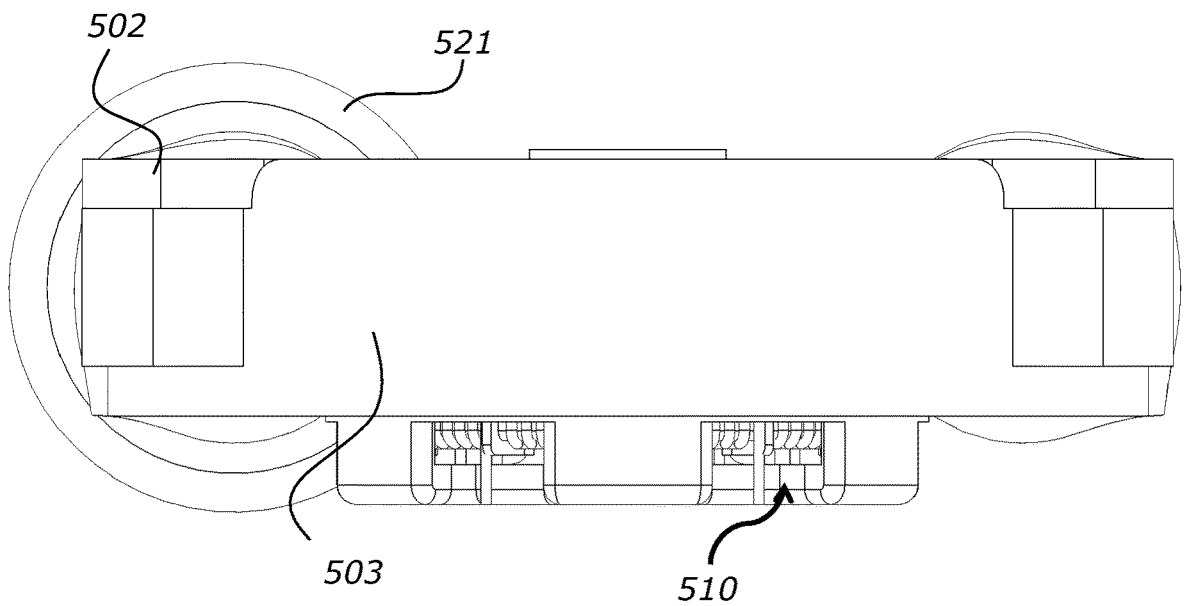

Referring to FIG. 80, the housing 501 also has a different configuration to other embodiments. Rather than having a bottom housing and a separable bottom housing cap, the bottom housing 503 is a single piece. The bottom housing 503 has a perimeter wall that is formed to provide the predominant portion of the lower airflow channel 532B, and part of the upper airflow channel 532A (which forms the upper airflow channel in conjunction with the top housing 502). The bottom housing 503 has a recessed bottom region 555 to provide an internal cavity/interior region for receiving the motor assembly 510. There is no plate separating the motor from the impeller 515. This means that the bottom housing aperture 548 (as defined in previous motors) is in effect the same size as the motor. The removal of the plate separating the motor from the impeller 515 allows the vertical dimension or vertical thickness of the blower 500 to be reduced. A smaller motor assembly 510 is used when compared to previously described blowers. The bottom housing 503 has a plurality of apertures in the base 552 (equivalent function to the bottom housing cap apertures (e.g. 352) of the previous embodiments) for facilitating access to and allowing airflow through the motor assembly 510.

The channel's 504 cross-sectional width formed by the top housing 502 and the bottom housing 503 is reduced compared to the other embodiments. This is shown by the lack of a significant radial clearance between the tip of the impeller 515 with respect to the inner surface of the channel 504 outer wall (compared to previous embodiments). The tips of the impeller blades 516 are not significantly offset from the edge of the channel 504. Again, the radial clearance may be of similar order of magnitude as manufacturing tolerances. The radial length of the impeller blades (and impeller diameter) have also been reduced.

2.6.2 Interrupter

The blower again includes an interrupter 525 to prevent leak of air from the outlet port 521 to the inlet port 520. The interrupter 525 includes recesses 528 as previously disclosed. In the illustrated configuration, the recesses 528 are similar to the 'V'-shaped inlets previously described; however the recesses could be any profile as shown for the third embodiment. The top housing 502, and a front wall 331 of the bottom housing 503 together form at least part of the interrupter 525, similar to that described with reference to the third embodiment.

2.6.3 Impeller

The impellers described in the third embodiment can be used, although with different dimensions as required.

2.6.4 Example Dimensions for Fifth Embodiment

Exemplary, non-limiting, examples of dimensions of the fifth embodiment will be detailed below.

Figure 83:
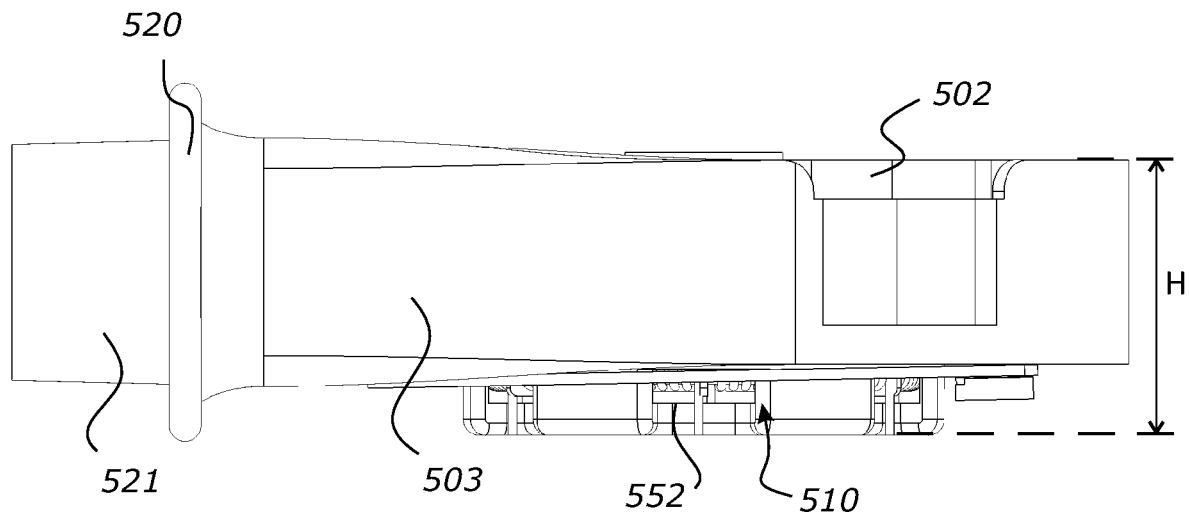
Figure 84:
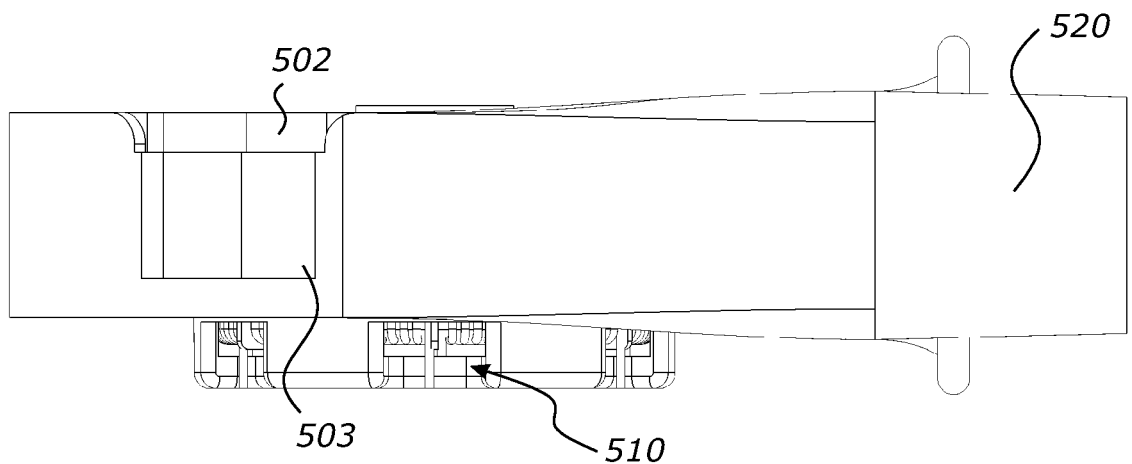
Figure 85:
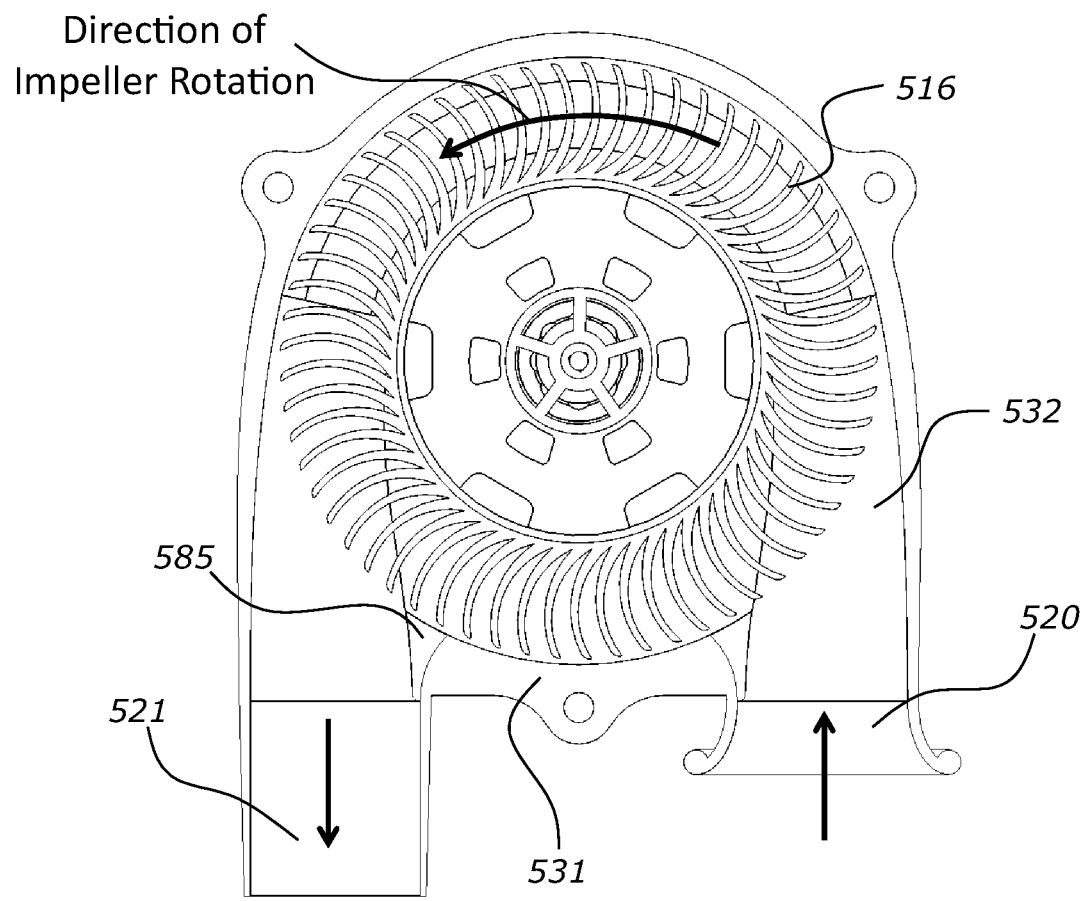
FIG. 85 shows a cross-sectional view of the fifth embodiment of the regenerative blower.
Figure 85:
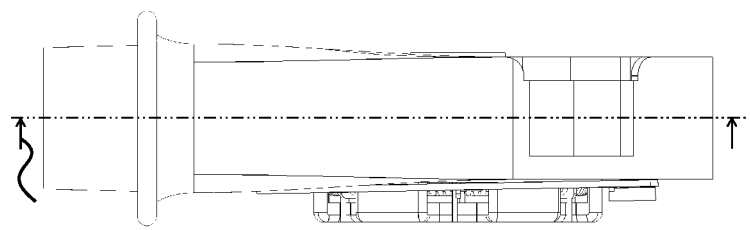

The fifth embodiment has a height H (as shown in FIG. 83) of between about 2.5 cm and 10 cm, such as equal to or about 5.6 cm.

The lengths of the inlet port and outlet port are reduced, and can be between about 1 cm and 5 cm.

Figure 86:
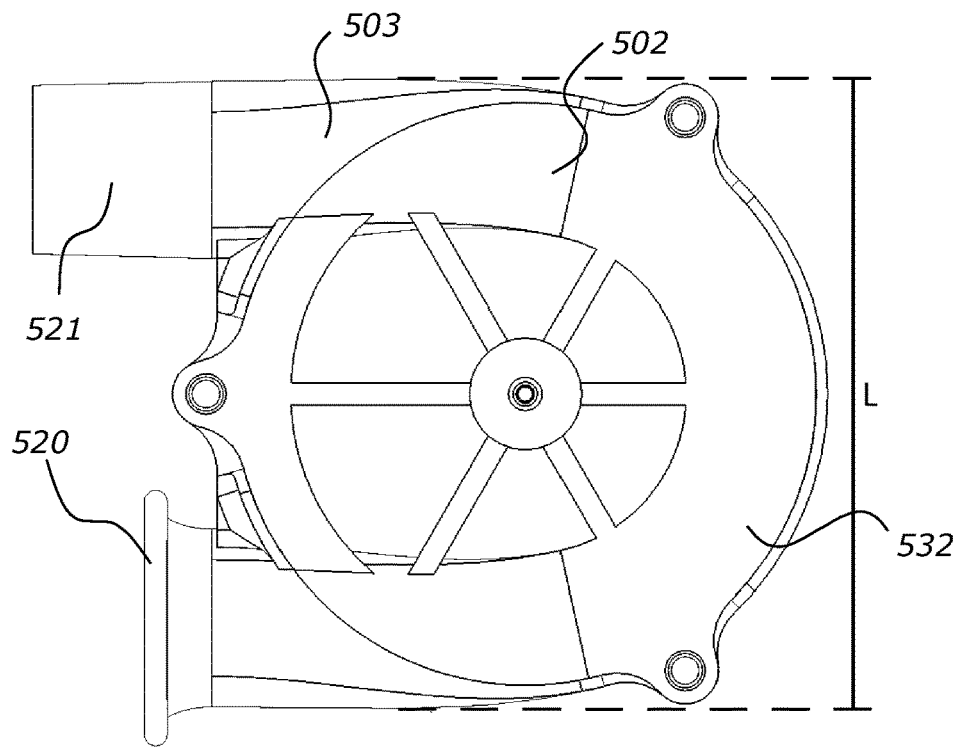
FIG. 86 shows a top view of the fifth embodiment of the regenerative blower.
Figure 87:
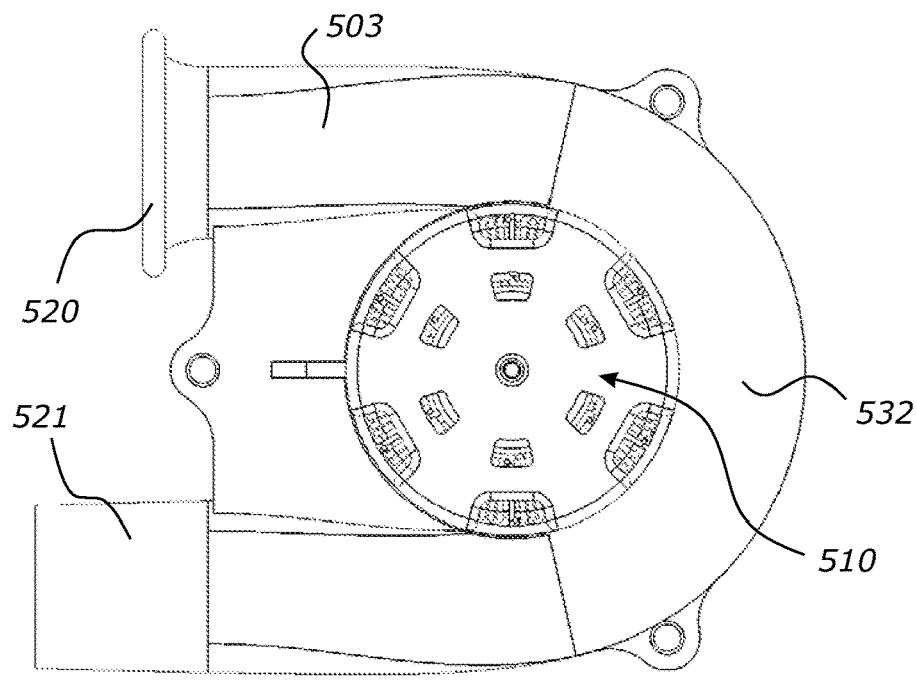
FIG. 87 shows a bottom view of the fifth embodiment of the regenerative blower.

The fifth embodiment has a length L (as shown in FIG. 86) of between about 10 cm and 25 cm, such as equal to or about 17.5 cm.

3. Motor

In the embodiments described, any suitable motor can be used. For example, the motor could be a brushless DC motor operated using sensorless vector control (also termed "field oriented control") controlled by a microcontroller, microprocessor or similar controller 14. The control can be tuned to suit a low inertia impeller. The central hub of the impeller can be engaged with the shaft that extends from the motor. Mounted to the shaft is one or more of, preferably small, magnetic segments to form a rotor. Surrounding the rotor is a laminated stator having a plurality of poles and windings. The stator is mounted to the PCB or other substrate and the windings coupled to the controller 14. The windings are selectively energised by the microcontroller to facilitate rotation of the rotor, and therefore the shaft and impeller, about the central axis defined by the centreline of the shaft. The shaft is held within the motor by a bearing structure. Preferably the bearing structure has one or more bearings and one or more bearing mounts. The bearing mounts engage with the bearings on an inner surface and with the stator on an outer surface. The preferred engagement of the mount to the bearings and the stator is frictional. To promote a frictional engagement, the bearing mounts can be made of a soft, yet resilient and/or flexible material such as silicone rubber or other elastomeric material. The material can be low creep, temperature stable, low compression set with a high tan delta (highly viscous), highly damped. Examples comprise:

Dough Moulding Rubbers like—NBR, Nitrile and Flouro silicone.

Thermo Plastic Elastomers (TPE's) like Santoprene by Exxon

Thermo Plastic Urethanes like Dynaplast by GLS Corporation

Heat Cured Casting Urethanes like 10T90 by National Urethanes

Multiple other cold cast rubbery compounds like RTV (Room Temperature curing Vulcanites) by Dow Corning, Whacker and others.

Such materials allow the mounts to compress when installed, then expand into their chosen location to be held in place by engagement expanded dimension with a restriction.

4. Other Alternatives

Modifications made to the interrupter, housing and impeller have allowed issues with typical regenerative blowers, such as the requirement of high tolerances, and the noise produced to be overcome to allow the described regenerative blowers to be more suitable for use in respiratory therapy applications. Modification can comprise one or more of increasing the length of the interrupter, changing the profile of the interrupter with indents, grooves or the like, and splitting the impeller blades.

Features described for particular embodiments can also be used, where appropriate for alternative embodiments. Not all features for all embodiments have been fully described, because those skilled in the art will be able to apply the features described in some embodiments to the various other embodiments.

5. Experimental Data Showing Performance of Embodiments

Note: The following refers to RG1, which is the first embodiment, RG2, which is the first configuration of the second embodiment, RG2.1, which is the second configuration of the second embodiment, RG3 which is the first configuration of the third embodiment (notch in side wall—FIGS. 47 and 48), RG3.1 which is the second configuration of the third embodiment (notch in front wall—FIGS. 49 and 50), RG3.2 which is the third configuration of the third embodiment (notch on side wall and front wall—FIGS. 51 and 52), RG3.3 is the fourth configuration of the third embodiment (edge between side and front wall—FIGS. 53 and 54), RG3.4 is the fifth configuration of the third embodiment (reduce clearance between impeller and channel—FIGS. 64-66), RG4 which is the fourth embodiment, and RG5 which is the fifth embodiment as described herein. All of blowers RG1, RG2, RG3 and RG4, and the shown test results are for blowers that have the larger of the two options for the bottom housing aperture. This allowed for simpler manufacturing of the prototypes. If desired however, a smaller bottom housing aperture like that of FIG. 10 could be used in any of the blowers.

5.1 First and Second Embodiments

Figure 88:
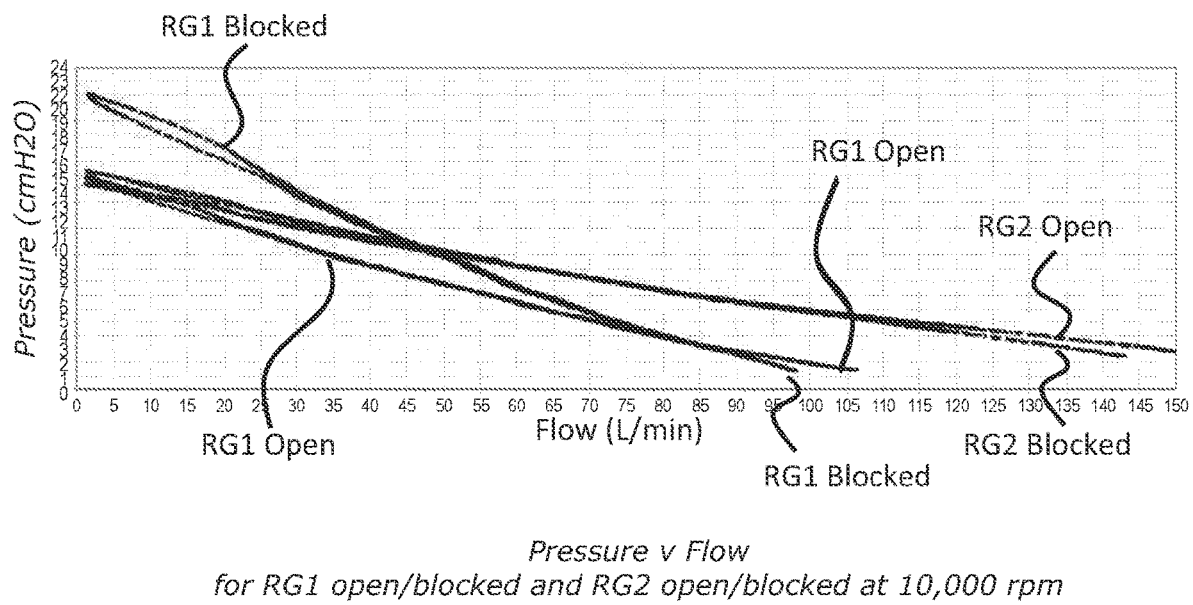
FIGS. 88 to 105 show graphs of experimental data indicating performance of the various embodiments.

FIG. 88 shows a pressure-flow chart displaying pressure (Y axis) and flow (X axis) characteristics of a blower 100 according to the first embodiment (RG1) and a blower according to the first configuration of the second embodiment (RG2), at 10,000 rpm. The pressure and flow characteristics for each blower are shown in two conditions. Each blower of the first and second embodiments tested comprised the larger bottom housing aperture capable of fitting the rotor. The first condition tested was an "open" condition, where the bottom housing cap apertures are open, allowing airflow between the bottom housing aperture (and the impeller channel) and the outside of the blower. The second condition is a "closed" condition, where the bottom housing cap apertures are closed or blocked, thereby preventing airflow between the bottom housing aperture and the outside of the blower (via that pathway). Blocking the bottom housing cap apertures helps reduce leak from the blower in low flow conditions and prevents the apertures from acting as other inlet ports during high flow conditions.

The pressure-flow lines produced for both blowers, in both open and blocked configurations can all be approximated by a linear relationship. According to one linear approximation, the conditions can model the following equations (where P is pressure in cmH2O and F is flow in L/min):

RG1 Open P≈−0.1368F+15

RG1 Closed P≈−0.24F+21.8

RG2 Open P≈−0.092F+16

RG2 Closed P≈−0.085F+15

The observed first embodiment (RG1) Open condition can therefore be modelled by a linear relationship with a gradient within a range of approximately −0.12 to −0.15. The first embodiment Closed condition can be modelled by a linear relationship with a gradient within a range of approximately −0.22 to −0.26. The first configuration of the second embodiment (RG2) Open condition can be modelled by a linear relationship with a gradient within a range of approximately −0.085 to −0.095. The RG2 Closed condition can be modelled by a linear relationship with a gradient within a range of approximately −0.08 to −0.09.

RG2 has similar pressure characteristics to RG1 at low flow conditions (although lower pressure performance when the bottom housing cap apertures are blocked), however outperforms RG1 in higher flow conditions. As a result, RG2 is an improved regenerative blower for high flow conditions.

Figure 89:
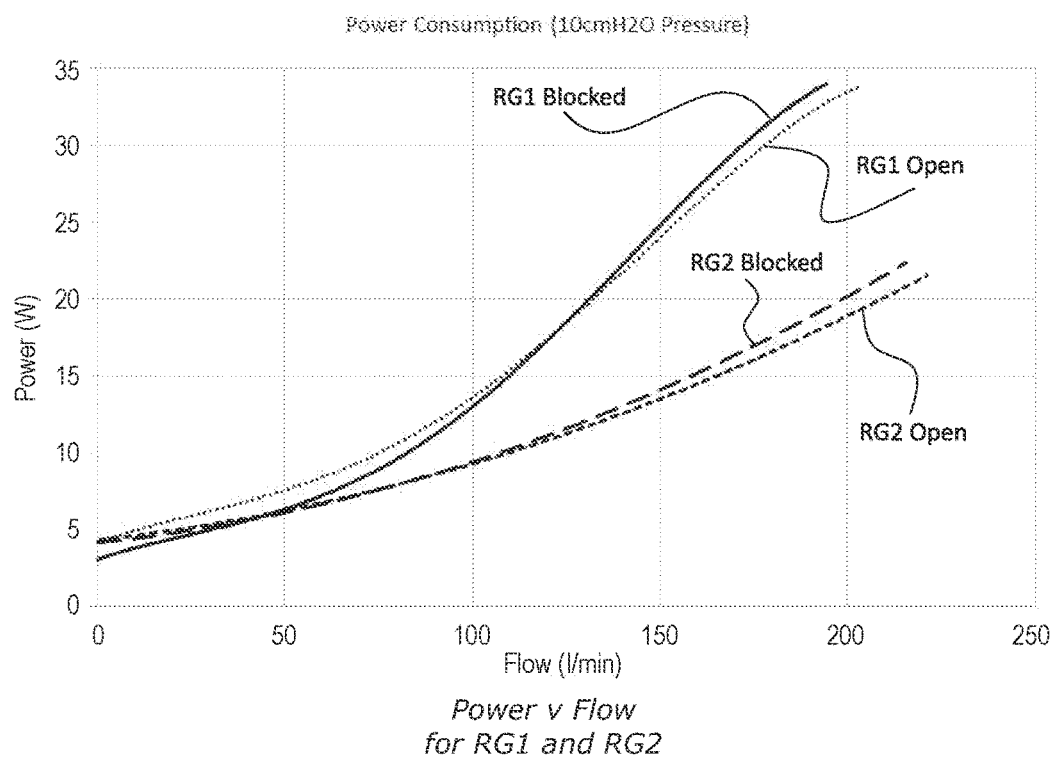

FIG. 89 shows a power-flow chart for RG1 and RG2, displaying the power consumed (Y axis) at a designated flow (X axis). The power and flow data shown is for when the blowers are operating at 10 cmH2O of pressure, which is a typical CPAP pressure. Varying the flow and power was done by varying the operating RPM of the blower.

RG2 uses substantially less power than RG1 in both the open and blocked conditions for flows above approximately 50 L/min. For flows below 50 L/min, the power requirements of RG2 are approximately similar to those of RG1.

Figure 90:
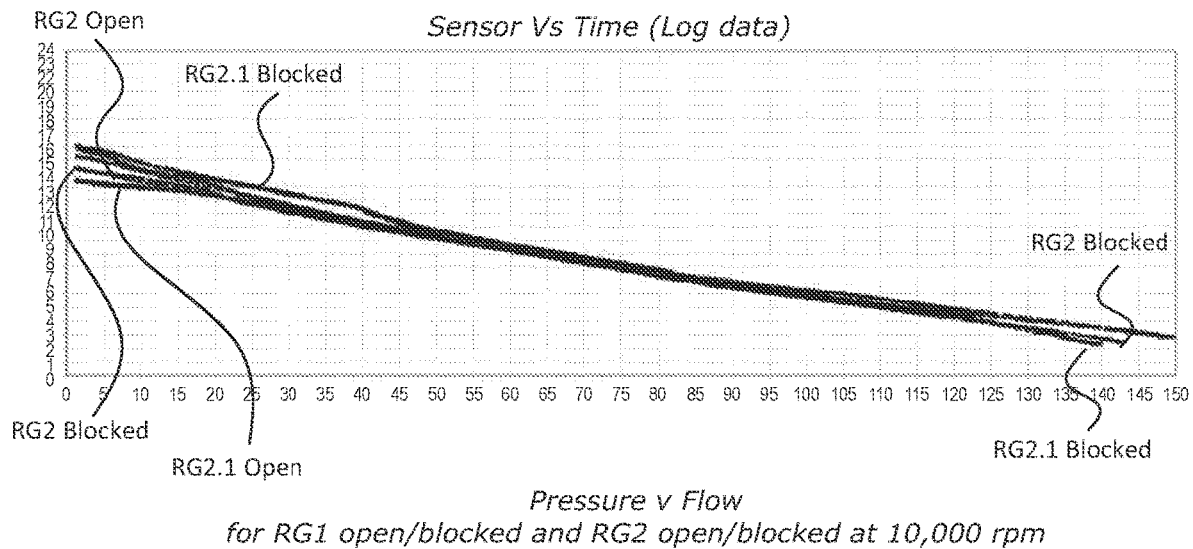

FIG. 90 shows a pressure-flow chart displaying the pressure (Y axis) and flow (X axis) characteristics of RG2 and RG2.1 in open and closed conditions at 10 k rpm. Again, each of RG2 and RG2.1 tested include the larger bottom housing aperture capable of fitting the rotor.

The pressure-flow lines produced for both blowers, in both open and blocked configurations can all be approximated by a linear relationship. According to one linear approximation, the data can model the following equations:

RG2 Open P≈−0.092F+16

RG2 Closed P≈−0.085F+15

RG2.1 Open P≈−0.0769F+14.4

RG2.1 Closed P≈−0.0818F+14.6

The observed RG2 Open condition can therefore be modelled by a linear relationship with a gradient within a range of approximately −0.085 to −0.095. The RG2 Closed condition can be modelled by a linear relationship with a gradient within a range of approximately −0.08 to −0.09. The RG2.1 Open condition can be modelled by a linear relationship with a gradient within a range of approximately −0.07 to −0.08. The RG2.1 Closed condition can be modelled by a linear relationship with a gradient within a range of approximately −0.08 to −0.09.

Figure 91:
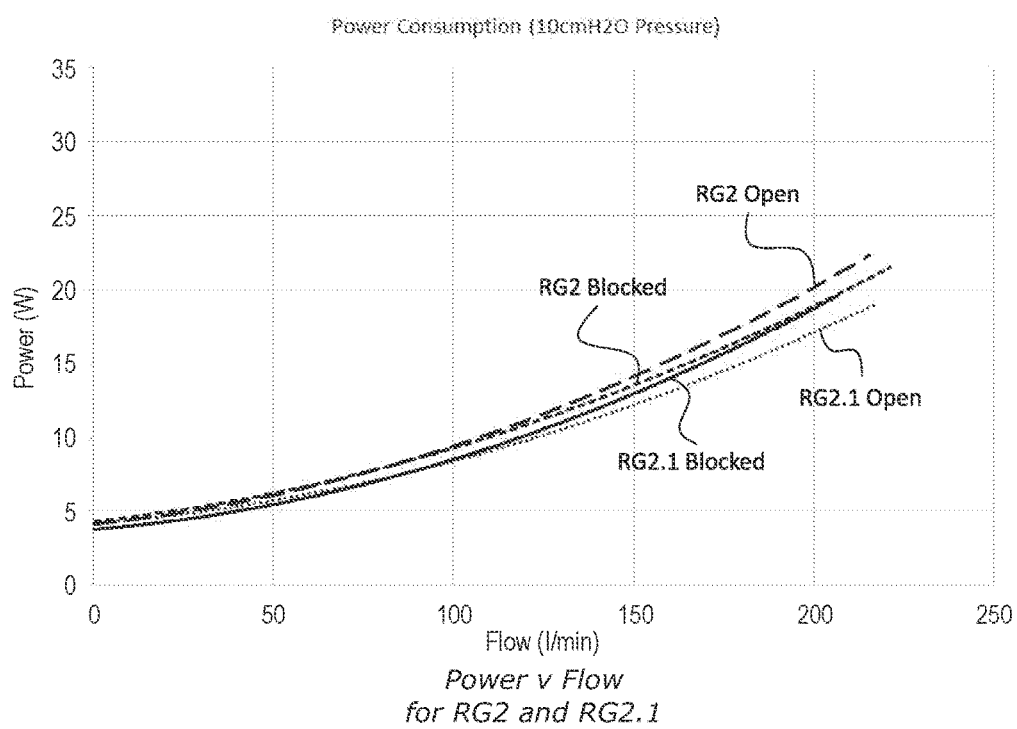

FIG. 91 shows a power-flow chart for RG2 and RG2.1, displaying the power consumed (Y axis) at a designated flow (X axis). The power and flow data shown is for when the blowers are operating at 10 cmH2O of pressure.

At higher flows, RG2.1 uses less power than RG2. At low flows, the power use is comparable, however RG2.1 still uses marginally less power.

5.2 Third Embodiment

Figure 92:
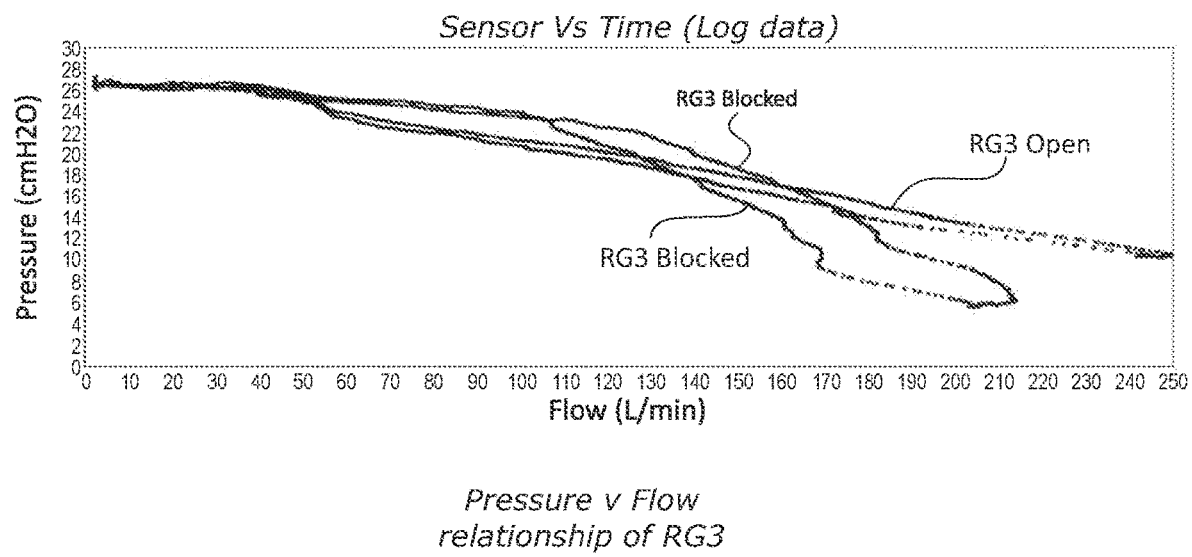

FIG. 92 shows a chart of the pressure-flow relationship of blower RG3 at 10 k RPM in an open condition and a closed condition as defined for the previous blowers. Again, RG3 includes the larger bottom housing aperture capable of fitting the rotor.

The curve for RG3 blocked exhibits hysteresis. Similar behaviour is observed in the curve for RG3 open.

At 10 k RPM, RG3 produces higher flow and pressure characteristics than a comparably dimensioned centrifugal blower. This allows much lower RPMs to be used to produce the pressures and flows desired for CPAP therapy, allowing a reduction in noise, increased bearing life and the possibility to use plain bearings, bush bearings, polymeric bearings etc.

Figure 93:
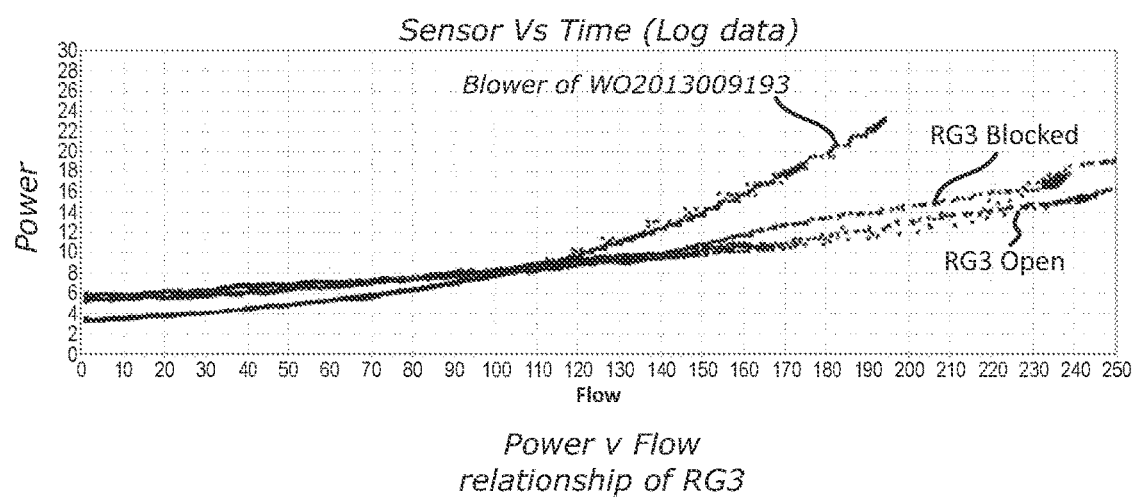

FIG. 93 shows a chart of the power-flow relationship of blower RG3 at 10 cmH2O in an open condition, and in a blocked condition as defined for previous blowers.

Efficiency may be an important factor in certain applications, for example portable CPAP devices, however for applications where the device is connected to the grid, aside from electrical costs, efficiency is not necessarily a major issue. Therefore, if a regenerative blower is produced with an improved characteristic like lower noise emission, higher power requirements may be an allowable trade off in certain circumstances.

A noise test was conducted to compare the noise produced by the blowers RG3, RG3.1, RG3.2 and RG3.3. ISO 80601-2-70:2015 Medical Electrical Equipment—Part 2-70 outlines the particular requirements for basic safety and essential performance of sleep apnoea breathing therapy equipment. ISO 4871:1996 requires a declaration and verification of the noise emission values of machinery and equipment. A microphone array was set up as per ISO 3744:2010 to determine sound power levels and sound energy levels of noise sources (the blower) using sound pressure. The noise produced by the respective blowers across a spectrum of frequencies was recorded. Each blower was arranged to produce approximately 10 cmH2O of pressure at a flow of approximately 30 L/min for the test, allowing a comparison under typical CPAP operating conditions to be made.

Figure 61:
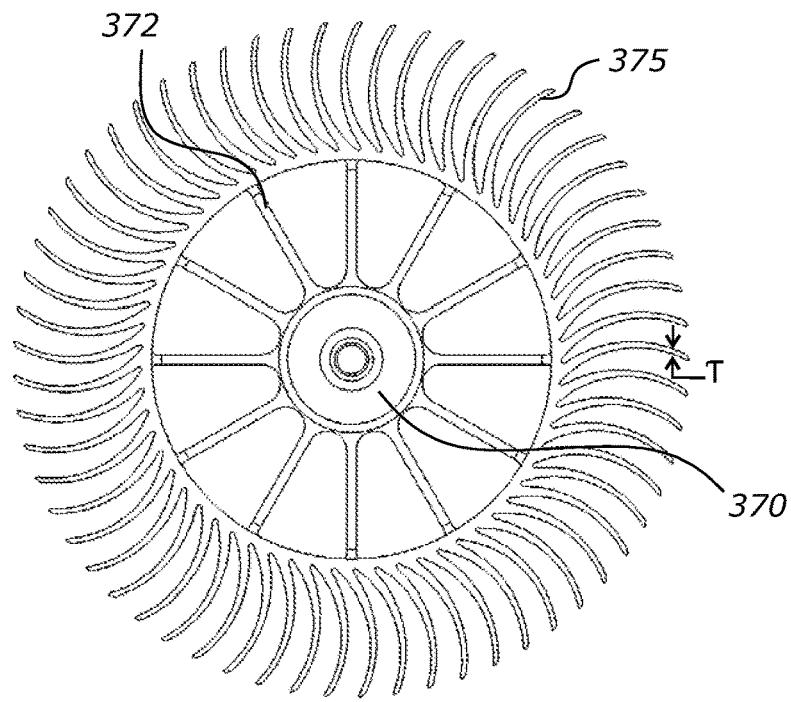
Figure 94:
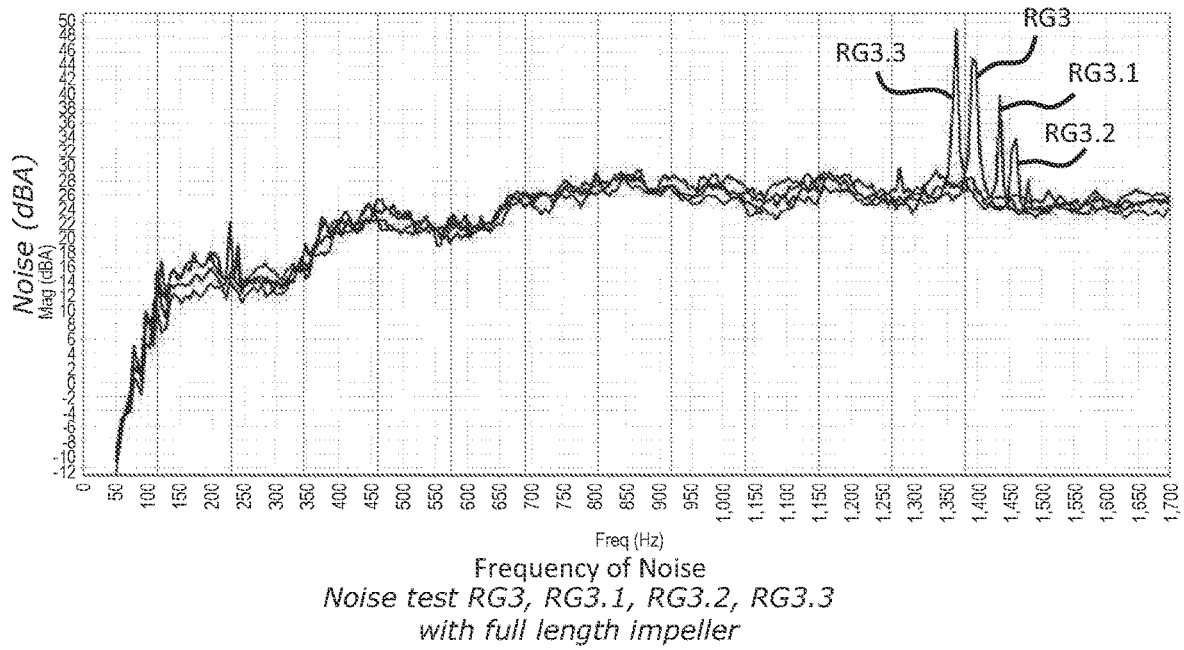

FIG. 94 shows the results of a noise test conducted with RG3, 3.1, 3.2 and 3.3 using the previously described full length impeller of FIGS. 60 and 61.

The peaks identified around 1400 Hz correspond with the blade pass frequency caused by the impeller blades passing the interrupter of each respective blower. The locations of the peaks aren't aligned on the same frequency as the prominent blade pass frequency produced by each blower was somewhat altered due to somewhat different RPM settings being required due to the various blower model's different pressure and flow performance. The different interrupter designs resulted in each blower needing to be operated at a slightly different RPM to achieve the 10 cmH2O of pressure required for the test.

The loudest blower is RG3.3 (with the square interrupter). The quietest blower is RG3.2 (with the indents, and the groves across the interrupter). RG3.2 blade pass noise was approximately 34 dBA (A-weighted decibels) at its highest, while RG3.3 blade pass noise was approximately 49 dBA. The amplitudes of the peaks in noise produced tend to decrease, while most other frequencies stay the same.

Figure 95:
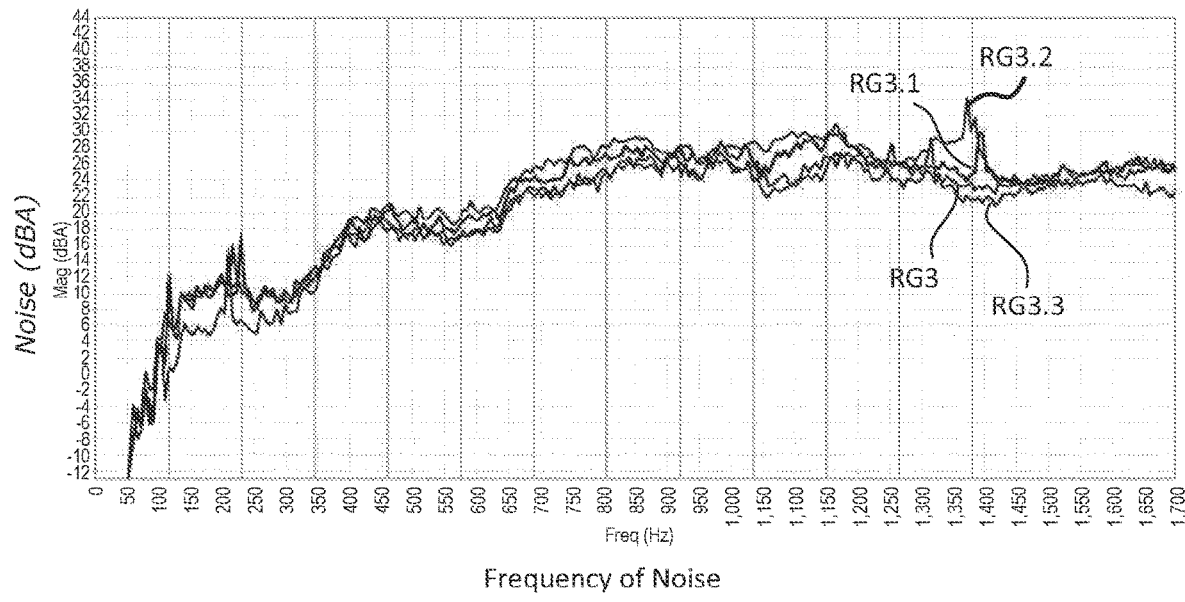

FIG. 95 shows the results of the noise test conducted with RG3, 3.1, 3.2 and 3.3 using the previously described impeller with offset upper and lower impeller blades, and the annular impeller support plate 379.

The effects of blade pass of the impeller can be seen to be substantially reduced by the use of the offset-web impeller for RG3, RG3.1 and RG3.3.

Figure 96:
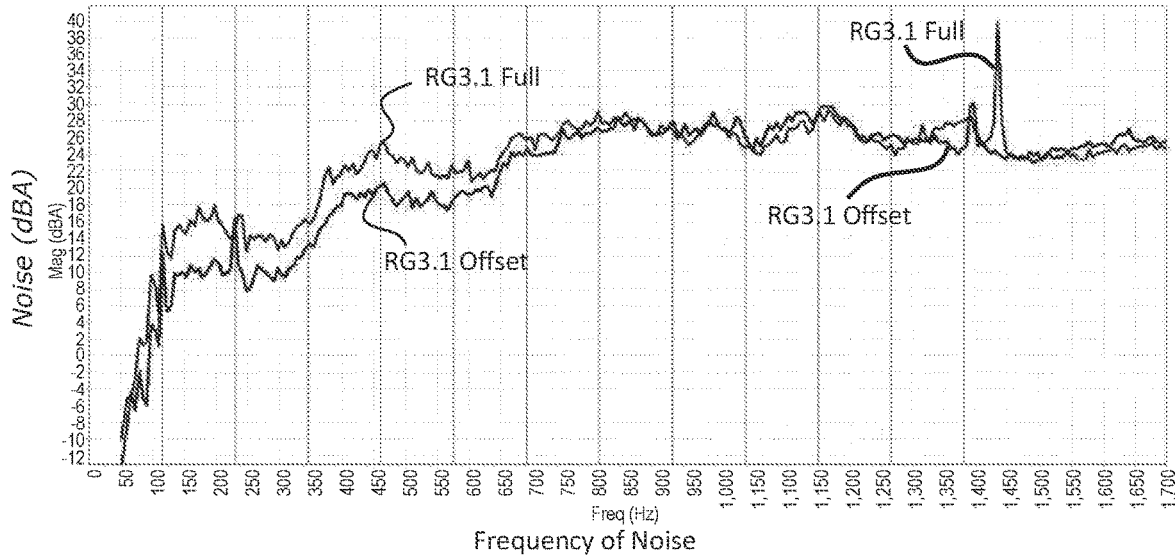

FIG. 96 shows the noise test results for RG3.1, comparing RG3.1 with the impeller with full length impeller blades, to RG3.1 with the impeller with offset impeller blades and the web.

The use of the offset impeller notably reduces the noise produced by the blower as the impeller blades pass the interrupter. The noise produced at other frequencies is also generally lower with the offset impeller, particularly for the lower frequencies. This pattern is also observed for RG3 and RG3.3.

Figure 97:
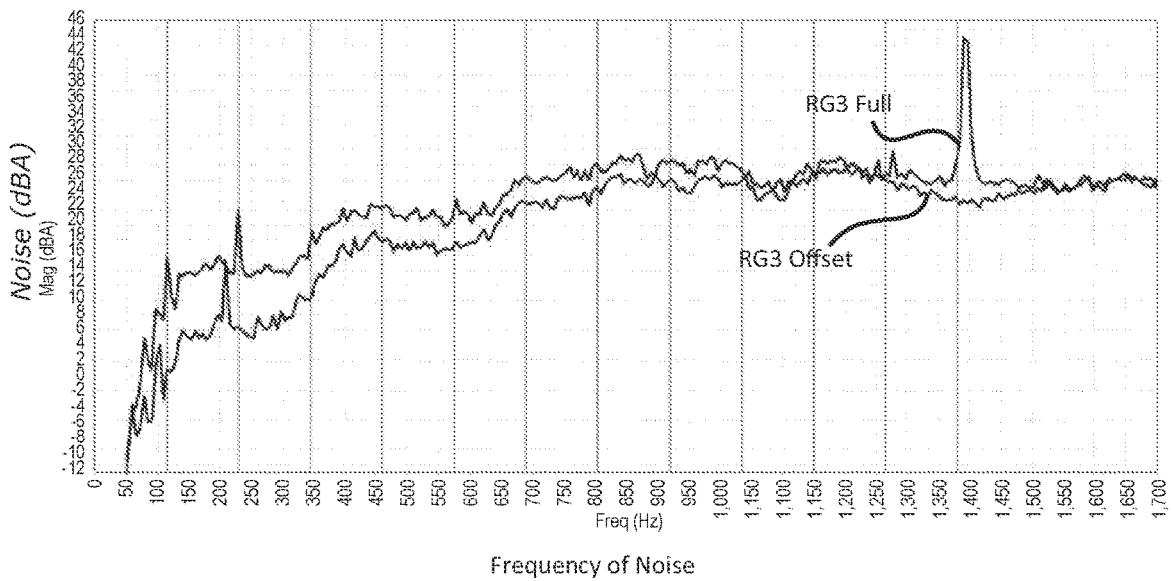

FIG. 97 shows the noise test results for RG3, comparing RG3 with the impeller with full length impeller blades, to RG3 with the impeller with offset impeller blades and the web.

Figure 98:
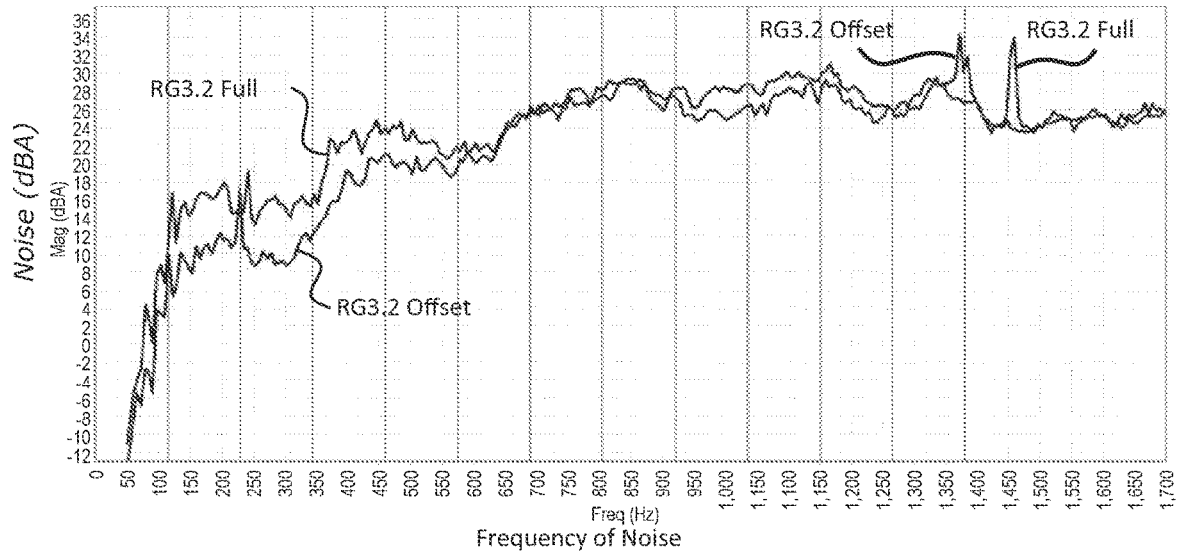

FIG. 98 shows the noise test results for RG3.2, comparing RG3.2 with the impeller with full length impeller blades, to RG3.2 with the impeller with offset impeller blades and the web.

The use of the offset impeller has less of an effect on the maximum noise produced by the blower. The frequency of which the noise is produced is shifted from approximately 1450 Hz with the full impeller to approximately 1400 Hz with the offset impeller due to the reduction in speed; however the magnitude remains relatively similar at approximately 34 dBA.

The noise produced at other frequencies is generally lower with the offset impeller, particularly for the lower frequencies.

Figure 99:
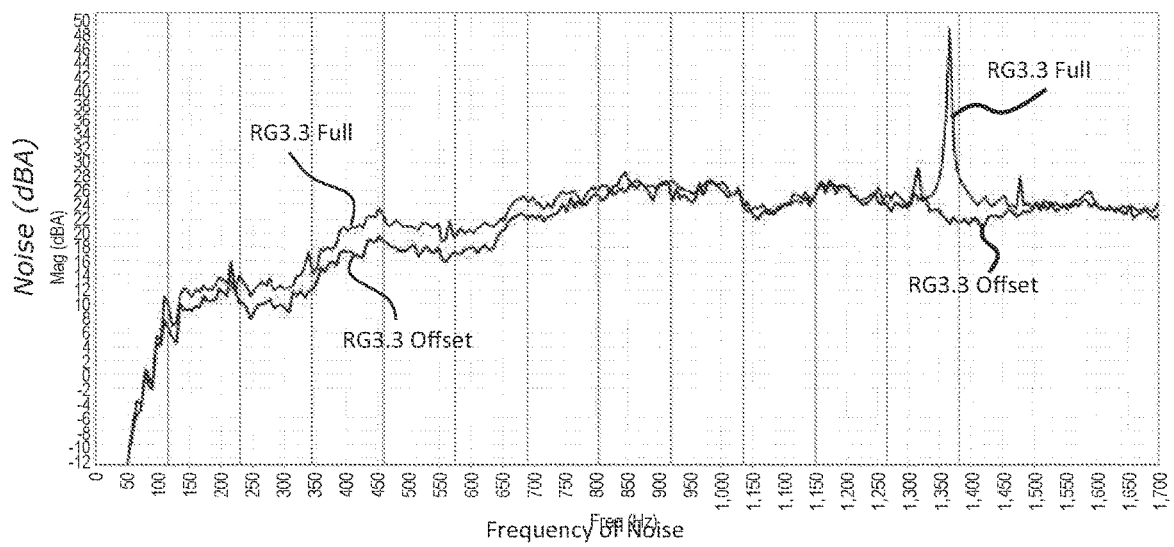

FIG. 99 shows the noise test results for RG3.3, comparing RG3.3 with the impeller with full length impeller blades, to RG3.3 with the impeller with offset impeller blades and the web.

This modification result in improved performance of the blower under certain conditions.

Figure 100:
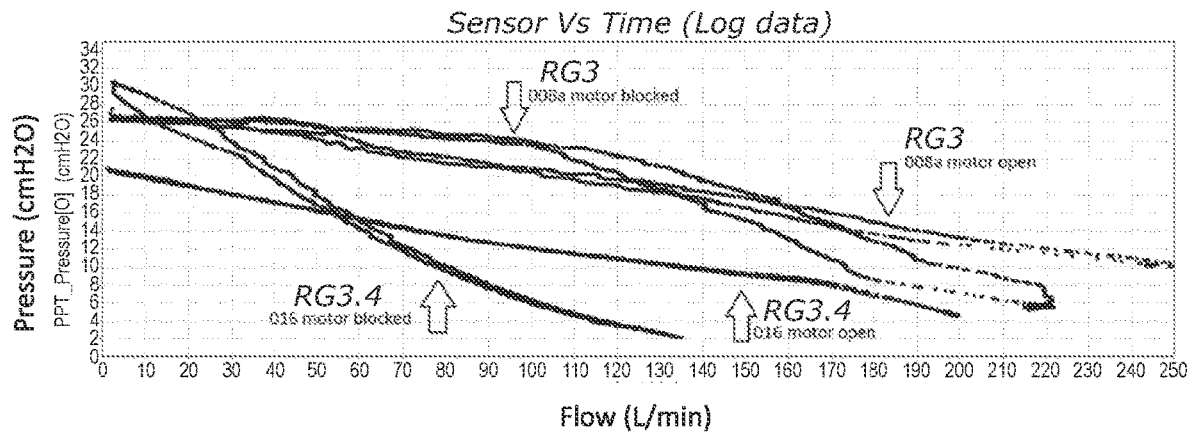

FIG. 100 shows a number of pressure-flow curves comparing RG3.4 to RG3.

Figure 101:
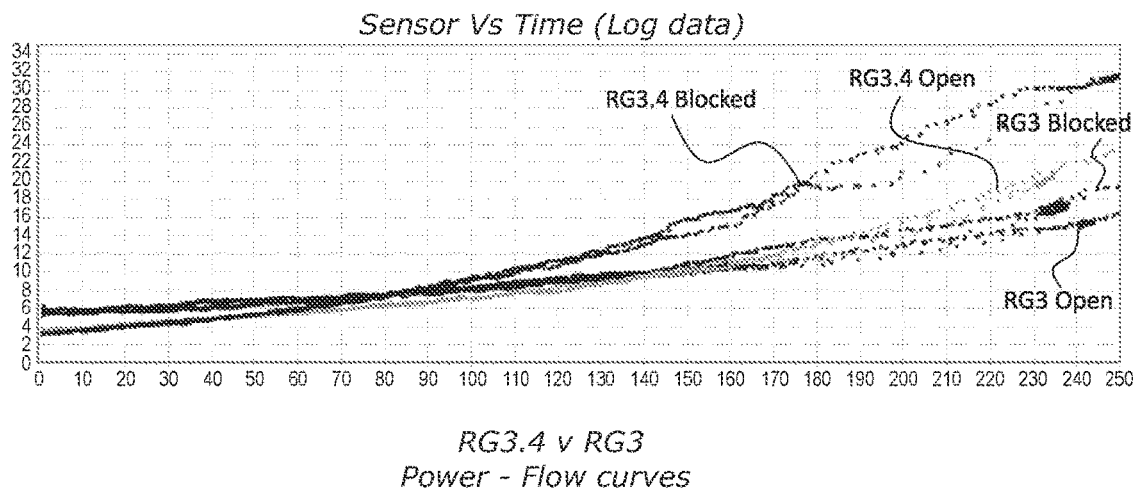

As can be seen, the modification can result in improved pressures under low flow conditions under a blocked bottom housing cap aperture condition. Furthermore, the modification can result in lower power requirements of the blower under low flow conditions. FIG. 101 shows this in a power-flow comparison of RG3.4 and RG3 at 10 cmH2O.

5.3 Fourth Embodiment

Figure 102:
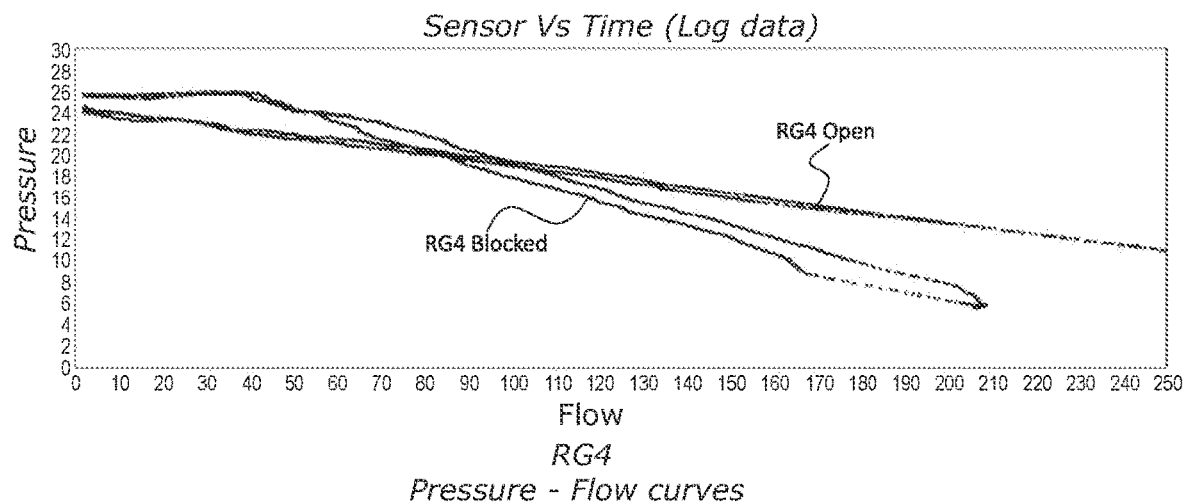

FIG. 102 shows a chart of the pressure-flow characteristics of RG4 with the impeller with offset blades separated by the annular impeller support plate 379, and a bottom housing aperture of size corresponding to the rotor.

Figure 103:
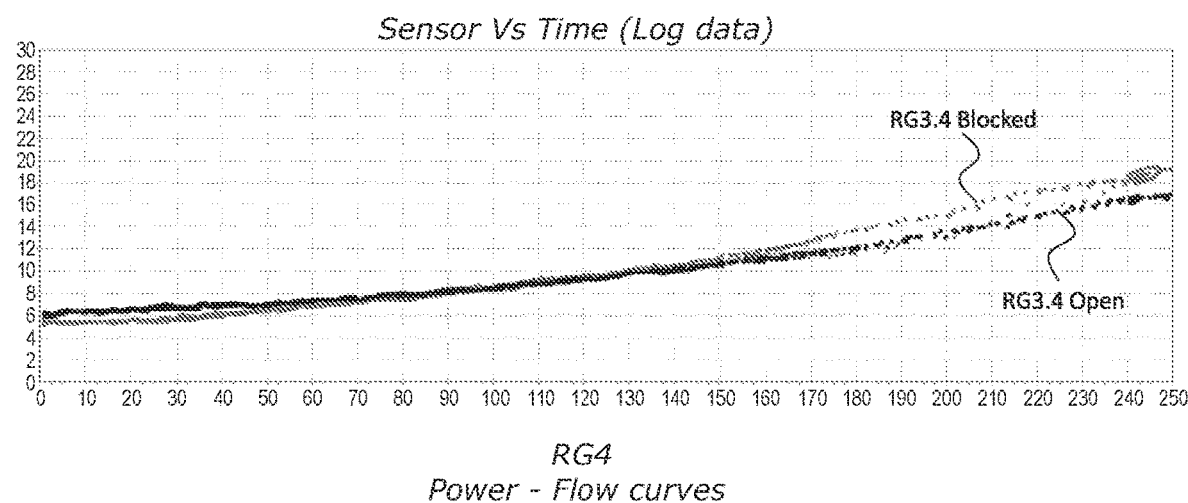

FIG. 103 shows a chart of the power-flow characteristics of RG4 at 10 cmH2O with the impeller with offset blades separated by the annular impeller support plate 379, and a bottom housing aperture of size corresponding to the rotor.

This modification results in improved performance of the blower under certain conditions. FIG. 103 shows a number of pressure-flow curves comparing RG3.4 to RG3.

Figure 104:
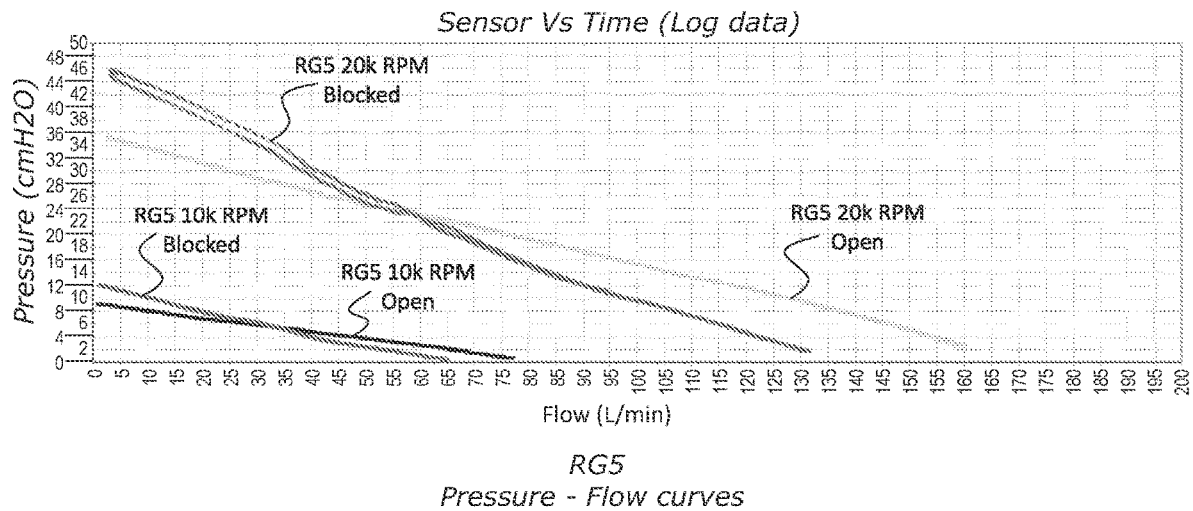

As can be seen, the modification can result in improved pressures under low flow conditions under a blocked bottom housing cap aperture condition. Furthermore, the modification can result in lower power requirements of the blower under low flow conditions. FIG. 104 shows this in a power-flow comparison of RG3.4 and RG3 at 10 cmH2O.

5.4 Fifth Embodiment

FIG. 104 shows a comparison of the pressure-flow curves for RG5 with full length (height) impeller blades at 10 k RPM and at 20 k RPM under the open and blocked flow conditions defined for previous blowers.

Figure 105:
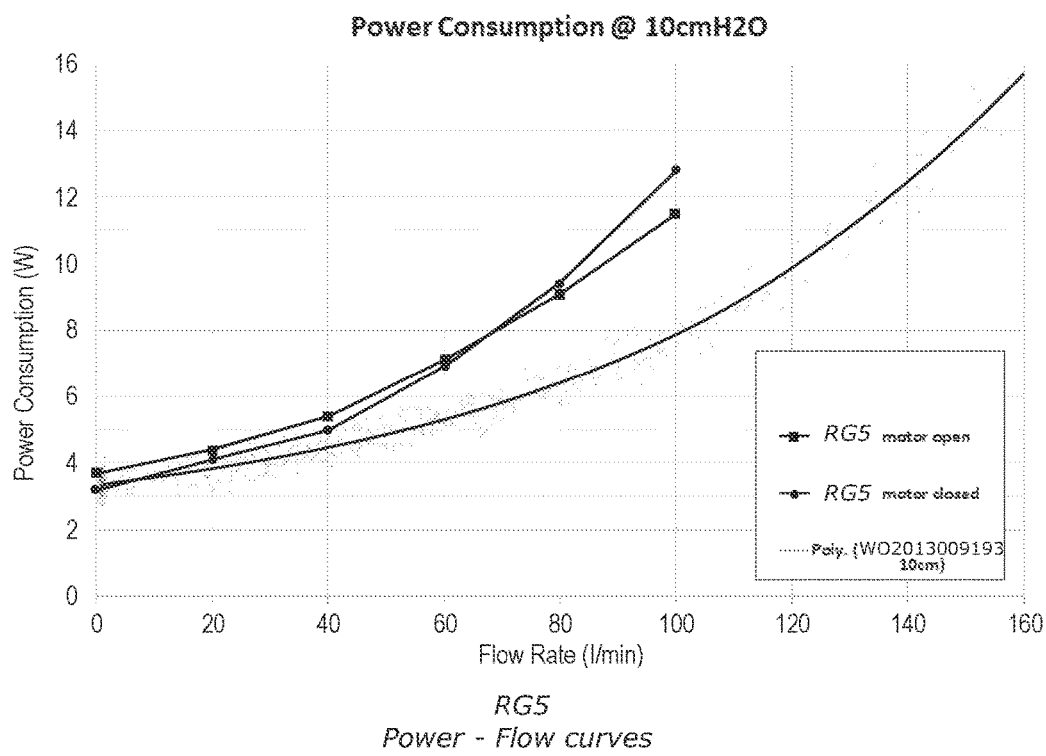

FIG. 105 shows a comparison of the power-flow curves for RG5 with full length (height) impeller blades at 10 cmH2O under the open and blocked bottom housing aperture condition defined previously.

The power consumption of RG5 ranges from approximately 3.5 W at 0 L/min (blocked outlet) to approximately 12 W at 100 L/min.

The invention claimed is:

1. A regenerative blower comprising:
a housing;
a first port and second port in the housing providing an inlet and outlet;
an airflow channel extending between the first and second ports;
an impeller rotatable in an impeller channel to promote airflow in the airflow channel from the first port to the second port;
a motor to drive the impeller;
an interrupter between the first and second ports to limit airflow from the second port to the first port, wherein the housing comprises an aperture that provides a third port; and
wherein the aperture is an outlet from the impeller channel and/or the airflow channel under relatively low flow conditions, and an inlet under relatively high flow conditions.

2. A regenerative blower according to claim 1 wherein the housing comprises a top housing and a bottom housing and the aperture comprises one or more openings in the top housing.

3. A regenerative blower according to claim 1 wherein the motor comprises a rotor and the aperture having a diameter that is shaped to enable, during manufacture, an assembly of the rotor coupled to the impeller by a shaft to be placed in the housing through the aperture.

4. A regenerative blower according to claim 1 wherein the housing comprises a top housing and a bottom housing with a bottom plate, and the aperture is in the bottom plate of the bottom housing.

5. A regenerative blower according to claim 4 wherein the housing further comprises a bottom housing cap, and wherein the bottom housing cap includes at least one bottom housing cap aperture.

6. A regenerative blower according to claim 1 wherein the housing comprises a top housing and a bottom housing, the impeller is disposed between the top housing and the bottom housing, the motor is disposed at least partially in the bottom housing, and the top housing is open to the bottom housing such that there is no plate or other barrier of the housing separating the impeller and the motor.

7. A regenerative blower according to claim 6 wherein the airflow channel comprises an upper channel and a lower channel.

8. A regenerative blower according to claim 7 wherein the impeller channel separates the upper channel and the lower channel.

9. A regenerative blower according to claim 6 wherein lateral ends of the impeller rotate adjacent an interior lateral face of the housing.

10. A regenerative blower according to claim 1 further comprising a one-way valve for the third port.

11. A regenerative blower according to claim 1 further comprising an arcuate wall in the impeller channel forming an inner impeller channel and an outer impeller channel, the arcuate wall having an air flow opening between the inner impeller channel and the outer impeller channel.

12. A regenerative blower according to claim 11 wherein the impeller comprises inner impeller blades and outer impeller blades which rotate in the inner impeller channel and the outer impeller channel, respectively.

13. A regenerative blower according to claim 1 wherein the first port is an inlet and the second port is an outlet or the first port is an outlet and the second port is an inlet.

* * * * *